(12) United States Patent
Crowe et al.

(10) Patent No.: US 11,623,952 B2
(45) Date of Patent: Apr. 11, 2023

(54) IL-23 AND TNF-ALPHA BINDING BI-SPECIFIC HEAVY CHAIN POLYPEPTIDES

(71) Applicant: SORRISO PHARMACEUTICALS, INC., San Diego, CA (US)

(72) Inventors: Scott Crowe, Cambridge (GB); Marion Cubitt, Cambridge (GB); Tim Carlton, Cambridge (GB); Luana Maggiore, Cambridge (GB); Lurdes Duarte, Cambridge (GB); Kevin Roberts, Cambridge (GB); Mike West, Cambridge (GB)

(73) Assignee: SORRISO PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 17/750,112

(22) Filed: May 20, 2022

(65) Prior Publication Data

US 2022/0332810 A1    Oct. 20, 2022

Related U.S. Application Data

(63) Continuation of application No. 17/620,026, filed as application No. PCT/GB2020/051495 on Jun. 19, 2020.

(30) Foreign Application Priority Data

Jun. 21, 2019  (EP) ..................................... 19181870

(51) Int. Cl.

| C07K 16/24 | (2006.01) |
| A61K 39/395 | (2006.01) |
| A61P 37/06 | (2006.01) |
| A61P 1/12 | (2006.01) |
| A61K 39/00 | (2006.01) |

(52) U.S. Cl.
CPC ........ *C07K 16/244* (2013.01); *A61K 39/3955* (2013.01); *A61P 1/12* (2018.01); *A61P 37/06* (2018.01); *A61K 39/00* (2013.01); *C07K 2317/565* (2013.01); *C07K 2317/567* (2013.01); *C07K 2317/569* (2013.01); *C07K 2317/76* (2013.01)

(58) Field of Classification Search
None
See application file for complete search history.

(56) References Cited

U.S. PATENT DOCUMENTS

| 3,300,077 A | 1/1967 | David et al. |
| 5,780,028 A | 7/1998 | Graham |
| 8,399,188 B2 | 3/2013 | Zhao et al. |
| 9,080,157 B2 | 7/2015 | Convents et al. |
| 9,527,925 B2 | 12/2016 | Gschwind et al. |
| 9,932,412 B2 | 4/2018 | Kim et al. |
| 10,633,438 B2 | 4/2020 | Crowe et al. |
| 10,772,839 B2 | 9/2020 | Crowe et al. |
| 10,980,748 B2 | 4/2021 | Crowe et al. |
| 2004/0041867 A1 | 3/2004 | Lapstun et al. |
| 2005/0147612 A1 | 7/2005 | Yayon et al. |
| 2006/0034833 A1 | 2/2006 | Beirnaert |
| 2006/0034845 A1 | 2/2006 | Silence et al. |
| 2006/0057197 A1 | 3/2006 | Han et al. |
| 2006/0138181 A1 | 6/2006 | Thom et al. |
| 2007/0020267 A1 | 1/2007 | Fuh et al. |
| 2007/0042399 A1 | 2/2007 | Wright et al. |
| 2007/0077249 A1 | 4/2007 | Silence et al. |
| 2007/0178082 A1 | 8/2007 | Silence et al. |
| 2007/0237769 A1 | 10/2007 | Silence et al. |
| 2008/0031770 A1 | 2/2008 | Heselton et al. |
| 2008/0039761 A1 | 2/2008 | Heaton et al. |
| 2008/0122965 A1 | 5/2008 | Fang |
| 2008/0145420 A1 | 6/2008 | Simon |
| 2008/0149143 A1 | 6/2008 | Chou et al. |
| 2008/0260820 A1 | 10/2008 | Borrelly et al. |
| 2009/0064457 A1 | 3/2009 | Brustle |
| 2009/0064460 A1 | 3/2009 | Tang et al. |
| 2010/0077422 A1 | 3/2010 | Bushinsky |
| 2010/0137213 A1 | 6/2010 | Fernandez et al. |
| 2010/0239682 A1 | 9/2010 | Andremont et al. |
| 2010/0260857 A1 | 10/2010 | Fallon et al. |

(Continued)

FOREIGN PATENT DOCUMENTS

| EP | 2275443 A1 | 1/2011 |
| EP | 2275443 B1 | 12/2015 |

(Continued)

OTHER PUBLICATIONS

2005 Drug Bank Data (https://wwwdrugbank.caldrugs/DB00085) for Pancrelipase.
Arbabi-Ghahroudi et al.: Selection and identification of single domain antibody fragments from camel heavy-chain antibodies. FEBS Letters 414(3):521-526 (1997).

(Continued)

*Primary Examiner* — Joanne Hama
*Assistant Examiner* — Fozia M Hamud
(74) *Attorney, Agent, or Firm* — Wilson Sonsini Goodrich & Rosati

(57) ABSTRACT

There is provided inter alia a polypeptide comprising an immunoglobulin chain variable domain which binds to IL-23, wherein the immunoglobulin chain variable domain comprises three complementarity determining regions (CDR1-CDR3) and four framework regions (FR1-FR4), wherein CDR1 comprises a sequence sharing 60% or greater sequence identity with SEQ ID NO: 1, CDR2 comprises a sequence sharing 50% or greater sequence identity with SEQ ID NO: 2 and CDR3 comprises a sequence sharing 50% or greater sequence identity with SEQ ID NO: 3.

15 Claims, 8 Drawing Sheets
Specification includes a Sequence Listing.

(56) References Cited

U.S. PATENT DOCUMENTS

| | | |
|---|---|---|
| 2011/0028695 A1 | 2/2011 | Revets et al. |
| 2011/0098518 A1 | 4/2011 | Minoux et al. |
| 2011/0109365 A1 | 5/2011 | Mai |
| 2011/0112229 A1 | 5/2011 | Nagaoka et al. |
| 2011/0229476 A1 | 9/2011 | Liu et al. |
| 2012/0130872 A1 | 5/2012 | Baughman et al. |
| 2012/0151199 A1 | 6/2012 | Shriver |
| 2013/0173687 A1 | 7/2013 | Tuchman et al. |
| 2014/0030049 A1 | 1/2014 | Imai et al. |
| 2014/0044730 A1 | 2/2014 | Yancopoulos et al. |
| 2014/0141152 A1 | 5/2014 | Sostek et al. |
| 2014/0170212 A1 | 6/2014 | Ortenzi et al. |
| 2014/0186365 A1 | 7/2014 | Robinson et al. |
| 2014/0294826 A1 | 10/2014 | Shoemaker |
| 2014/0377287 A1 | 12/2014 | Govindan et al. |
| 2015/0017183 A1 | 1/2015 | Seidah et al. |
| 2015/0058173 A1 | 2/2015 | Schmeling et al. |
| 2015/0147318 A1 | 5/2015 | Bergeron et al. |
| 2015/0176031 A1 | 6/2015 | Streffer |
| 2015/0337035 A1 | 11/2015 | Anderson et al. |
| 2016/0060338 A1 | 3/2016 | Barrett et al. |
| 2016/0156465 A1 | 6/2016 | Vaikuntanathan et al. |
| 2016/0264659 A1 | 9/2016 | Heavner et al. |
| 2017/0002069 A1 | 1/2017 | Crowe et al. |
| 2017/0022271 A1 | 1/2017 | Hoffman et al. |
| 2017/0260266 A1 | 9/2017 | Ahmed et al. |
| 2018/0009881 A1 | 1/2018 | Crowe et al. |
| 2018/0037639 A1 | 2/2018 | Crowe et al. |
| 2018/0100008 A1 | 4/2018 | Crowe et al. |
| 2018/0100009 A1 | 4/2018 | Crowe et al. |
| 2019/0008778 A1 | 1/2019 | Crowe et al. |
| 2019/0040156 A1 | 2/2019 | Demarest et al. |
| 2019/0092855 A1 | 3/2019 | Crowe et al. |
| 2019/0307891 A1 | 10/2019 | Crowe et al. |
| 2020/0079844 A1 | 3/2020 | Beirnaert |
| 2020/0317769 A1 | 10/2020 | Crowe et al. |
| 2021/0198345 A1 | 7/2021 | Crowe et al. |
| 2021/0317195 A1 | 10/2021 | Crowe et al. |
| 2022/0242945 A1 | 8/2022 | Crowe et al. |
| 2022/0363769 A1 | 11/2022 | Crowe et al. |

FOREIGN PATENT DOCUMENTS

| | | |
|---|---|---|
| EP | 2955196 A1 | 12/2015 |
| WO | WO-9102078 A1 | 2/1991 |
| WO | WO-9201047 A1 | 1/1992 |
| WO | WO-9300077 A1 | 1/1993 |
| WO | WO-9404678 A1 | 3/1994 |
| WO | WO-9425591 A1 | 11/1994 |
| WO | WO-9508562 A1 | 3/1995 |
| WO | WO-9634103 A1 | 10/1996 |
| WO | WO-9923221 A2 | 5/1999 |
| WO | WO-0212502 A2 | 2/2002 |
| WO | WO-0248382 A2 | 6/2002 |
| WO | WO-03035694 A2 | 5/2003 |
| WO | WO-2004009776 A2 | 1/2004 |
| WO | WO-2004037205 A2 | 5/2004 |
| WO | WO-2004041862 A2 | 5/2004 |
| WO | WO-2004041863 A2 | 5/2004 |
| WO | WO-2004041865 A2 | 5/2004 |
| WO | WO-2004041867 A2 | 5/2004 |
| WO | WO-2006122786 A2 | 11/2006 |
| WO | WO-2006122787 A1 | 11/2006 |
| WO | WO-2006138181 A2 | 12/2006 |
| WO | WO-2007005955 A2 | 1/2007 |
| WO | WO-2007025977 A2 | 3/2007 |
| WO | WO-2007027714 A2 | 3/2007 |
| WO | WO-2007048022 A2 | 4/2007 |
| WO | WO-2007070948 A1 | 6/2007 |
| WO | WO-2007104529 A2 | 9/2007 |
| WO | WO-2008020079 A1 | 2/2008 |
| WO | WO-2008031770 A2 | 3/2008 |
| WO | WO-2008039761 A2 | 4/2008 |
| WO | WO-2008049897 A1 | 5/2008 |
| WO | WO-2008101985 A2 | 8/2008 |
| WO | WO-2008101985 A3 | 10/2008 |
| WO | WO-2008122965 A2 | 10/2008 |
| WO | WO-2008124170 A2 | 10/2008 |
| WO | WO-2008144753 A2 | 11/2008 |
| WO | WO-2008124170 A3 | 12/2008 |
| WO | WO-2008149143 A2 | 12/2008 |
| WO | WO-2009021754 A2 | 2/2009 |
| WO | WO-2008149143 A3 | 4/2009 |
| WO | WO-2009046168 A1 | 4/2009 |
| WO | WO-2009064457 A2 | 5/2009 |
| WO | WO-2009064460 A2 | 5/2009 |
| WO | WO-2009068627 A2 | 6/2009 |
| WO | WO-2009147248 A2 | 12/2009 |
| WO | WO-2010020811 A1 | 2/2010 |
| WO | WO-2010045506 A2 | 4/2010 |
| WO | WO-2010056550 A1 | 5/2010 |
| WO | WO-2010045506 A3 | 7/2010 |
| WO | WO-2010077422 A2 | 7/2010 |
| WO | WO-2010085643 A1 | 7/2010 |
| WO | WO-2010115998 A2 | 10/2010 |
| WO | WO-2011009365 A1 | 1/2011 |
| WO | WO-2011083175 A1 | 7/2011 |
| WO | WO-2011094259 A2 | 8/2011 |
| WO | WO-2011098518 A2 | 8/2011 |
| WO | WO-2011104687 A1 | 9/2011 |
| WO | WO-2011112229 A2 | 9/2011 |
| WO | WO-2011135026 A1 | 11/2011 |
| WO | WO-2011135040 A1 | 11/2011 |
| WO | WO-2011139269 A1 | 11/2011 |
| WO | WO-2011139629 A2 | 11/2011 |
| WO | WO-2012007880 A2 | 1/2012 |
| WO | WO-2011139629 A3 | 4/2012 |
| WO | WO-2012055030 A1 | 5/2012 |
| WO | WO-2012078878 A2 | 6/2012 |
| WO | WO-2012130872 A1 | 10/2012 |
| WO | WO-2012131053 A1 | 10/2012 |
| WO | WO-2012151199 A1 | 11/2012 |
| WO | WO-2012175741 A2 | 12/2012 |
| WO | WO-2013024059 A2 | 2/2013 |
| WO | WO-2013056984 A1 | 4/2013 |
| WO | WO-2013058833 A1 | 4/2013 |
| WO | WO-2013064701 A2 | 5/2013 |
| WO | WO-2013087857 A2 | 6/2013 |
| WO | WO-2013087874 A1 | 6/2013 |
| WO | WO-2013091103 A1 | 6/2013 |
| WO | WO-2013173687 A1 | 11/2013 |
| WO | WO-2013184871 A1 | 12/2013 |
| WO | WO-2014030049 A2 | 2/2014 |
| WO | WO-2014058875 A3 | 6/2014 |
| WO | WO-2014141152 A2 | 9/2014 |
| WO | WO-2015009996 A1 | 1/2015 |
| WO | WO-2015058173 A1 | 4/2015 |
| WO | WO-2015065987 A1 | 5/2015 |
| WO | WO-2015100409 A2 | 7/2015 |
| WO | WO-2015144852 A1 | 10/2015 |
| WO | WO-2015176031 A2 | 11/2015 |
| WO | WO-2015189302 A1 | 12/2015 |
| WO | WO-2016065323 A2 | 4/2016 |
| WO | WO-2016103093 A1 | 6/2016 |
| WO | WO-2016156465 A1 | 10/2016 |
| WO | WO-2016156466 A1 | 10/2016 |
| WO | WO-2016162537 A1 | 10/2016 |
| WO | WO-2016202411 A1 | 12/2016 |
| WO | WO-2016202414 A1 | 12/2016 |
| WO | WO-2016202415 A1 | 12/2016 |
| WO | WO-2018104483 A1 | 6/2018 |
| WO | WO-2020254826 A1 | 12/2020 |
| WO | WO-2020254827 A1 | 12/2020 |
| WO | WO-2020254828 A1 | 12/2020 |

OTHER PUBLICATIONS

Baumgart et al.: Crohn's disease. Lancet 380(9853):1590-1605 (2012).

Bendig. Humanization of Rodent Monoclonal Antibodies by CDR Grafting. Methods a Companion to Methods In Enzymology 8:83-93 (1995).

Biancheri et al. Differential Cleavage of Anti-Tumor Necrosis Factor-Alpha Agents by Matrix Metalloproteinase (MMP)-10 and

(56) References Cited

OTHER PUBLICATIONS

MMP-12 In Inflammatory Bowel Disease. ECCO, Abstract, 1 page, Dublin (2011).
Biancheri et al.: Proteolytic cleavage and loss of function of biologic agents that neutralize tumor necrosis factor in the mucosa of patients with inflammatory bowel disease. Gastroenterology 149(6):1564-1574 (2015).
Binz et al.: Designing repeat proteins: well-expressed, soluble and stable proteins from combinatorial libraries of consensus ankyrin repeat proteins. J. Mol. Biology 332(2):489-503 (2003).
Bjerkan et al. Multiple Functions of the New Cytokine-Based Antimicrobial Peptide Thymic Stromal Lymphopoietin (TSLP). Pharmaceuticals (Basel) 9(3):E41 (2016).
Blattler et al. New heterobifunctional protein crosslinking reagent that forms an acid-labile link. Biochemistry 24(6):1517-1524 (1985).
Bruno et al.: Basics and recent advances in peptide and protein drug delivery. Ther Deliv. 4(11):1443-1467 (2013).
Caldas et al. Humanization of the anti-CD18 antibody 6.7: an unexpected effect of a framework residue in binding to antigen. Mol Immunol. 39(15):941-952 (2003).
Chen et al. Fusion Protein Linkers: Property, Design and Functionality. Adv Drug Deliv Rev 65:1357-1369 (2013). Available online Sep. 29, 2012.
Chomczynski, et al. Single-step method of RNA isolation by acid guanidinium thiocyanate-phenol-chloroform extraction. Anal Biochem. Apr. 1987;162(1):156-9.
Cianferoni et al. Eosinophilic Esophagitis and Gastroenteritis. Curr Allergy Asthma Rep. 15(9):58(2015).
Colman et al., Effects of amino acid sequence changes on antibody-antigen interactions, Research in Immunology, 1994; 145(1):33-36.
Colombel et al. Adalimumab for maintenance of clinical response and remission in patients with Crohn's disease: the Charm trial. Gastroenterology 132:52-65 (2007).
Coppieters et al.: Formatted anti-tumor necrosis factor alpha VHH proteins derived from camelids show superior potency and targeting to inflamed joints in a murine model of collagen-induced arthritis. Arthritis Rheum 54(6):1856-1866 (2006).
Corren et al. Tezepelumab in Adults with Uncontrolled Asthma. N Engl J Med. 377(10):936-946 (2017).
Crawley et al. Soluble IL-7R alpha (sCD127) inhibits IL-7 activity and is increased in HIV infection. J Immunol. 184(9):4679-4687 (2010).
Crowe et al.: Gastrointestinal Stability and Tissue Penetration of V565: a Novel Orally Administered Anti-TNFa VorabodyTM. Poster from 10th Annual Proteins and Antibodies Congress [1] (2017).
Crowe et al.: Gastrointestinal Stability and Tissue Penetration of V565: A Novel Orally Administered Anti-TNFa VorabodyTm. Vhsquared, Poster from PEGS Europe Protein and Antibody Engineering Summit, Lisbon, Portugal [1] (2017).
Crowe et al.: Oral Delivery of a Novel Engineered Anti TNFa Domain Antibody (VorabodyTM) for the Treatment of Intestinal Bowel Disease. PEGS Europe Protein & Antibody Engineering Summit [1] (2017).
Crowe et al.: Preclinical Assessment of a Novel Anti-TNFa VorabodyTM as an Oral Therapy for Crohn's Disease. 18th International Congress of Mucosal Immunology, Washington D.C. [1] (2017).
Crowe et al.: Preclinical Development of a Novel, Orally-Administered Anti-Tumour Necrosis Factor Domain Antibody for the Treatment of Inflammatory Bowel Disease. Scientific Reports 8:4941 [1-13] (2018).
Croxford et al. IL-23: one cytokine in control of autoimmunity. Eur J Immunol. 42:2263-2273 (2012).
Danese: New therapies for inflammatory bowel disease: from the bench to the bedside. Gut 61(6):918-932 (2012).
Deschacht et al.: A novel promiscuous class of camelid single-domain antibody contributes to the antigen-binding repertoire. J. Immmunol 184(10):5696-5704 (2010).
Desmet et al. Structural basis of IL-23 antagonism by an Alphabody protein scaffold. Nature Communications 5:5237 (2014).

Desmyter et al.: Neutralization of Human Interleukin 23 by Multivalent Nanobodies Explained by the Structure of Cytokine-Nanobody Complex. Front Immunol. 8:884 (2017).
Dooms. Interleukin-7: Fuel for the autoimmune attack. J Autoimmun. 45:40-48 (2013).
Ebersbach et al.: Affilin-novel binding molecules based on human gamma-B-crystallin, an all beta-sheet protein. J. Molecular Biology 372(1):172-185 (2007).
Eken et al. Interleukin 23 in Crohn's disease. Inflamm Bowel Dis. 20:587-595 (2014).
Ellis et al. Anti-IL-7 receptor a monoclonal antibody (GSK2618960) in healthy subjects—a randomized, double-blind, placebo-controlled study. Br J Clin Pharmacol. 85(2):304-315 (2019).
Fadda et al.: Physiological bicarbonate buffers: stabilisation and use as dissolution media for modified release systems. Int. J. Pharm. 382(1-2):56-60 (2009).
Faisst et al.: Isolation of a fully infectious variant of parvovirus H-1 supplanting the standard strain in human cells. Journal of Virology 69(7):4538-4543 (1995).
Fields et al. Dual-attribute continuous monitoring of cell proliferation/cytotoxicity. Am Biotechnol Lab 11(4):48-50 (1993).
Fornasa et al. Dichotomy of short and long thymic stromal lymphopoietin isoforms in inflammatory disorders of the bowel and skin. J Allergy Clin Immunol. 136(2):413-422 (2015).
Frenken et al. Isolation of antigen specific llama VHH antibody fragments and their high level secretion by *Saccharomyces cerevisiae*. J Biotechnol 78(1):11-21 (2000).
Fry et al. Interleukin-7: from bench to clinic. Blood 99(11):3892-3904 (2002).
Fry et al. The many faces of IL-7: from lymphopoiesis to peripheral T cell maintenance. J Immunol. 174(11):6571-6576 (2005).
Furfaro et al. IL-23 Blockade for Crohn s disease: next generation of anti-cytokine therapy. Expert Rev Clin Immunol. 13:457-467 (2017).
Garbacz et al.: A dynamic system for the simulation of fasting luminal pH-gradients using hydrogen carbonate buffers for dissolution testing of ionisable compounds. Eur J Pharm Sci. 51:224-231 (2014).
Giusti et al. Somatic diversification of S107 from an antiphosphocholineto an anti-DNA autoantibody is due to a single base change in its heavy chain variable region. PNAS USA 84(9):2926-30 (1987).
Goldberg et al.: Engineering a targeted delivery platform using Centyrins. Protein Eng Des Sei. 29(12):563-572 (2016).
Goldberg et al. The unusual suspects—innate lymphoid cells as novel therapeutic targets in IBD. Nat Rev Gastroenterol Hepatol (5):271-283 (2015).
Gomes et al., Comparison of yeasts as hosts for recombinant protein production. Microorganisms 6(2):38 [1-23] (2018).
Goyanes et al.: Gastrointestinal release behaviour of modified-release drug products: dynamic dissolution testing of mesalazine formulations. Int. J. Pharm. 484(1-2):103-108 (2015).
Grabulovski et al. A novel, non-immunogenic Fyn SH3-derived binding protein with tumor vascular targeting properties. J Biol Chem. 282(5):3196-3204 (2007).
Griffiths et al.: Shark Variable New Antigen Receptor (VNAR) Single Domain Antibody Fragments: Stability and Diagnostic Applications. Antibodies 2(1):66-81 (2013).
Grundstrom et al.: Oligonucleotide-directed mutagenesis by microscale 'shot-gun' gene synthesis. Nucleic Acids Research 13(9):3305-3316 (1985).
Guerra et al.: Management of inflammatory bowel disease in poor responders to infliximab. Clin Exp Gastroenterol 7:359-367 (2014).
Hafler et al. Risk alleles for multiple sclerosis identified by a genomewide study. N Engl J Med. 357(9):851-862 (2007).
Hamers-Casterman et al. Naturally occurring antibodies devoid of light chains. Nature 363(6428):446-8 (1993).
Hanauer et al. Human anti-tumor necrosis factor monoclonal antibody (adalimumab) in Crohn's disease: the Classic-I trial. Gastroenterology 130:323-333 (2006).
Hanauer et al., Maintenance infliximab for Crohn's disease: the Accent I randomized trial. Lancet 359:1541-1549 (2002).

(56) References Cited

OTHER PUBLICATIONS

Harmsen et al.: Effect of a pmr 1 disruption and different signal sequences on the intracellular processing and secretion of Cyamopsis tetragonoloba alpha-galactosidase by *Saccharomyces cerevisiae*. Gene 125(2):115-123 (1993).
Harmsen et al. Properties, production, and applications of camelid single-domain antibody fragments. Appl. Microbiol. Biotechnol. 77:13-22 (2007).
Harmsen et al.: Selection and Optimization of Proteolytically Stable Llama Single-Domain Antibody Fragments for Oral Immunotherapy. Applied Microbiology and Biotechnology 72(3):544-551 (2006).
Hashimoto et al.: Effects of signal sequences on the secretion of hen lysozyme by yeast: construction of four secretion cassette vectors. Protein Engineering 11(2):75-77 (1998).
Hendrickson et al.: Clinical aspects and pathophysiology of inflammatory bowel disease. Clinical Microbiology Reviews 15(1):79-94 (2002).
Henikoff et al. Amino acid substitution matrices from protein blocks. PNAS USA 89(22):10915-10919 (1992) .
Heninger et al. IL-7 abrogates suppressive activity of human CD4+CD25+FOXP3+ regulatory T cells and allows expansion of alloreactive and autoreactive T cells. J Immunol. 189(12):5649-5658 (2012).
Hoefman et al.: Pre-Clinical Intravenous Serum Pharmacokinetics of Albumin Binding and Non-Half-Life Extended Nanobodies(R). Antibodies 4(3):141-156 (2015).
Hoogenboom et al. Multi-subunit proteins on the surface of filamentous phage: methodologies for displaying antibody (Fab) heavy and light chains. Nucleic Acids Res. 19(15):4133-4137 (1991).
Horwitz et al.: Secretion of functional antibody and Fab fragment from yeast cells. Proc. Natl. Acad. Sci. U.S.A. 85(22):8678-8682 (1988).
Hu et al., A phylogenomic approach to reconstructing the diversification of serine proteases in fungi. J Evol Biol. 17(6):1204-1214 (2004).
Humphreys et al.: Modes of L929 cell death induced by TNF-alpha and other cytotoxic agents. Cytokine 11(10):773-782 (1999).
Huse et al. Generation of a large combinatorial library of the immunoglobulin repertoire in phage lambda. Science 246(4935):1275-1281 (1989).
Hussack et al: A V(L) single-domain antibody library shows a high-propensity to yield non-aggregating binders. Protein Eng Des Sei. 25(6):313-318 (2012).
Hussack et al. Chapter 14: Isolation and characterization of Clostridium difficile toxin-specific single-domain antibodies. Methods Mol Biol. 911:211-239 (2012).
Hussack et al. Engineered Single-Domain Antibodies with High Protease Resistance and Thermal Stability. PLoS One. 6(11):e28218 (2011).
Hussack et al.: Neutralization of Clostridium difficile toxin A with single-domain antibodies targeting the cell receptor binding domain. J. Biol. Chem. 286(11):8961-8976 (2011).
Hussack et al.: Protease-resistant single-domain antibodies inhibit Campylobacter jejuni motility. Protein Eng Des Sei. 27(6):191-198 (2014).
Hussack et al.: Single-domain Antibody Inhibitors of Clostridium difficile Toxins. Thesis submitted to the Faculty of Graduate and Postdoctoral Studies, Dept. of Biochemistry, Microbiology and Immunology [1-227] (2011).
Hussack: Single-domain Antibody Inhibitors of Clostridium difficule Toxins. Universite d'Ottawa website [1-3] https://ruor.uottawa.ca/handle/10393/20362 (2013).
Hussan et al. A review on recent advances of enteric coating. IOSR J Pharm 2(6):5-11 (2012).
Johnson et al.: Sensitive affimer and antibody based impedimetric label-free assays for c-reactive protein. Analytical Chemistry 84(15):6553-6560 (2012).
Jones et al.: Targeted localized use of therapeutic antibodies: a review of non-systemic, topical and oral applications. Crit Rev Biotechnol 36(3):506-520 (2015).
Kabat et al. Sequences of proteins of immunological interest. NIH Publ. No. 91-3242 1:647-669 (1991).
Kamm et al.: Practical application of anti-TNF therapy for luminal Crohn's disease. Inflammatory Bowel Diseases. 17(11):2366-2391 (2011).
Karlin, et al. Applications and statistics for multiple high-scoring segments in molecular sequences. PNAS USA 90:5873-5877 (1993).
Khantasup et al. Design and Generation of Humanized Single-chain Fv Derived from Mouse Hybridoma for Potential Targeting Application. Monoclon Antib Immunodiagn Immunother. 34(6):404-17 (2015).
Kim et al. A Dual Target-directed Agent against Interleukin-6 Receptor and Tumor Necrosis Factor a ameliorates experimental arthritis. Scientific Reports 6:20150 (2015).
Kim et al.: Antibody light chain variable domains and their biophysically improved versions for human immunotherapy. Mabs. 6(1):219-235 (2014).
Knezevic et al. Quantitation of affinity, avidity, and binding kinetics of protein analytes with a dynamically switchable biosurface. J Am Chem Soc 134(37):15225-15228 (2012).
Kohler et al. Continuous cultures of fused cells secreting antibody of predefined specificity. Nature256(5517):495-497 (1975).
Koide et al. Monobodies: antibody mimics based on the scaffold of the fibronectin type III domain. Methods in Molecular Biology 352:95-111 (2007).
Krehenbrink et al.: Artificial binding proteins (Affitins) as probes for conformational changes in secretin PuID. J Mol Biol. 383(5):1058-1068 (2008).
Ling et al.: Approaches to DNA Mutagenesis: An Overview. Analytical Biochemistry 254(2):157-178 (1997).
Lipovsek: Adnectins: engineered target-binding protein therapeutics. Protein Engineering, Design & Selection 24(1-2):3-9 (2011).
Liu et al. Crucial role of interleukin-7 in T helper type 17 survival and expansion in autoimmune disease. Nat Med. 16(2):191-197 (2010) (retraction in: Nat Med. 2013 19(12):1673).
Liu et al.: Targeting TNF-alpha with a tetravalent mini-antibody TNF-TeAb. Biochemical Journal 406(2):237-246 (2007).
Liu. Thymic stromal lymphopoietin: master switch for allergic inflammation. J Exp Med 203(2):269-273 (2006).
Lopes et al.: Mechanism of high-copy-number integration of pMIRY-type vectors into the ribosomal DNA of *Saccharomyces cerevisiae*. Gene. 105(1):83-90 (1991).
McCoy et al.: Neutralisation of HIV-1 cell-cell spread by human and llama antibodies. Retrovirology 11:83 doi:10.1186/s12977-014-0083-y [1-15] (2014).
McGovern et al. The IL23 axis plays a key role in the pathogenesis of IBD. Gut 56:1333-1336 (2007).
Merchant et al.: Predicting the gastrointestinal behaviour of modified-release products: utility of a novel dynamic dissolution test apparatus involving the use of bicarbonate buffers. Int. J. Pharm. 475(1-2):585-591 (2014).
Merchlinksy et al.: Construction of an infectious molecular clone of the autonomous parvovirus minute virus of mice. Journal of Virology 47(1):227-232 (1983).
Michael. The role of digestive enzymes in orally induced immune tolerance. Immunol Invest. 18(9-10):1049-1054 (1989) (Abstract).
Miethe et al.: Production of Single Chain Fragment Variable (scFv) Antibodies in *Escherichia coli* Using the LEX TM Bioreactor. Journal of Biotechnology 163(2):105-111 (2012).
Molhoj et al. CD19-/CD3-bispecific antibody of the BiTE class is far superior to tandem diabody with respect to redirected tumor cell lysis. Mol Immunol. 44(8):1935-43 (2007).
Muszewska et al., Fungal lifestyle reflected in serine protease repertoire. Sci Rep. 7(1):9147 [1-12] (2017).
Muyldermans. Nanobodies: natural single-domain antibodies. Annu Rev Biochem 82:775-797 (2013).
Muyldermans et al. Sequence and structure of VH domain from naturally occurring camel heavy chain immunoglobulins lacking light chains. Protein Engineering 7(9):1129-1133 (1994).
Nambiar, et al. Total synthesis and cloning of a gene coding for the ribonuclease S protein. Science 223(4642):1299-301 (1984).
Nelson et al.: Nonoclonal antibodies. Molecular Pathology 53(3):111-117 (2000).

(56) References Cited

OTHER PUBLICATIONS

Nguyen et al. Functional heavy-chain antibodies in Camelidae. Adv Immunol 79:261-296 (2001).
Nixon et al. Engineered protein inhibitors of proteases. Curr Opin Drug Discov Devel. 9(2):261-268 (2006).
Nogi et al.: Nucleotide sequence of the transcriptional initiation region of the yeast GAL7 gene. Nucleic Acid Research 11(24):8555-8568 (1983).
Noti et al. Thymic stromal lymphopoietin-elicited basophil responses promote eosinophilic esophagitis. Nat Med. 19(8):1005-1013 (2013).
Nurbhai et al.: Measured and Modelled Data Suggest That Oral Administration of V565, a Novel Domain Antibody to TNF-alpha, Could be Beneficial in the Treatment of IBD. 13th Congress of ECCO, Vienna, Austria, 1 page (2018).
Nurbhai et al.: Oral Anti-Tumour Necrosis Factor Domain Antibody V565 Provides High Intestinal Concentrations, and Reduces Markers of Inflammation in Ulcerative Colitis Patients. Sci Rep. 9(1):14042 (2019).
Nygren. Alternative binding proteins: affibody binding proteins developed from a small three-helix bundle scaffold. FEBS J. 275(11):2668-2676 (2008).
Ordas et al.: Anti-TNF monoclonal antibodies in inflammatory bowel disease: pharmacokinetics-based dosing paradigms. Clin Pharmacol Ther. 91(4):635-646 (2012).
Ortonne. Recent developments in the understanding of the pathogenesis of psoriasis. British Journal of Dermatology 140(Suppl 54):1-7 (1999).
Padlan. Anatomy of the Antibody Molecule. Mol Immunol 31(3):169-217 (1994).
Patnaik et al. Penicillin fermentation: mechanisms and models for industrial-scale bioreactors. Crit Rev Biotechnol 20:1-15 (2015).
Paul. Fundamental Immunology. 3rd Edition, pp. 292-295, Raven Press (1993).
PCT/EP2016/057021 International Search Report and Written Opinion dated Aug. 8, 2016.
PCT/EP2016/057022 International Search Report and Written Opinion dated Jun. 14, 2016.
PCT/EP2016/057024 International Search Report and Written Opinion dated Jun. 16, 2016.
PCT/EP2016/057032 International Search Report and Written Opinion dated Aug. 4, 2016.
PCT/EP2016/057034 International Search Report and Written Opinion dated Aug. 3, 2016.
PCT/EP2017/057775 International Search Report and Written Opinion dated Jul. 7, 2017.
PCT/GB2020/051495 International Search Report and Written Opinion dated Sep. 30, 2020.
PCT/GB2020/051496 International Search Report and Written Opinion dated Oct. 20, 2020.
PCT/GB2020/051497 International Search Report and Written Opinion dated Sep. 17, 2020.
PCT/MT2017/000001 International Search Report and Written Opinion dated Oct. 20, 2017.
Peters et al. Innate lymphoid cells in inflammatory bowel diseases. Immunol Lett. 172:124-131 (2015).
Rimoldi et al. Intestinal immune homeostasis is regulated by the crosstalk between epithelial cells and dendritic cells. Nat Immunol. 6(5):507-514 (2005).
Robinson et al.: A Protease-Resistant Oral Domain Antibody to TNFα Delivers High Concentrations of Active Compound in Ileal Fluid of Subjects with an Ileostomy. 25th United European Gastroenterology Week, Barcelona, Spain [1] (2017).
Rose et al. Identification and biochemical characterization of human plasma soluble IL-7R: lower concentrations in HIV-1-infected patients. J Immunol. 182(12):7389-7397 (2009).
Rose-John: IL-6 trans-signaling via the soluble IL-6 receptor: importance for the pro-inflammatory activities of IL-6. Int. J. Biol. Sci. 8(9):1237-1247 (2012).
Roux et al.: Structural analysis of the nurse shark (new) antigen receptor (NAR): molecular convergence of NAR and unusual mammalian immunoglobulins. PNAS USA 95(20):11804-11809 (1998).
Rudikoff et al. Single amino acid substitution altering antigen-binding Specificity. PNAS USA 79:1979-1983 (1982).
Saerens et al. Identification of a universal VHH framework to graft non-canonical antigen-binding loops of camel single-domain antibodies. J Mol Biol. 352(3):597-607 (2005).
Sakmar et al.: Total synthesis and expression of a gene for the alpha-subunit of bovine rod outer segment guanine nucleotide-binding protein (transducin). Nucleic Acids Research 16(14A):6361-6372 (1988).
Sandborn et al. Certolizumab pegol for the treatment of Crohn's disease. N Engl J Med. 357:228-238 (2007).
Schreiber et al. Maintenance therapy with certolizumab pegol for Crohn's disease. N Engl J Med. 357:239-250 (2007).
Shaji, et al. Protein and Peptide drug delivery: oral approaches. Indian J Pharm Sci. May-Jun. 70(3):269-77 (2008).
Shealy et al.: Characterization of golimumab, a human monoclonal antibody specific for human tumor necrosis factor a. MAbs 2(4):428-439 (2010).
Silverman et al., Multivalent avimer proteins evolved by exon shuffling of a family of human receptor domains. Nat. Biotechnol. 23 (12):1556-1561 (2005).
Siontorou: Nanobodies as novel agents for disease diagnosis and therapy. Int J Nanomedicine 8:4215-4227 (2013).
Skerra: Alternative binding proteins: anticalins—harnessing the structural plasticity of the lipocalin ligand pocket to engineer novel binding activities. FEBS J. 275(11):2677-2683 (2008).
Skerra et al. Assembly of a functional Immunoglobulin Fv fragment in *Escherichia coli*. Science 240(4855):1038-1041 (1988).
STIC report (2019).
Suderman et al.: Development of polyol-responsive antibody mimetics for single-step protein purification. Protein Expr Purif. 134:114-124 (2017).
Tal et al.: Interleukin 7 and thymic stromal lymphopoietin: from immunity to leukemia. Cell Mol Life Sci. 71(3):365-378 (2014).
Tanha et al.: Selection by phage display of llama conventional V(H) fragments with heavy chain antibody V(H)H properties. Journal of Immunological Methods 263(1-2):97-109 (2002).
Teng et al. IL-12 and IL-23 cytokines: from discovery to targeted therapies for immune-mediated inflammatory diseases. Nat Med. 21:719-729 (2015).
Teutsch et al. Identification of 11 novel and common single nucleotide polymorphisms in the interleukin-7 receptor-alpha gene and their associations with multiple sclerosis. Eur J Hum Genet. 11(7):509-515 (2003).
Thomassen et al.: Large-scale production of VHH antibody fragments by *Saccharomyces cerevisiae*. Enzyme and Microbial Technology 30(3):273-278 (2002).
Tsilingiri et al. Thymic Stromal Lymphopoietin: To Cut a Long Story Short. Cell Mol Gastroenterol Hepatol. 3(2):174-182 (2017).
Ungar et al.: Optimizing Anti-TNF-a Therapy: Serum Levels of Infliximab and Adalimumab are Associated With Mucosal Healing in Patients With Inflammatory Bowel Diseases. Clin Gastroenterol Hepatol. 14(4):550-557 (2016).
Unger et al.: Selection of nanobodies that block the enzymatic and cytotoxic activities of the binary Clostridium difficile toxin CDT. Scientific Reports 5:7850 [1-10] (2015).
UniProt Database: Uncharacterized protein. Accession No. B5H131, 2 pages (2008) http://www.uniprot.org/uniprot/B5H131.
U.S. Appl. No. 15/273,353 Office Action dated Aug. 16, 2018.
U.S. Appl. No. 15/273,353 Office Action dated Jan. 23, 2018.
U.S. Appl. No. 15/273,353 Office Action dated Jun. 4, 2019.
U.S. Appl. No. 15/717,174 Office Action dated Apr. 22, 2020.
U.S. Appl. No. 15/717,174 Office Action dated Aug. 8, 2019.
U.S. Appl. No. 15/717,174 Office Action dated Mar. 6, 2019.
U.S. Appl. No. 15/717,174 Office Action dated Sep. 16, 2020.
U.S. Appl. No. 15/717,230 Office Action dated Jan. 21, 2020.
U.S. Appl. No. 15/717,230 Office Action dated May 18, 2020.
U.S. Appl. No. 15/717,230 Office Action dated Sep. 3, 2019.
U.S. Appl. No. 16/140,843 Office Action dated Nov. 26, 2019.

(56) References Cited

OTHER PUBLICATIONS

U.S. Appl. No. 16/988,506 Office Action dated Oct. 6, 2020.
Van Schie et al.: The antibody response against human and chimeric anti-TNF therapeutic antibodies primarily targets the TNF binding region. Ann Rheum Dis. 74(1):311-314 (2015).
Vandenbroucke et al. Orally administered *L. lactis* secreting an anti-TNF nanobody demonstrate efficacy in chronic colitis. Mucosal Immunology 3(1):49-56 (2010).
Vandeventer: Anti-TNF antibody treatment of Crohn's disease. Ann Rheum Dis. 58(Suppl I):I114-I120 (1999).
Verma et al. Modified oligonucleotides: synthesis and strategy for users. Annu Rev Biochem 67:99-134 (1998).
Verstraete et al. Structure and antagonism of the receptor complex mediated by human TSLP in allergy and asthma. Nat Commun. 8:14937 (2017).
Vetter et al. Emerging oral targeted therapies in inflammatory bowel diseases: opportunities and challenges. Therap Adv Gastroenterol. 10(10):773-790 (2017).
Vincke et al. General strategy to humanize a camelid single-domain antibody and identification of a universal humanized nanobody scaffold. J. Biol. Chem. 284(5):3273-3284 (2009).
Volkel et al.: Optimized linker sequences for the expression of monomeric and dimeric bispecific single-chain diabodies. Protein Eng. 14(10):815-823 (2001).
Vossenkamper et al.: A CD3-specific antibody reduces cytokine production and alters phosphoprotein profiles in intestinal tissues from patients with inflammatory bowel disease. Gastroenterology 147(1):172-183 (2014).
Vu et al.: Comparison of llama VH sequences from conventional and heavy chain antibodies. Molecular Immunology 34(16-17):1121-1131 (1997).
Wahlich et al.: Oral Delivery of a Novel Domain Antibody (VorabodyTM) for the Treatment of Chron's Disease. PEGS Europe Protein & Antibody Engineering Summit, Lisbon, Portugal, 1 page (2017).
Walsh. Structural insights into the common γ-chain family of cytokines and receptors from the interleukin-7 pathway. Immunol Rev. 250(1):303-316 (2012).
Ward et al. Binding activities of a repertoire of single immunoglobulin variable domains secreted from *Escherichia coli*. Nature 341(6242):544-546 (1989).
Wells et al. Cassette mutagenesis: an efficient method for generation of multiple mutations at defined sites. Gene 34:315-323 (1985).
West et al.: Predicting intestinal tract luminal concentrations after oral dosing of an anti-TNFa domain antibody engineered for intestinal protease resistance. VHsquared Antibody Engineering & Therapeutics Meeting, San Diego, USA, 1 page (2017).
Winkler et al. Changing the antigen binding specificity by single point mutations of an anti-p24 (HIV-1) antibody. J Immunol. 165(8):4505-4514 (2000).
Yan et al. Construction of a synthetic phage-displayed Nanobody library with CDR3 regions randomized by trinucleotide cassettes for diagnostic applications. Journal of Translational Medicine 12:343 (2014).
Yu et al., Interaction between Bevacizumab and Murine VEGF-A: A Reassessment. Investigative Ophthalmology & Visual Science 49(2):522-527 (2008).
Zabetakis et al. Contributions of the complementarity determining regions to the thermal stability of a single-domain antibody. PLoS One 8(10):e77678 (2013).
Casset et al. A peptide mimetic of an anti-CD4 monoclonal antibody by rational design. Biochemical and Biophysical Research Communication 307:198-205 (2003).
Chen et al. Enhancement and destruction of antibody function U by somatic mutation: unequal occurrence is controlled by V gene combinatorial associations. The EMBO Journal 14(12):2784-2794 (1995).
MacCallum et al.: Antibody-antigen interactions: contact analysis and binding site topography. J Mol Biol. 262(5):732-745 (1996).
U.S. Appl. No. 16/821,287 Office Action dated Oct. 21, 2022.
U.S. Appl. No. 17/752,710 Office Action dated Nov. 4, 2022.

Figure 8

SEQ ID NO: 8

SEQUENCE LISTING

```
<160> NUMBER OF SEQ ID NOS: 77

<210> SEQ ID NO 1
<211> LENGTH: 5
<212> TYPE: PRT
<213> ORGANISM: Lama glama

<400> SEQUENCE: 1

Phe Lys Val Met Gly
1               5

<210> SEQ ID NO 2
<211> LENGTH: 16
<212> TYPE: PRT
<213> ORGANISM: Lama glama

<400> SEQUENCE: 2

Thr Ile Thr Thr Gly Gly Ser Pro Asp Tyr Ser Asp Ser Val Lys Gly
```

<210> SEQ ID NO 3
<211> LENGTH: 13
<212> TYPE: PRT
<213> ORGANISM: Lama glama

<400> SEQUENCE: 3

```
Arg Leu Trp Ala His Ile Thr Ser Ser Gly His Asp Val
1               5                   10
```

<210> SEQ ID NO 4
<211> LENGTH: 30
<212> TYPE: PRT
<213> ORGANISM: Lama glama

<400> SEQUENCE: 4

```
Asp Val Gln Leu Val Glu Ser Gly Gly Gly Val Gln Pro Gly Gly
1               5                   10                  15

Ser Leu Ser Leu Ser Cys Glu Ser Val Ser Ile Trp Ser
                20                  25                  30
```

<210> SEQ ID NO 5
<211> LENGTH: 14
<212> TYPE: PRT
<213> ORGANISM: Lama glama

<400> SEQUENCE: 5

```
Trp Phe Arg Gln Val Pro Gly Lys Gln Arg Glu Leu Val Ala
1               5                   10
```

<210> SEQ ID NO 6
<211> LENGTH: 32
<212> TYPE: PRT
<213> ORGANISM: Lama glama

<400> SEQUENCE: 6

```
Arg Phe Thr Ile Ser Arg Asp Tyr Asp Lys Arg Thr Leu Tyr Leu Gln
1               5                   10                  15

Met Asn Ser Leu Lys Arg Ala Asp Thr Ala Val Tyr Tyr Cys Ala Gly
                20                  25                  30
```

<210> SEQ ID NO 7
<211> LENGTH: 11
<212> TYPE: PRT
<213> ORGANISM: Lama glama

<400> SEQUENCE: 7

```
Trp Gly Gln Gly Thr Gln Val Thr Val Ser Ser
1               5                   10
```

<210> SEQ ID NO 8
<211> LENGTH: 121
<212> TYPE: PRT
<213> ORGANISM: Lama glama

<400> SEQUENCE: 8

```
Asp Val Gln Leu Val Glu Ser Gly Gly Gly Val Gln Pro Gly Gly
1               5                   10                  15

Ser Leu Ser Leu Ser Cys Glu Ser Val Ser Ile Trp Ser Phe Lys
                20                  25                  30

Val Met Gly Trp Phe Arg Gln Val Pro Gly Lys Gln Arg Glu Leu Val
        35                  40                  45
```

Ala Thr Ile Thr Thr Gly Gly Ser Pro Asp Tyr Ser Asp Ser Val Lys
            50                  55                  60

Gly Arg Phe Thr Ile Ser Arg Asp Tyr Asp Lys Arg Thr Leu Tyr Leu
 65                  70                  75                  80

Gln Met Asn Ser Leu Lys Pro Glu Asp Thr Ala Val Tyr Tyr Cys Ala
                 85                  90                  95

Gly Arg Leu Trp Ala His Ile Thr Ser Ser Gly His Asp Val Trp Gly
            100                 105                 110

Gln Gly Thr Gln Val Thr Val Ser Ser
            115                 120

<210> SEQ ID NO 9
<211> LENGTH: 369
<212> TYPE: DNA
<213> ORGANISM: Lama glama

<400> SEQUENCE: 9
gatgttcaat tggttgaatc tggtggtggt caagttcaac caggtggttc tttgtcttta      60
tcttgtgaat cctccgtttc catctggtct tttaaagtta tgggttggtt cagacaagtc     120
ccaggtaaac aaagagaatt ggttgctact attactaccg gtggttctcc agattattcc     180
gattctgtta agggtagatt caccatctca agagattacg ataagaggac cttgtacttg     240
cagatgaatt ctttgaagcc agaagatacc gctgtttatt actgtgctgg tagattgtgg     300
gctcatatta cttcatctgg tcatgatgtt tggggtcaag gtactcaagt tactgtctct     360
tcatgataa                                                              369

<210> SEQ ID NO 10
<211> LENGTH: 363
<212> TYPE: DNA
<213> ORGANISM: Lama glama

<400> SEQUENCE: 10
gatgttcaat tggttgaatc tggtggtggt caagttcaac caggtggttc tttgtcttta      60
tcttgtgaat cctccgtttc catctggtct tttaaagtta tgggttggtt cagacaagtc     120
ccaggtaaac aaagagaatt ggttgctact attactaccg gtggttctcc agattattcc     180
gattctgtta agggtagatt caccatctca agagattacg ataagaggac cttgtacttg     240
cagatgaatt ctttgaagcc agaagatacc gctgtttatt actgtgctgg tagattgtgg     300
gctcatatta cttcatctgg tcatgatgtt tggggtcaag gtactcaagt tactgtctct     360
tca                                                                    363

<210> SEQ ID NO 11
<211> LENGTH: 121
<212> TYPE: PRT
<213> ORGANISM: Lama glama

<400> SEQUENCE: 11

Glu Val Gln Leu Val Glu Ser Gly Gly Gly Leu Val Gln Pro Gly Gly
 1               5                  10                  15

Ser Leu Arg Leu Ser Cys Ala Ala Ser Val Ser Ile Trp Ser Phe Lys
            20                  25                  30

Val Met Gly Trp Tyr Arg Gln Val Pro Gly Lys Gln Arg Glu Leu Val
            35                  40                  45

Ala Thr Ile Thr Thr Gly Gly Ser Pro Asp Tyr Ala Asp Ser Val Lys
            50                  55                  60

-continued

Gly Arg Phe Thr Met Ser Arg Asp Tyr Asp Lys Arg Thr Val Phe Leu
65                  70                  75                  80

Glu Met Asp Ser Val Lys Pro Glu Asp Ala Ala Val Tyr Tyr Cys Asn
            85                  90                  95

Gly Arg Leu Trp Ala His Leu Thr Ser Ser Gly His Asp Val Trp Gly
        100                 105                 110

Gln Gly Thr Arg Val Thr Val Ser Ser
        115                 120

<210> SEQ ID NO 12
<211> LENGTH: 121
<212> TYPE: PRT
<213> ORGANISM: Lama glama

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Val Ser Ile Trp Ser Phe Lys
            20                  25                  30

Val Met Gly Trp Tyr Arg Gln Val Pro Gly Lys Gln Arg Glu Leu Val
        35                  40                  45

Ala Thr Ile Thr Thr Gly Gly Ser Pro Asp Tyr Ala Asp Ser Val Lys
    50                  55                  60

Gly Arg Phe Thr Met Ser Arg Asp Tyr Asp Lys Arg Thr Val Phe Leu
65                  70                  75                  80

Glu Met Asp Ser Val Lys Pro Glu Asp Ala Ala Val Tyr Tyr Cys Asn
            85                  90                  95

Gly Arg Leu Trp Ala His Leu Thr Ser Ser Gly His Asp Val Trp Gly
        100                 105                 110

Gln Gly Thr Gln Val Thr Val Ser Ser
        115                 120

<210> SEQ ID NO 13
<211> LENGTH: 126
<212> TYPE: PRT
<213> ORGANISM: Lama glama

<400> SEQUENCE: 13

Glu Val Gln Leu Val Glu Ser Gly Gly Gly Leu Ala Gln Ala Gly Gly
1               5                   10                  15

Ser Leu Arg Leu Ser Cys Ala Pro Ser Gly Arg Ala Phe Ser Gly Ser
            20                  25                  30

Ala Met Gly Trp Phe Arg Gln Val Pro Gly Lys Glu Arg Glu Phe Val
        35                  40                  45

Gly Val Ile Ile Trp Thr Gly Tyr Thr Tyr Tyr Ala Asp Ser Val
    50                  55                  60

Lys Gly Arg Phe Thr Ile Ser Arg Asp Ser Ala Lys Asn Thr Val Tyr
65                  70                  75                  80

Leu Gln Met Asp Ser Leu Lys Pro Glu Asp Thr Ala Val Tyr Tyr Cys
            85                  90                  95

Ala Ala Arg Thr Pro Asn Ser Ser Trp Phe Pro Thr Thr Leu Tyr Glu
        100                 105                 110

Tyr Asp Tyr Trp Gly Gln Gly Thr Gln Val Thr Val Ser Ser
        115                 120                 125

<210> SEQ ID NO 14

```
<211> LENGTH: 5
<212> TYPE: PRT
<213> ORGANISM: Lama glama

<400> SEQUENCE: 14

Gly Ser Ala Met Gly
1               5

<210> SEQ ID NO 15
<211> LENGTH: 17
<212> TYPE: PRT
<213> ORGANISM: Lama glama

<400> SEQUENCE: 15

Val Ile Ile Trp Thr Gly Gly Tyr Thr Tyr Tyr Ala Asp Ser Val Lys
1               5                   10                  15

Gly

<210> SEQ ID NO 16
<211> LENGTH: 17
<212> TYPE: PRT
<213> ORGANISM: Lama glama

<400> SEQUENCE: 16

Arg Thr Pro Asn Ser Ser Trp Phe Pro Thr Thr Leu Tyr Glu Tyr Asp
1               5                   10                  15

Tyr

<210> SEQ ID NO 17
<211> LENGTH: 30
<212> TYPE: PRT
<213> ORGANISM: Lama glama

<400> SEQUENCE: 17

Glu Val Gln Leu Val Glu Ser Gly Gly Gly Leu Ala Gln Ala Gly Gly
1               5                   10                  15

Ser Leu Arg Leu Ser Cys Ala Pro Ser Gly Arg Ala Phe Ser
            20                  25                  30

<210> SEQ ID NO 18
<211> LENGTH: 14
<212> TYPE: PRT
<213> ORGANISM: Lama glama

<400> SEQUENCE: 18

Trp Phe Arg Gln Val Pro Gly Lys Glu Arg Glu Phe Val Gly
1               5                   10

<210> SEQ ID NO 19
<211> LENGTH: 32
<212> TYPE: PRT
<213> ORGANISM: Lama glama

<400> SEQUENCE: 19

Arg Phe Thr Ile Ser Arg Asp Ser Ala Lys Asn Thr Val Tyr Leu Gln
1               5                   10                  15

Met Asp Ser Leu Lys Pro Glu Asp Thr Ala Val Tyr Tyr Cys Ala Ala
            20                  25                  30

<210> SEQ ID NO 20
<211> LENGTH: 11
<212> TYPE: PRT
<213> ORGANISM: Lama glama
```

<400> SEQUENCE: 20

Trp Gly Gln Gly Thr Gln Val Thr Val Ser Ser
1               5                   10

<210> SEQ ID NO 21
<211> LENGTH: 124
<212> TYPE: PRT
<213> ORGANISM: Lama glama

<400> SEQUENCE: 21

Glu Val Gln Leu Val Glu Ser Gly Gly Gly Leu Val Gln Ala Gly Thr
1               5                   10                  15

Ser Leu Arg Leu Ser Cys Ala Ala Ser Gly Arg Thr Phe Ser Asn Tyr
            20                  25                  30

Ile Met Gly Trp Phe Arg Gln Ala Pro Gly Lys Glu Arg Glu Phe Val
        35                  40                  45

Ala Ile Ile Thr Ala Asn Gly Val Ala Thr Asp Tyr Arg Asp Ser Val
    50                  55                  60

Lys Gly Arg Phe Thr Ile Ser Arg Asp Asn Ala Arg Asn Thr Gly Tyr
65                  70                  75                  80

Leu Glu Met Asn Ser Leu Lys Pro Glu Asp Thr Ala Val Tyr Phe Cys
                85                  90                  95

Ala Leu Arg Thr Arg Ser Gly Ser Leu Phe Asp Pro Gly Thr Phe Asp
            100                 105                 110

Tyr Trp Gly Gln Gly Thr Gln Val Thr Val Ser Ser
        115                 120

<210> SEQ ID NO 22
<211> LENGTH: 5
<212> TYPE: PRT
<213> ORGANISM: Lama glama

<400> SEQUENCE: 22

Asn Tyr Ile Met Gly
1               5

<210> SEQ ID NO 23
<211> LENGTH: 17
<212> TYPE: PRT
<213> ORGANISM: Lama glama

<400> SEQUENCE: 23

Ile Ile Thr Ala Asn Gly Val Ala Thr Asp Tyr Arg Asp Ser Val Lys
1               5                   10                  15

Gly

<210> SEQ ID NO 24
<211> LENGTH: 15
<212> TYPE: PRT
<213> ORGANISM: Lama glama

<400> SEQUENCE: 24

Arg Thr Arg Ser Gly Ser Leu Phe Asp Pro Gly Thr Phe Asp Tyr
1               5                   10                  15

<210> SEQ ID NO 25
<211> LENGTH: 30
<212> TYPE: PRT
<213> ORGANISM: Lama glama

```
<400> SEQUENCE: 25

Glu Val Gln Leu Val Glu Ser Gly Gly Gly Leu Val Gln Ala Gly Thr
1               5                   10                  15

Ser Leu Arg Leu Ser Cys Ala Ala Ser Gly Arg Thr Phe Ser
            20                  25                  30

<210> SEQ ID NO 26
<211> LENGTH: 14
<212> TYPE: PRT
<213> ORGANISM: Lama glama

<400> SEQUENCE: 26

Trp Phe Arg Gln Ala Pro Gly Lys Glu Arg Glu Phe Val Ala
1               5                   10

<210> SEQ ID NO 27
<211> LENGTH: 32
<212> TYPE: PRT
<213> ORGANISM: Lama glama

<400> SEQUENCE: 27

Arg Phe Thr Ile Ser Arg Asp Asn Ala Arg Asn Thr Gly Tyr Leu Glu
1               5                   10                  15

Met Asn Ser Leu Lys Pro Glu Asp Thr Ala Val Tyr Phe Cys Ala Leu
            20                  25                  30

<210> SEQ ID NO 28
<211> LENGTH: 11
<212> TYPE: PRT
<213> ORGANISM: Lama glama

<400> SEQUENCE: 28

Trp Gly Gln Gly Thr Gln Val Thr Val Ser Ser
1               5                   10

<210> SEQ ID NO 29
<211> LENGTH: 121
<212> TYPE: PRT
<213> ORGANISM: Lama glama

<400> SEQUENCE: 29

Glu Val Gln Leu Val Glu Ser Gly Gly Gly Gln Val Gln Pro Gly Gly
1               5                   10                  15

Ser Leu Arg Leu Ser Cys Glu Ser Ser Val Ser Ile Trp Ser Phe Lys
            20                  25                  30

Val Met Gly Trp Phe Arg Gln Val Pro Gly Lys Gln Arg Glu Leu Val
        35                  40                  45

Ala Thr Ile Thr Thr Gly Gly Ser Pro Asp Tyr Ser Asp Ser Val Lys
    50                  55                  60

Gly Arg Phe Thr Ile Ser Arg Asp Tyr Asp Lys Arg Thr Leu Tyr Leu
65                  70                  75                  80

Gln Met Asn Ser Leu Lys Pro Glu Asp Thr Ala Arg Tyr Tyr Cys Ala
                85                  90                  95

Gly Arg Leu Trp Ala His Ile Thr Ser Ser Gly His Asp Val Trp Gly
            100                 105                 110

Gln Gly Thr Gln Val Thr Val Ser Ser
            115                 120

<210> SEQ ID NO 30
<211> LENGTH: 121
```

```
<212> TYPE: PRT
<213> ORGANISM: Lama glama

<400> SEQUENCE: 30

Glu Val Gln Leu Val Glu Ser Gly Gly Gly Val Gln Pro Gly Gly
1               5                   10                  15

Ser Leu Ser Leu Ser Cys Glu Ser Ser Val Ser Ile Trp Ser Phe Lys
            20                  25                  30

Val Met Gly Trp Phe Arg Gln Val Pro Gly Lys Gln Arg Glu Leu Val
        35                  40                  45

Ala Thr Ile Thr Thr Gly Gly Ser Pro Asp Tyr Ser Asp Ser Val Lys
    50                  55                  60

Gly Arg Phe Thr Ile Ser Arg Asp Tyr Asp Lys Arg Thr Leu Tyr Leu
65                  70                  75                  80

Gln Met Asn Ser Leu Lys Pro Glu Asp Thr Ala Arg Tyr Tyr Cys Ala
                85                  90                  95

Gly Arg Leu Trp Ala His Ile Thr Ser Ser Gly His Asp Val Trp Gly
            100                 105                 110

Gln Gly Thr Gln Val Thr Val Ser Ser
            115                 120

<210> SEQ ID NO 31
<211> LENGTH: 121
<212> TYPE: PRT
<213> ORGANISM: Lama glama

<400> SEQUENCE: 31

Glu Val Gln Leu Val Glu Ser Gly Gly Gly Val Gln Pro Gly Gly
1               5                   10                  15

Ser Leu Arg Leu Ser Cys Glu Ser Ser Val Ser Ile Trp Ser Phe Lys
            20                  25                  30

Val Met Gly Trp Phe Arg Gln Ala Pro Gly Lys Gln Arg Glu Leu Val
        35                  40                  45

Ala Thr Ile Thr Thr Gly Gly Ser Pro Asp Tyr Ser Asp Ser Val Lys
    50                  55                  60

Gly Arg Phe Thr Ile Ser Arg Asp Tyr Asp Lys Arg Thr Leu Tyr Leu
65                  70                  75                  80

Gln Met Asn Ser Leu Lys Pro Glu Asp Thr Ala Arg Tyr Tyr Cys Ala
                85                  90                  95

Gly Arg Leu Trp Ala His Ile Thr Ser Ser Gly His Asp Val Trp Gly
            100                 105                 110

Gln Gly Thr Gln Val Thr Val Ser Ser
            115                 120

<210> SEQ ID NO 32
<211> LENGTH: 121
<212> TYPE: PRT
<213> ORGANISM: Lama glama

<400> SEQUENCE: 32

Glu Val Gln Leu Val Glu Ser Gly Gly Gly Val Gln Pro Gly Gly
1               5                   10                  15

Ser Leu Arg Leu Ser Cys Glu Ser Ser Val Ser Ile Trp Ser Phe Lys
            20                  25                  30

Val Met Gly Trp Phe Arg Gln Val Pro Gly Lys Gln Leu Glu Leu Val
        35                  40                  45

Ala Thr Ile Thr Thr Gly Gly Ser Pro Asp Tyr Ser Asp Ser Val Lys
```

```
                    50                  55                  60
Gly Arg Phe Thr Ile Ser Arg Asp Tyr Asp Lys Arg Thr Leu Tyr Leu
 65                  70                  75                  80

Gln Met Asn Ser Leu Lys Pro Glu Asp Thr Ala Arg Tyr Tyr Cys Ala
                 85                  90                  95

Gly Arg Leu Trp Ala His Ile Thr Ser Ser Gly His Asp Val Trp Gly
                100                 105                 110

Gln Gly Thr Gln Val Thr Val Ser Ser
            115                 120

<210> SEQ ID NO 33
<211> LENGTH: 121
<212> TYPE: PRT
<213> ORGANISM: Lama glama

<400> SEQUENCE: 33

Glu Val Gln Leu Val Glu Ser Gly Gly Gly Val Gln Pro Gly Gly
 1               5                  10                  15

Ser Leu Arg Leu Ser Cys Glu Ser Val Ser Ile Trp Ser Phe Lys
                 20                  25                  30

Val Met Gly Trp Phe Arg Gln Val Pro Gly Lys Gln Arg Glu Leu Val
                 35                  40                  45

Ala Thr Ile Thr Thr Gly Gly Ser Pro His Asp Gly Asp Ser Ala Lys
 50                  55                  60

Gly Arg Phe Thr Ile Ser Arg Asp Tyr Asp Lys Arg Thr Leu Tyr Leu
 65                  70                  75                  80

Gln Met Asn Ser Leu Lys Pro Glu Asp Thr Ala Arg Tyr Tyr Cys Ala
                 85                  90                  95

Gly Arg Leu Trp Ala His Ile Thr Ser Ser Gly His Asp Val Trp Gly
                100                 105                 110

Gln Gly Thr Gln Val Thr Val Ser Ser
            115                 120

<210> SEQ ID NO 34
<211> LENGTH: 121
<212> TYPE: PRT
<213> ORGANISM: Lama glama

<400> SEQUENCE: 34

Glu Val Gln Leu Val Glu Ser Gly Gly Gly Val Gln Pro Gly Gly
 1               5                  10                  15

Ser Leu Arg Leu Ser Cys Glu Ser Val Ser Ile Trp Ser Phe Lys
                 20                  25                  30

Val Met Gly Trp Phe Arg Gln Val Pro Gly Lys Gln Arg Glu Leu Val
                 35                  40                  45

Ala Thr Ile Thr Thr Gly Gly Ser Pro His Tyr Ser Asp Ser Val Lys
 50                  55                  60

Gly Arg Phe Thr Ile Ser Arg Asp Tyr Asp Lys Arg Thr Leu Tyr Leu
 65                  70                  75                  80

Gln Met Asn Ser Leu Lys Pro Glu Asp Thr Ala Arg Tyr Tyr Cys Ala
                 85                  90                  95

Gly Arg Leu Trp Ala His Ile Thr Ser Ser Gly His Asp Val Trp Gly
                100                 105                 110

Gln Gly Thr Gln Val Thr Val Ser Ser
            115                 120
```

-continued

```
<210> SEQ ID NO 35
<211> LENGTH: 121
<212> TYPE: PRT
<213> ORGANISM: Lama glama

<400> SEQUENCE: 35

Glu Val Gln Leu Val Glu Ser Gly Gly Gly Val Gln Pro Gly Gly
1               5                   10                  15

Ser Leu Arg Leu Ser Cys Glu Ser Ser Val Ser Ile Trp Ser Phe Lys
            20                  25                  30

Val Met Gly Trp Phe Arg Gln Val Pro Gly Lys Gln Arg Glu Leu Val
        35                  40                  45

Ala Thr Ile Thr Thr Gly Gly Ser Pro Asp Tyr Arg Asp Ser Val Lys
    50                  55                  60

Gly Arg Phe Thr Ile Ser Arg Asp Tyr Asp Lys Arg Thr Leu Tyr Leu
65                  70                  75                  80

Gln Met Asn Ser Leu Lys Pro Glu Asp Thr Ala Arg Tyr Tyr Cys Ala
                85                  90                  95

Gly Arg Leu Trp Ala His Ile Thr Ser Ser Gly His Asp Val Trp Gly
            100                 105                 110

Gln Gly Thr Gln Val Thr Val Ser Ser
        115                 120

<210> SEQ ID NO 36
<211> LENGTH: 121
<212> TYPE: PRT
<213> ORGANISM: Lama glama

<400> SEQUENCE: 36

Glu Val Gln Leu Val Glu Ser Gly Gly Gly Val Gln Pro Gly Gly
1               5                   10                  15

Ser Leu Arg Leu Ser Cys Glu Ser Ser Val Ser Ile Trp Ser Phe Lys
            20                  25                  30

Val Met Gly Trp Phe Arg Gln Val Pro Gly Lys Gln Arg Glu Leu Val
        35                  40                  45

Ala Thr Ile Thr Thr Gly Gly Ser Pro Asp Tyr Ser Asp Ser Val Lys
    50                  55                  60

Gly Arg Phe Thr Ile Ser Arg Asp Tyr Asp Lys Arg Thr Leu Tyr Leu
65                  70                  75                  80

Gln Met Asn Ser Leu Lys Ser Glu Asp Thr Ala Arg Tyr Tyr Cys Ala
                85                  90                  95

Gly Arg Leu Trp Ala His Ile Thr Ser Ser Gly His Asp Val Trp Gly
            100                 105                 110

Gln Gly Thr Gln Val Thr Val Ser Ser
        115                 120

<210> SEQ ID NO 37
<211> LENGTH: 121
<212> TYPE: PRT
<213> ORGANISM: Lama glama

<400> SEQUENCE: 37

Glu Val Gln Leu Val Glu Ser Gly Gly Gly Val Gln Pro Gly Gly
1               5                   10                  15

Ser Leu Arg Leu Ser Cys Glu Ser Ser Val Ser Ile Trp Ser Phe Lys
            20                  25                  30

Val Met Gly Trp Phe Arg Gln Val Pro Gly Lys Gln Arg Glu Leu Val
        35                  40                  45
```

```
Ala Thr Ile Thr Thr Gly Gly Ser Pro Asp Tyr Ser Asp Ser Val Lys
        50                  55                  60

Gly Arg Phe Thr Ile Ser Arg Asp Tyr Asp Lys Arg Thr Leu Tyr Leu
 65                  70                  75                  80

Gln Met Asn Ser Leu Lys Pro Glu Asp Thr Ala Val Tyr Tyr Cys Ala
                 85                  90                  95

Gly Arg Leu Trp Ala His Ile Thr Ser Ser Gly His Asp Val Trp Gly
                100                 105                 110

Gln Gly Thr Gln Val Thr Val Ser Ser
                115                 120
```

<210> SEQ ID NO 38
<211> LENGTH: 121
<212> TYPE: PRT
<213> ORGANISM: Lama glama

<400> SEQUENCE: 38

```
Glu Val Gln Leu Val Glu Ser Gly Gly Gly Val Gln Pro Gly Gly
 1               5                  10                  15

Ser Leu Ser Leu Ser Cys Glu Ser Ser Val Ser Ile Trp Ser Phe Lys
                 20                  25                  30

Val Met Gly Trp Phe Arg Gln Val Pro Gly Lys Gln Arg Glu Leu Val
             35                  40                  45

Ala Thr Ile Thr Thr Gly Gly Ser Pro Asp Tyr Ser Asp Ser Val Lys
        50                  55                  60

Gly Arg Phe Thr Ile Ser Arg Asp Tyr Asp Lys Arg Thr Leu Tyr Leu
 65                  70                  75                  80

Gln Met Asn Ser Leu Lys Pro Glu Asp Thr Ala Val Tyr Tyr Cys Ala
                 85                  90                  95

Gly Arg Leu Trp Ala His Ile Thr Ser Ser Gly His Asp Val Trp Gly
                100                 105                 110

Gln Gly Thr Gln Val Thr Val Ser Ser
                115                 120
```

<210> SEQ ID NO 39
<211> LENGTH: 121
<212> TYPE: PRT
<213> ORGANISM: Lama glama

<400> SEQUENCE: 39

```
Glu Val Gln Leu Val Glu Ser Gly Gly Gly Val Gln Pro Gly Gly
 1               5                  10                  15

Ser Leu Ser Leu Ser Cys Glu Ser Ser Val Ser Ile Trp Ser Phe Lys
                 20                  25                  30

Val Met Gly Trp Phe Arg Gln Ala Pro Gly Lys Gln Arg Glu Leu Val
             35                  40                  45

Ala Thr Ile Thr Thr Gly Gly Ser Pro Asp Tyr Ser Asp Ser Val Lys
        50                  55                  60

Gly Arg Phe Thr Leu Ser Arg Asp Tyr Asp Lys Arg Thr Val Tyr Leu
 65                  70                  75                  80

Gln Met Asn Ser Leu Lys Pro Glu Asp Thr Ala Val Tyr Tyr Cys Ala
                 85                  90                  95

Gly Arg Leu Trp Ala His Ile Thr Ser Ser Gly His Asp Val Trp Gly
                100                 105                 110

Gln Gly Thr Gln Val Thr Val Ser Ser
                115                 120
```

<210> SEQ ID NO 40
<211> LENGTH: 121
<212> TYPE: PRT
<213> ORGANISM: Lama glama

<400> SEQUENCE: 40

Glu Val Gln Leu Val Glu Ser Gly Gly Gly Val Gln Pro Gly Gly
1               5                   10                  15

Ser Leu Ser Leu Ser Cys Glu Ser Ser Val Ser Ile Trp Ser Phe Lys
                20                  25                  30

Val Met Gly Trp Phe Arg Gln Ala Pro Gly Lys Gln Leu Glu Leu Val
            35                  40                  45

Ala Thr Ile Thr Thr Gly Gly Ser Pro Asp Tyr Ser Asp Ser Val Lys
        50                  55                  60

Gly Arg Phe Thr Ile Ser Arg Asp Tyr Asp Lys Arg Thr Leu Tyr Leu
65                  70                  75                  80

Gln Met Asn Ser Leu Lys Pro Glu Asp Thr Ala Val Tyr Tyr Cys Ala
                85                  90                  95

Gly Arg Leu Trp Ala His Ile Thr Ser Ser Gly His Asp Val Trp Gly
            100                 105                 110

Gln Gly Thr Gln Val Thr Val Ser Ser
        115                 120

<210> SEQ ID NO 41
<211> LENGTH: 121
<212> TYPE: PRT
<213> ORGANISM: Lama glama

<400> SEQUENCE: 41

Glu Val Gln Leu Val Glu Ser Gly Gly Gly Val Gln Pro Gly Gly
1               5                   10                  15

Ser Leu Ser Leu Ser Cys Glu Ser Ser Val Ser Ile Trp Ser Phe Lys
                20                  25                  30

Val Met Gly Trp Phe Arg Gln Val Pro Gly His Gln Leu Glu Leu Val
            35                  40                  45

Ala Thr Ile Thr Thr Gly Gly Ser Pro Asp Tyr Ser Asp Ser Val Lys
        50                  55                  60

Gly Arg Phe Thr Ile Ser Arg Asp Tyr Asp Lys Arg Thr Leu Tyr Leu
65                  70                  75                  80

Gln Met Asn Ser Leu Lys Pro Glu Asp Thr Ala Val Tyr Tyr Cys Ala
                85                  90                  95

Gly Arg Leu Trp Ala His Ile Thr Ser Ser Gly His Asp Val Trp Gly
            100                 105                 110

Gln Gly Thr Gln Val Thr Val Ser Ser
        115                 120

<210> SEQ ID NO 42
<211> LENGTH: 121
<212> TYPE: PRT
<213> ORGANISM: Lama glama

<400> SEQUENCE: 42

Glu Val Gln Leu Val Glu Ser Gly Gly Gly Val Gln Pro Gly Gly
1               5                   10                  15

Ser Leu Ser Leu Ser Cys Glu Ser Ser Val Ser Ile Trp Ser Phe Lys
                20                  25                  30

Val Met Gly Trp Phe Arg Gln Ala Pro Gly Lys Gln Leu Glu Leu Val
           35                  40                  45

Ala Thr Ile Thr Thr Gly Gly Ser Pro His Tyr Ser Asp Ser Val Lys
 50                      55                  60

Gly Arg Phe Thr Ile Ser Arg Asp Tyr Asp Lys Arg Thr Leu Tyr Leu
 65                  70                  75                  80

Gln Met Asn Ser Leu Lys Pro Glu Asp Thr Ala Val Tyr Tyr Cys Ala
             85                  90                  95

Gly Arg Leu Trp Ala His Ile Thr Ser Ser Gly His Asp Val Trp Gly
            100                 105                 110

Gln Gly Thr Gln Val Thr Val Ser Ser
            115                 120

<210> SEQ ID NO 43
<211> LENGTH: 121
<212> TYPE: PRT
<213> ORGANISM: Lama glama

<400> SEQUENCE: 43

Glu Val Gln Leu Val Glu Ser Gly Gly Gly Val Gln Pro Gly Gly
 1               5                  10                  15

Ser Leu Ser Leu Ser Cys Glu Ser Val Ser Ile Trp Ser Phe Lys
                 20                  25                  30

Val Met Gly Trp Phe Arg Gln Ala Pro Gly Lys Gln Leu Glu Phe Val
           35                  40                  45

Ala Thr Ile Thr Thr Gly Gly Ser Pro His Tyr Ser Asp Ser Val Lys
 50                      55                  60

Gly Arg Phe Thr Ile Ser Arg Asp Tyr Asp Lys Arg Thr Leu Tyr Leu
 65                  70                  75                  80

Gln Met Asn Ser Leu Lys Pro Glu Asp Thr Ala Val Tyr Tyr Cys Ala
             85                  90                  95

Gly Arg Leu Trp Ala His Ile Thr Ser Ser Gly His Asp Val Trp Gly
            100                 105                 110

Gln Gly Thr Gln Val Thr Val Ser Ser
            115                 120

<210> SEQ ID NO 44
<211> LENGTH: 121
<212> TYPE: PRT
<213> ORGANISM: Lama glama

<400> SEQUENCE: 44

Glu Val Gln Leu Val Glu Ser Gly Gly Gly Val Gln Pro Gly Gly
 1               5                  10                  15

Ser Leu Arg Leu Ser Cys Glu Ser Val Ser Ile Trp Ser Phe Lys
                 20                  25                  30

Val Met Gly Trp Phe Arg Gln Val Pro Gly Lys Glu Arg Glu Phe Val
           35                  40                  45

Ala Thr Ile Thr Thr Gly Gly Ser Pro His Tyr Ser Asp Ser Val Lys
 50                      55                  60

Gly Arg Phe Thr Ile Ser Arg Asp Tyr Asp Lys Arg Thr Leu Tyr Leu
 65                  70                  75                  80

Gln Met Asn Ser Leu Lys Pro Glu Asp Thr Ala Val Tyr Tyr Cys Ala
             85                  90                  95

Gly Arg Leu Trp Ala His Ile Thr Ser Ser Gly His Asp Val Trp Gly
            100                 105                 110

Gln Gly Thr Gln Val Thr Val Ser Ser
            115                 120

<210> SEQ ID NO 45
<211> LENGTH: 121
<212> TYPE: PRT
<213> ORGANISM: Lama glama

<400> SEQUENCE: 45

Glu Val Gln Leu Val Glu Ser Gly Gly Gly Val Gln Pro Gly Gly
1               5                   10                  15

Ser Leu Ser Leu Ser Cys Glu Ser Ser Val Ser Ile Trp Ser Phe Lys
            20                  25                  30

Val Met Gly Trp Phe Arg Gln Ala Pro Gly Lys Glu Leu Glu Leu Val
            35                  40                  45

Ala Thr Ile Thr Thr Gly Gly Ser Pro Asp Tyr Ser Asp Ser Val Lys
        50                  55                  60

Gly Arg Phe Thr Leu Ser Arg Asp Tyr Asp Lys Arg Thr Val Tyr Leu
65                  70                  75                  80

Gln Met Asn Ser Leu Lys Pro Glu Asp Thr Ala Val Tyr Tyr Cys Ala
                85                  90                  95

Gly Arg Leu Trp Ala His Ile Thr Ser Ser Gly His Asp Val Trp Gly
            100                 105                 110

Gln Gly Thr Gln Val Thr Val Ser Ser
            115                 120

<210> SEQ ID NO 46
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
            35                  40                  45

Ser Glu Ile Asn Thr Asn Gly Leu Ile Thr His Tyr Gly Asp Ser Val
        50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln His Gly Leu Asn Lys Gly Gln Gly Thr Gln Val Thr
            100                 105                 110

Val Ser Ser Gly Gly Gly Gly Ser Gly Gly Gly Ser Lys Gly Gly
            115                 120                 125

Gly Gly Ser Gly Gly Gly Ser Glu Val Gln Leu Val Glu Ser Gly
            130                 135                 140

Gly Gly Gln Val Gln Pro Gly Gly Ser Leu Ser Leu Ser Cys Glu Ser
145                 150                 155                 160

Ser Val Ser Ile Trp Ser Phe Lys Val Met Gly Trp Phe Arg Gln Val
                165                 170                 175

-continued

Pro Gly Lys Gln Arg Glu Leu Val Ala Thr Ile Thr Thr Gly Gly Ser
            180                 185                 190

Pro Asp Tyr Ser Asp Ser Val Lys Gly Arg Phe Thr Ile Ser Arg Asp
            195                 200                 205

Tyr Asp Lys Arg Thr Leu Tyr Leu Gln Met Asn Ser Leu Lys Pro Glu
        210                 215                 220

Asp Thr Ala Val Tyr Tyr Cys Ala Gly Arg Leu Trp Ala His Ile Thr
225                 230                 235                 240

Ser Ser Gly His Asp Val Trp Gly Gln Gly Thr Gln Val Thr Val Ser
                245                 250                 255

Ser

<210> SEQ ID NO 47
<211> LENGTH: 115
<212> TYPE: PRT
<213> ORGANISM: Lama glama

<400> SEQUENCE: 47

Asp Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr His Tyr Gly Asp Ser Val
    50                  55                  60

Lys Gly Arg Phe Thr Val Ser Arg Asn Asn Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln His Gly Leu Asn Lys Gly Gln Gly Thr Gln Val Thr
            100                 105                 110

Val Ser Ser
        115

<210> SEQ ID NO 48
<211> LENGTH: 121
<212> TYPE: PRT
<213> ORGANISM: Lama glama

<400> SEQUENCE: 48

Glu Val Gln Leu Val Glu Ser Gly Gly Gly Val Gln Pro Gly Gly
1               5                   10                  15

Ser Leu Ser Leu Ser Cys Glu Ser Ser Val Ser Ile Trp Ser Phe Lys
            20                  25                  30

Val Met Gly Trp Phe Arg Gln Val Pro Gly Lys Gln Arg Glu Leu Val
        35                  40                  45

Ala Thr Ile Thr Thr Gly Gly Ser Pro Asp Tyr Ser Asp Ser Val Lys
    50                  55                  60

Gly Arg Phe Thr Ile Ser Arg Asp Tyr Asp Lys Arg Thr Leu Tyr Leu
65                  70                  75                  80

Gln Met Asn Ser Leu Lys Pro Glu Asp Thr Ala Val Tyr Tyr Cys Ala
                85                  90                  95

Gly Arg Leu Trp Ala His Ile Thr Ser Ser Gly His Asp Val Trp Gly
            100                 105                 110

Gln Gly Thr Gln Val Thr Val Ser Ser
        115                 120

<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Gly Gly Gly Gly Ser Gly Gly Gly Ser Lys Gly Gly Gly Ser
1               5                   10                  15

Gly Gly Gly Gly Ser
            20

<210> SEQ ID NO 50
<211> LENGTH: 363
<212> TYPE: DNA
<213> ORGANISM: Lama glama

<400> SEQUENCE: 50
gaagttcagc tggttgaaag cggtggtggt caggttcagc ctggtggtag cctgcgtctg      60
agctgtgaaa gcagcgttag catttggagc tttaaagtta tgggttggtt tcgtcaggtt     120
ccgggtaaac agcgtgaact ggttgccacc attaccacag gtggtagtcc ggattatagc     180
gatagcgtta aggtcgtttt taccatcagc cgtgattatg ataaacgtac cctgtacctg     240
cagatgaata gcctgaaacc ggaagatacc gcacgttatt attgtgcagg tcgtctgtgg     300
gcacatatta ccagcagcgg tcatgatgtt tggggtcagg caccaggt caccgttagc       360 agc                                                                   363

<210> SEQ ID NO 51
<211> LENGTH: 363
<212> TYPE: DNA
<213> ORGANISM: Lama glama

<400> SEQUENCE: 51
gaagttcagc tggttgaaag cggtggtggt caggttcagc ctggtggtag cctgagcctg      60
agctgtgaaa gcagcgttag catttggagc tttaaagtta tgggttggtt tcgtcaggtt     120
ccgggtaaac agcgtgaact ggttgccacc attaccacag gtggtagtcc ggattatagc     180
gatagcgtta aggtcgtttt taccatcagc cgtgattatg ataaacgtac cctgtacctg     240
cagatgaata gcctgaaacc ggaagatacc gcacgttatt attgtgcagg tcgtctgtgg     300
gcacatatta ccagcagcgg tcatgatgtt tggggtcagg caccaggt caccgttagc       360 agc                                                                   363

<210> SEQ ID NO 52
<211> LENGTH: 363
<212> TYPE: DNA
<213> ORGANISM: Lama glama

<400> SEQUENCE: 52
gaagttcagc tggttgaaag cggtggtggt caggttcagc ctggtggtag cctgcgtctg      60
agctgtgaaa gcagcgttag catttggagc tttaaagtta tgggttggtt tcgtcaggca     120
ccgggtaaac agcgtgaact ggttgccacc attaccacag gtggtagtcc ggattatagc     180
gatagcgtta aggtcgtttt taccatcagc cgtgattatg ataaacgtac cctgtacctg     240
cagatgaata gcctgaaacc ggaagatacc gcacgttatt attgtgcagg tcgtctgtgg      300
gcacatatta ccagcagcgg tcatgatgtt tggggtcagg gcacccaggt caccgttagc      360
agc                                                                   363

<210> SEQ ID NO 53
<211> LENGTH: 363
<212> TYPE: DNA
<213> ORGANISM: Lama glama

<400> SEQUENCE: 53
gaagttcagc tggttgaaag cggtggtggt caggttcagc ctggtggtag cctgcgtctg       60
agctgtgaaa gcagcgttag catttggagc tttaaagtta tgggttggtt tcgtcaggtt      120
ccgggtaaac agctggaact ggttgccacc attaccacag gtggtagtcc ggattatagc      180
gatagcgtta aaggtcgttt taccatcagc cgtgattatg ataaacgtac cctgtacctg      240
cagatgaata gcctgaaacc ggaagatacc gcacgttatt attgtgcagg tcgtctgtgg      300
gcacatatta ccagcagcgg tcatgatgtt tggggtcagg gcacccaggt caccgttagc      360
agc                                                                   363

<210> SEQ ID NO 54
<211> LENGTH: 363
<212> TYPE: DNA
<213> ORGANISM: Lama glama

<400> SEQUENCE: 54
gaagttcagc tggttgaaag cggtggtggt caggttcagc ctggtggtag cctgcgtctg       60
agctgtgaaa gcagcgttag catttggagc tttaaagtta tgggttggtt tcgtcaggtt      120
ccgggtaaac agctggaact ggttgccacc attaccacag gtggtagtcc gcatgatggt      180
gatagcgcaa aaggtcgttt taccattagc cgtgattatg ataaacgtac cctgtacctg      240
cagatgaata gcctgaaacc ggaagatacc gcacgttatt attgtgcagg tcgtctgtgg      300
gcacatatta ccagcagcgg tcatgatgtt tggggtcagg gcacccaggt caccgttagc      360
agc                                                                   363

<210> SEQ ID NO 55
<211> LENGTH: 363
<212> TYPE: DNA
<213> ORGANISM: Lama glama

<400> SEQUENCE: 55
gaagttcagc tggttgaaag cggtggtggt caggttcagc ctggtggtag cctgcgtctg       60
agctgtgaaa gcagcgttag catttggagc tttaaagtta tgggttggtt tcgtcaggtt      120
ccgggtaaac agctggaact ggttgccacc attaccacag gtggtagtcc gcattatagc      180
gatagcgtta aaggtcgttt taccatcagc cgtgattatg ataaacgtac cctgtacctg      240
cagatgaata gcctgaaacc ggaagatacc gcacgttatt attgtgcagg tcgtctgtgg      300
gcacatatta ccagcagcgg tcatgatgtt tggggtcagg gcacccaggt caccgttagc      360
agc                                                                   363

<210> SEQ ID NO 56
<211> LENGTH: 363
<212> TYPE: DNA
<213> ORGANISM: Lama glama

<400> SEQUENCE: 56

```
gaagttcagc tggttgaaag cggtggtggt caggttcagc ctggtggtag cctgcgtctg    60
agctgtgaaa gcagcgttag catttggagc tttaaagtta tgggttggtt tcgtcaggtt   120
ccgggtaaac agcgtgaact ggttgccacc attaccacag gtggtagtcc ggattatcgt   180
gatagcgtta aaggtcgttt taccatcagc cgtgattatg ataaacgtac cctgtacctg   240
cagatgaata gcctgaaacc ggaagatacc gcacgttatt attgtgcagg tcgtctgtgg   300
gcacatatta ccagcagcgg tcatgatgtt tggggtcagg gcacccaggt caccgttagc   360
agc                                                                 363
```

<210> SEQ ID NO 57
<211> LENGTH: 363
<212> TYPE: DNA
<213> ORGANISM: Lama glama

<400> SEQUENCE: 57

```
gaagttcagc tggttgaaag cggtggtggt caggttcagc ctggtggtag cctgcgtctg    60
agctgtgaaa gcagcgttag catttggagc tttaaagtta tgggttggtt tcgtcaggtt   120
ccgggtaaac agcgtgaact ggttgccacc attaccacag gtggtagtcc ggattatagc   180
gatagcgtta aaggtcgttt taccatcagc cgtgattatg ataaacgtac cctgtacctg   240
cagatgaata gcctgaaaag cgaagatacc gcacgttatt attgtgcagg tcgtctgtgg   300
gcacatatta ccagcagcgg tcatgatgtt tggggtcagg gcacccaggt caccgttagc   360
agc                                                                 363
```

<210> SEQ ID NO 58
<211> LENGTH: 363
<212> TYPE: DNA
<213> ORGANISM: Lama glama

<400> SEQUENCE: 58

```
gaagttcagc tggttgaaag cggtggtggt caggttcagc ctggtggtag cctgcgtctg    60
agctgtgaaa gcagcgttag catttggagc tttaaagtta tgggttggtt tcgtcaggtt   120
ccgggtaaac agcgtgaact ggttgccacc attaccacag gtggtagtcc ggattatagc   180
gatagcgtta aaggtcgttt taccatcagc cgtgattatg ataaacgtac cctgtacctg   240
cagatgaata gcctgaaacc ggaagatacc gcagtgtatt attgtgcagg tcgtctgtgg   300
gcacatatta ccagcagcgg tcatgatgtt tggggtcagg gcacccaggt caccgttagc   360
agc                                                                 363
```

<210> SEQ ID NO 59
<211> LENGTH: 363
<212> TYPE: DNA
<213> ORGANISM: Lama glama

<400> SEQUENCE: 59

```
gaagttcagc tggttgaaag cggtggtggt caggttcagc ctggtggtag cctgagcctg    60
agctgtgaaa gcagcgttag catttggagc tttaaagtta tgggttggtt tcgtcaggtt   120
ccgggtaaac agcgtgaact ggttgccacc attaccacag gtggtagtcc ggattatagc   180
gatagcgtta aaggtcgttt taccatcagc cgtgattatg ataaacgtac cctgtacctg   240
cagatgaata gcctgaaacc ggaagatacc gcagtgtatt attgtgcagg tcgtctgtgg   300
gcacatatta ccagcagcgg tcatgatgtt tggggtcagg gcacccaggt caccgttagc   360
```

| agc | 363 |

<210> SEQ ID NO 60
<211> LENGTH: 363
<212> TYPE: DNA
<213> ORGANISM: Lama glama

<400> SEQUENCE: 60

| gaagttcagc tggttgaaag cggtggtggt caggttcagc ctggtggtag cctgagcctg | 60 |
| agctgtgaaa gcagcgttag catttggagc tttaaagtta tgggttggtt tcgtcaggca | 120 |
| ccgggtaaac agcgtgaact ggttgccacc attaccacag gtggtagtcc ggattatagc | 180 |
| gatagcgtta aggtcgtttt taccctgagc cgtgattatg ataaacgtac cgtttacctg | 240 |
| cagatgaata gcctgaaacc ggaagatacc gcagtgtatt attgtgcagg tcgtctgtgg | 300 |
| gcacatatta ccagcagcgg tcatgatgtt tggggtcagg gcacccaggt caccgttagc | 360 |
| agc | 363 |

<210> SEQ ID NO 61
<211> LENGTH: 363
<212> TYPE: DNA
<213> ORGANISM: Lama glama

<400> SEQUENCE: 61

| gaagttcagc tggttgaaag cggtggtggt caggttcagc ctggtggtag cctgagcctg | 60 |
| agctgtgaaa gcagcgttag catttggagc tttaaagtta tgggttggtt tcgtcaggca | 120 |
| ccgggtaaac agctggaact ggttgccacc attaccacag gtggtagtcc ggattatagc | 180 |
| gatagcgtta aggtcgtttt taccatcagc cgtgattatg ataaacgtac cctgtacctg | 240 |
| cagatgaata gcctgaaacc ggaagatacc gcagtgtatt attgtgcagg tcgtctgtgg | 300 |
| gcacatatta ccagcagcgg tcatgatgtt tggggtcagg gcacccaggt caccgttagc | 360 |
| agc | 363 |

<210> SEQ ID NO 62
<211> LENGTH: 363
<212> TYPE: DNA
<213> ORGANISM: Lama glama

<400> SEQUENCE: 62

| gaagttcagc tggttgaaag cggtggtggt caggttcagc ctggtggtag cctgagcctg | 60 |
| agctgtgaaa gcagcgttag catttggagc tttaaagtta tgggttggtt tcgtcaggtt | 120 |
| ccgggtcatc agctggaact ggttgccacc attaccacag gtggtagtcc ggattatagc | 180 |
| gatagcgtta aggtcgtttt taccatcagc cgtgattatg ataaacgtac cctgtacctg | 240 |
| cagatgaata gcctgaaacc ggaagatacc gcagtgtatt attgtgcagg tcgtctgtgg | 300 |
| gcacatatta ccagcagcgg tcatgatgtt tggggtcagg gcacccaggt caccgttagc | 360 |
| agc | 363 |

<210> SEQ ID NO 63
<211> LENGTH: 363
<212> TYPE: DNA
<213> ORGANISM: Lama glama

<400> SEQUENCE: 63

| gaagttcagc tggttgaaag cggtggtggt caggttcagc ctggtggtag cctgagcctg | 60 |
| agctgtgaaa gcagcgttag catttggagc tttaaagtta tgggttggtt tcgtcaggca | 120 |

```
ccgggtaaac agctggaact ggttgccacc attaccacag gtggtagtcc gcattatagc      180
gatagcgtta aaggtcgttt taccatcagc cgtgattatg ataaacgtac cctgtacctg      240
cagatgaata gcctgaaacc ggaagatacc gcagtgtatt attgtgcagg tcgtctgtgg      300
gcacatatta ccagcagcgg tcatgatgtt tggggtcagg gcacccaggt caccgttagc      360
agc                                                                    363

<210> SEQ ID NO 64
<211> LENGTH: 363
<212> TYPE: DNA
<213> ORGANISM: Lama glama

<400> SEQUENCE: 64
gaagttcagc tggttgaaag cggtggtggt caggttcagc ctggtggtag cctgagcctg       60
agctgtgaaa gcagcgttag catttggagc tttaaagtta tgggttggtt tcgtcaggca      120
ccgggtaaac agctggaatt tgttgcaacc attaccacag gtggtagtcc gcattatagc      180
gatagcgtta aaggtcgttt taccatcagc cgtgattatg ataaacgtac cctgtacctg      240
cagatgaata gcctgaaacc ggaagatacc gcagtgtatt attgtgcagg tcgtctgtgg      300
gcacatatta ccagcagcgg tcatgatgtt tggggtcagg gcacccaggt caccgttagc      360
agc                                                                    363

<210> SEQ ID NO 65
<211> LENGTH: 363
<212> TYPE: DNA
<213> ORGANISM: Lama glama

<400> SEQUENCE: 65
gaagttcagc tggttgaaag cggtggtggt caggttcagc ctggtggtag cctgcgtctg       60
agctgtgaaa gcagcgttag catttggagc tttaaagtta tgggttggtt tcgtcaggtt      120
ccgggtaaag aacgtgaatt tgttgcaacc attaccacag gtggtagtcc gcattatagc      180
gatagcgtta aaggtcgttt taccatcagc cgtgattatg ataaacgtac cctgtacctg      240
cagatgaata gcctgaaacc ggaagatacc gcagtgtatt attgtgcagg tcgtctgtgg      300
gcacatatta ccagcagcgg tcatgatgtt tggggtcagg gcacccaggt caccgttagc      360
agc                                                                    363

<210> SEQ ID NO 66
<211> LENGTH: 363
<212> TYPE: DNA
<213> ORGANISM: Lama glama

<400> SEQUENCE: 66
gaagttcagc tggttgaaag cggtggtggt caggttcagc ctggtggtag cctgagcctg       60
agctgtgaaa gcagcgttag catttggagc tttaaagtta tgggttggtt tcgtcaaggca     120 ccgggtaaag aactggaact ggttgccacc attaccacag gtggtagtcc ggattatagc      180
gatagcgtta aaggtcgttt tacccctgagc cgtgattatg ataaacgtac cgtttacctg    240
cagatgaata gcctgaaacc ggaagatacc gcagtgtatt attgtgcagg tcgtctgtgg      300
gcacatatta ccagcagcgg tcatgatgtt tggggtcagg gcacccaggt caccgttagc      360
agc                                                                    363

<210> SEQ ID NO 67
```

<211> LENGTH: 115
<212> TYPE: PRT
<213> ORGANISM: Lama glama

<400> SEQUENCE: 67

Asp Val Gln Leu Val Glu Ser Gly Gly Gly Leu Val Gln Pro Gly Gly
1               5                   10                  15
Ser Leu Lys Leu Ser Cys Ala Ala Ser Gly Phe Asp Phe Ser Ser His
            20                  25                  30
Trp Met Tyr Trp Val Arg Gln Ala Pro Gly Lys Glu Leu Glu Trp Leu
        35                  40                  45
Ser Glu Ile Asn Thr Asn Gly Leu Ile Thr His Tyr Gly Asp Ser Val
    50                  55                  60
Lys Gly Arg Phe Thr Val Ser Arg Asn Asn Ala Ala Asn Lys Met Tyr
65                  70                  75                  80
Leu Glu Leu Thr Arg Leu Glu Pro Glu Asp Thr Ala Leu Tyr Tyr Cys
                85                  90                  95
Ala Arg Asn Gln His Gly Leu Asn Lys Gly Gln Gly Thr Gln Val Thr
            100                 105                 110
Val Ser Ser
        115

<210> SEQ ID NO 68
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tcttaactag tgaggagacg gtgacctg                                      28

<210> SEQ ID NO 69
<211> LENGTH: 126
<212> TYPE: PRT
<213> ORGANISM: Lama glama

<400> SEQUENCE: 69

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Leu Asp Tyr Leu
            20                  25                  30
Ala Ile Gly Trp Phe Arg Gln Ala Pro Gly Lys Glu Arg Glu Gly Val
        35                  40                  45
Ser Cys Val Ser Ser Ser Gly Gln Tyr Thr Tyr Tyr Ala Asp Ser Val
    50                  55                  60
Lys Gly Arg Phe Thr Ile Ser Arg Asp Asn Ala Glu Ser Thr Val Tyr
65                  70                  75                  80
Leu Gln Met Asn Ser Leu Lys Pro Glu Asp Thr Ala Val Tyr Tyr Cys
                85                  90                  95
Ala Thr Asp Pro Glu Cys Tyr Arg Val Arg Gly Tyr Tyr Asn Gly Glu
            100                 105                 110
Tyr Asp Tyr Trp Gly Gln Gly Thr Gln Val Thr Val Ser Ser
        115                 120                 125

<210> SEQ ID NO 70
<211> LENGTH: 469
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 70

```
Met Gly Trp Thr Leu Val Phe Leu Phe Leu Leu Ser Val Thr Ala Gly
1               5                   10                  15

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Trp Tyr Asp Gly Ser Asn Glu Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Arg Gly Tyr Thr Ser Ser Trp Tyr Pro Asp
        115                 120                 125

Ala Phe Asp Ile Trp Gly Gln Gly Thr Met Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
            340                 345                 350

Pro Ile Glu Lys Thr Ile Ser Lys Thr Lys Gly Gln Pro Arg Glu Pro
        355                 360                 365

Gln Val Tyr Thr Leu Pro Pro Ser Arg Glu Glu Met Thr Lys Asn Gln
    370                 375                 380
```

```
Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Met Leu Asp Ser Asp Gly Ser Phe Phe Leu Tyr Ser Lys Leu
        420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
        450                 455                 460

Leu Ser Pro Gly Lys
465

<210> SEQ ID NO 71
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Val Ser Ser Ala Gln Phe Leu Gly Leu Leu Leu Cys Phe Gln
1               5                   10                  15

Gly Thr Arg Cys Gln Ser Val Leu Thr Gln Pro Pro Ser Val Ser Gly
            20                  25                  30

Ala Pro Gly Gln Arg Val Thr Ile Ser Cys Thr Gly Ser Ser Ser Asn
        35                  40                  45

Thr Gly Ala Gly Tyr Asp Val His Trp Tyr Gln Gln Val Pro Gly Thr
    50                  55                  60

Ala Pro Lys Leu Leu Ile Tyr Gly Ser Gly Asn Arg Pro Ser Gly Val
65                  70                  75                  80

Pro Asp Arg Phe Ser Gly Ser Lys Ser Gly Thr Ser Ala Ser Leu Ala
            85                  90                  95

Ile Thr Gly Leu Gln Ala Glu Asp Glu Ala Asp Tyr Tyr Cys Gln Ser
        100                 105                 110

Tyr Asp Ser Ser Leu Ser Gly Trp Val Phe Gly Gly Gly Thr Arg Leu
    115                 120                 125

Thr Val Leu Gly Gln Pro Lys Ala Ala Pro Ser Val Thr Leu Phe Pro
    130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
            165                 170                 175

Ser Ser Pro Val Lys Ala Gly Val Glu Thr Thr Thr Pro Ser Lys Gln
        180                 185                 190

Ser Asn Asn Lys Tyr Ala Ala Ser Ser Tyr Leu Ser Leu Thr Pro Glu
    195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
225                 230                 235

<210> SEQ ID NO 72
<211> LENGTH: 189
<212> TYPE: PRT
<213> ORGANISM: Homo sapiens
```

-continued

<400> SEQUENCE: 72

Met Leu Gly Ser Arg Ala Val Met Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185

<210> SEQ ID NO 73
<211> LENGTH: 328
<212> TYPE: PRT
<213> ORGANISM: Homo sapiens

<400> SEQUENCE: 73

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 74
<211> LENGTH: 23
<212> TYPE: PRT
<213> ORGANISM: Artificial Sequence
<220> FEATURE:
<223> OTHER INFORMATION: Protease-labile linker format
<220> FEATURE:
<221> NAME/KEY: VARIANT
<222> LOCATION: (1)..(23)
<223> OTHER INFORMATION: Said features may be present 1 to 10 times
<220> FEATURE:
<221> NAME/KEY: VARIANT
<222> LOCATION: (1)..(11)
<223> OTHER INFORMATION: Said features may be present 1 to 10 times
<220> FEATURE:
<221> NAME/KEY: VARIANT
<222> LOCATION: (2)..(10)
<223> OTHER INFORMATION: None, some, or all of said Gly residues may be
      present
<220> FEATURE:
<221> NAME/KEY: MISC_FEATURE
<222> LOCATION: (12)..(12)
<223> OTHER INFORMATION: Xaa is Lys or Arg
<220> FEATURE:
<221> NAME/KEY: VARIANT
<222> LOCATION: (13)..(23)
<223> OTHER INFORMATION: Said residues may be present 1 to 10 times
<220> FEATURE:
<221> NAME/KEY: VARIANT
<222> LOCATION: (14)..(22)
<223> OTHER INFORMATION: None, some, or all of said Gly residues may be
      present

<400> SEQUENCE: 74

Gly Gly Gly Gly Gly Gly Gly Gly Gly Ser Xaa Gly Gly Gly Gly
1               5                   10                  15

Gly Gly Gly Gly Gly Gly Ser
            20

<210> SEQ ID NO 75
<211> LENGTH: 21
<212> TYPE: PRT
<213> ORGANISM: Artificial Sequence
<220> FEATURE:

```
<223> OTHER INFORMATION: Protease-labile linker sequence

<400> SEQUENCE: 75

Gly Gly Gly Gly Ser Gly Gly Gly Gly Ser Lys Gly Gly Gly Ser
1               5                   10                  15

Gly Gly Gly Gly Ser
            20

<210> SEQ ID NO 76
<211> LENGTH: 5
<212> TYPE: PRT
<213> ORGANISM: Artificial Sequence
<220> FEATURE:
<223> OTHER INFORMATION: Non-protease-labile linker format
<220> FEATURE:
<221> NAME/KEY: VARIANT
<222> LOCATION: (1)..(5)
<223> OTHER INFORMATION: Said residues may be present 1 to 10 times

<400> SEQUENCE: 76

Gly Gly Gly Gly Ser
1               5

<210> SEQ ID NO 77
<211> LENGTH: 30
<212> TYPE: PRT
<213> ORGANISM: Artificial Sequence
<220> FEATURE:
<223> OTHER INFORMATION: Non-protease-labile linker sequence

<400> SEQUENCE: 77

Gly Gly Gly Gly Ser Gly Gly Gly Gly Ser Gly Gly Gly Ser Gly
1               5                   10                  15

Gly Gly Ser Gly Gly Gly Gly Ser Gly Gly Gly Gly Ser
            20                  25                  30
```

IL-23 AND TNF-ALPHA BINDING BI-SPECIFIC HEAVY CHAIN POLYPEPTIDES

CROSS-REFERENCE TO RELATED APPLICATIONS

This application is a continuation of U.S. application Ser. No. 17/620,026, filed on Dec. 16, 2021, which is the U.S. National Stage Entry of International Application No. PCT/GB2020/051495, filed internationally on Jun. 19, 2020, which claims the benefit of European Application No. 19181870.7, filed on Jun. 21, 2019, all of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jan. 4, 2023, is named 60790_709_301_SL_3.txt and is 60,920 bytes in size.

FIELD OF THE INVENTION

The present invention relates to polypeptides comprising an immunoglobulin chain variable domain (or ICVD) which binds to interleukin-23 (IL-23) as well as to constructs and pharmaceutical compositions comprising these polypeptides. The present invention also relates to nucleic acids encoding such polypeptides, to methods for preparing such polypeptides, to cDNA and vectors comprising nucleic acids encoding such polypeptides, to host cells expressing or capable of expressing such polypeptides and to uses of such polypeptides, pharmaceutical compositions or constructs.

BACKGROUND OF THE INVENTION

IL-23 is a pleiotropic cytokine that has roles in the regulation of both physiology and pathology. IL-23 has functions associated with inflammation and immune-regulation and is considered to be important for the propagation of chronic inflammation and associated pathologies in autoimmune diseases including inflammatory bowel disease (IBD, e.g. Crohn's disease (CD) and ulcerative colitis (UC) (Croxford et al, 2012; Teng et al, 2015; Furfaro et al, 2017)). In patients with IBD, IL-23 production is increased at sites of intestinal inflammation. IL-23 orchestrates inflammation through direct effects on pathogenic T cells; IL-23 enhances the activation of IBD intraepithelial lymphocytes and NK cells and stimulates pro-inflammatory cytokine production by innate lymphoid cells (Eken et al, 2014). IL-23 is a hetero-dimeric cytokine within the IL-12 cytokine family. IL-23 and IL-12 share a common p40 subunit, which dimerizes with a ligand-specific IL-23p19 subunit (also known as p19, IL-23A and interleukin-23 subunit alpha) to form IL-23 or with IL-12p35 to form IL-12. Results of preclinical studies in different models of inflammatory bowel disease clearly demonstrate that IL-23 promotes intestinal inflammation and pathology. Although structurally related to IL-12, studies with IL-23 specific neutralising antibodies in these models have revealed that IL-23 and IL-12 have divergent roles in mucosal and systemic immune responses and that selective depletion of IL-23 can abrogate intestinal inflammation while sparing systemic immune responses.

Anti-TNF monoclonal antibodies have transformed the treatment of Crohn's disease and ulcerative colitis. By neutralizing TNF activity, antibodies such as infliximab and adalimumab promote mucosal healing and induce long-term remissions in many patients. However, approximately one-third of patients prescribed an anti-TNF agent are primary non-responders. Among the primary responders, subsequent loss of response may vary between 10 and 50% per year (secondary nonresponse) (Colombel et al. 2007; Hanauer et al. 2002, 2006; Sandborn et al. 2007; Schreiber et al. 2007). Patients with a primary nonresponse are unlikely to benefit from switching to a second anti-TNF agent; consequently, therapeutic strategies targeting other inflammatory pathways are needed.

The above suggests that IL-23 could be a therapeutic target for the treatment of IBD and also provides a rationale for local rather than systemic administration (McGovern and Powrie, 2007). Furthermore, such an agent could provide an effective treatment for IBD in circumstances where anti-TNF antibodies have failed.

WO2007005955 and WO2007027714 disclose anti-IL-23p19 antibodies.

Recently, the efficacy and safety of brazikumab (AMG-139), a fully human $IgG_2$ monoclonal antibody that selectively binds the p19 subunit of IL-23 has been investigated in patients with active CD who have failed, or were intolerant to, anti-TNFα therapy (Sandborn et al 2018, Sands et al 2017). The superiority of many polypeptides of the invention over brazikumab is demonstrated in examples 2 and 5 below.

A further anti-IL-23 agent of the prior art is 37D5, which is an anti-IL-23p19 domain antibody (VHH) (Desmyter et al 2017). The superiority of many polypeptides of the invention over 37D5 is demonstrated in example 5 below.

Polypeptides of the present invention may, in at least some embodiments, have one or more of the following advantages compared to anti-IL-23 substances of the prior art:

(i) increased affinity for IL-23;
(ii) increased specificity for IL-23;
(iii) increased neutralising capability against IL-23;
(iv) increased specificity for IL-23 over IL-12;
(v) increased cross-reactivity with IL-23 from different species such as human and cynomolgus monkey;
(vi) reduced immunogenicity, for example when administered to a mouse, cynomolgus monkey or human;
(vii) increased stability in the presence of proteases, for example (a) in the presence of proteases found in the small and/or large intestine and/or IBD inflammatory proteases, for example trypsin, chymotrypsin, MMP3, MMP10, MMP12, other MMPs and cathepsin and/or (b) in the presence of proteases from gut commensal microflora and/or pathogenic bacteria, actively secreted and/or released by lysis of microbial cells found in the small and/or large intestine;
(viii) increased stability to protease degradation during production (for example resistance to yeast proteases)
(ix) increased suitability for oral administration;
(x) increased suitability for local delivery to the intestinal tract and lamina propria following oral administration;
(xi) increased suitability for expression, in a heterologous host such as bacteria such as *Escherichia coli*, or a yeast belonging to the genera *Aspergillus, Saccharomyces, Kluyveromyces, Hansenula* or *Pichia*, such as *Saccharomyces cerevisiae* or *Pichia pastoris*;

(xii) suitability for, and improved properties for, use in a pharmaceutical; (xiii) suitability for, and improved properties for, use in a functional food;

(xiv) improved tissue penetration such as penetration of inflamed colonic mucosal epithelium and submucosal tissues to access the sub mucosal lamina propria;

(xv) decreased immunogenicity in humans for example due to increased sequence similarity to human immunoglobulins;

(xvi) increased suitability for formatting in a multispecific format;

(xvii) binding to novel epitopes.

Advantages (i) to (xvii) above may potentially be realised by the polypeptides of the present invention in a monovalent format or in a multivalent format such as a bihead format (for example homobihead or heterobihead formats).

SUMMARY OF THE INVENTION

The present inventors have produced surprisingly advantageous polypeptides comprising immunoglobulin chain variable domains which bind to IL-23. These polypeptides are the immunoglobulin chain variable domains ID-L253T, 10E2, 10G10, and polypeptides related to each of these immunoglobulin chain variable domains.

These polypeptides have been found to have unexpected advantages over prior art anti-IL-23 agents brazikumab and 37D5 (see, in particular, the background section above and examples 2 and 5 below).

These polypeptides in particular benefit from surprisingly high potency. They are also capable of cross-reacting with cynomolgus monkey IL-23 and remain stable on exposure to proteases of the small and large intestine. In one embodiment, these polypeptides have undergone further enhancement by engineering. These further enhanced polypeptides benefit from the above advantages, retain their IL-23-neutralising activity during passage through the intestinal tract and further resist degradation and/or inactivation by proteases of the intestinal tract, for example, digestive, inflammatory and microbial proteases from, for example, mammalian species.

It may be expected that these polypeptides have particular utility in the prevention or treatment of autoimmune and or inflammatory disease such as inflammatory bowel disease (for example Crohn's disease or ulcerative colitis), or in the prevention or treatment of mucositis, particularly when administered orally.

It has been found that many polypeptides of the invention have superior properties compared to brazikumab, a fully human IgG2 monoclonal antibody that selectively binds the p19 subunit of IL-23 has been investigated in patients with active CD who have failed, or were intolerant to, anti-TNFα therapy. The superiority of many polypeptides of the invention over brazikumab is demonstrated in examples 2 and 5 below.

It has also been found that many polypeptides of the invention have superior properties compared to 37D5, which is an anti-IL-23p19 domain antibody (VHH) (Desmyter et al 2017). The superiority of many polypeptides of the invention over 37D5 is demonstrated in example 5 below.

In particular embodiments, the present inventors have provided the above polypeptides in a 'bihead' format along with an anti-TNF-alpha polypeptide. The data provided herein illustrates that a therapeutic approach that combines gastrointestinal tract-restricted antagonism of IL-23 and TNF-alpha may achieve a greater degree of efficacy, for a longer duration, in a higher proportion of patients with inflammatory bowel disease, than monotherapy against either target alone.

In one aspect, the present invention provides a polypeptide comprising an immunoglobulin chain variable domain which binds to IL-23, wherein the immunoglobulin chain variable domain comprises three complementarity determining regions (CDR1-CDR3) and four framework regions (FR1-FR4), wherein CDR1 comprises a sequence sharing 60% or greater sequence identity with SEQ ID NO: 1, CDR2 comprises a sequence sharing 50% or greater sequence identity with SEQ ID NO: 2 and CDR3 comprises a sequence sharing 50% or greater sequence identity with SEQ ID NO: 3.

In a further aspect, the present invention provides a polypeptide comprising an immunoglobulin chain variable domain which binds to IL-23, wherein the immunoglobulin chain variable domain comprises three complementarity determining regions (CDR1-CDR3) and four framework regions (FR1-FR4), wherein CDR1 comprises a sequence sharing 60% or greater sequence identity with SEQ ID NO: 14 CDR2 comprises a sequence sharing 50% or greater sequence identity with SEQ ID NO: 15 and CDR3 comprises a sequence sharing 50% or greater sequence identity with SEQ ID NO: 16.

In a further aspect, the present invention provides a polypeptide comprising an immunoglobulin chain variable domain which binds to IL-23, wherein the immunoglobulin chain variable domain comprises three complementarity determining regions (CDR1-CDR3) and four framework regions (FR1-FR4), wherein CDR1 comprises a sequence sharing 60% or greater sequence identity with SEQ ID NO: 22 CDR2 comprises a sequence sharing 50% or greater sequence identity with SEQ ID NO: 23 and CDR3 comprises a sequence sharing 50% or greater sequence identity with SEQ ID NO: 24.

In a further aspect, the invention provides a construct comprising two or more identical polypeptides according to the invention.

In a further aspect, the invention provides a construct comprising at least one polypeptide according to the invention and at least one different polypeptide, wherein the different polypeptide binds to TNF-alpha.

In a further aspect, the invention provides a construct comprising at least one polypeptide according to the invention and at least one different polypeptide, wherein the different polypeptide binds to a target other than TNF-alpha.

Further aspects of the invention are disclosed elsewhere in this document.

DESCRIPTION OF THE FIGURES

FIG. 8—The polypeptide sequence of ID-L253T in Kabat format (SEQ ID NO: 8)

DESCRIPTION OF THE SEQUENCES

Figure 1:
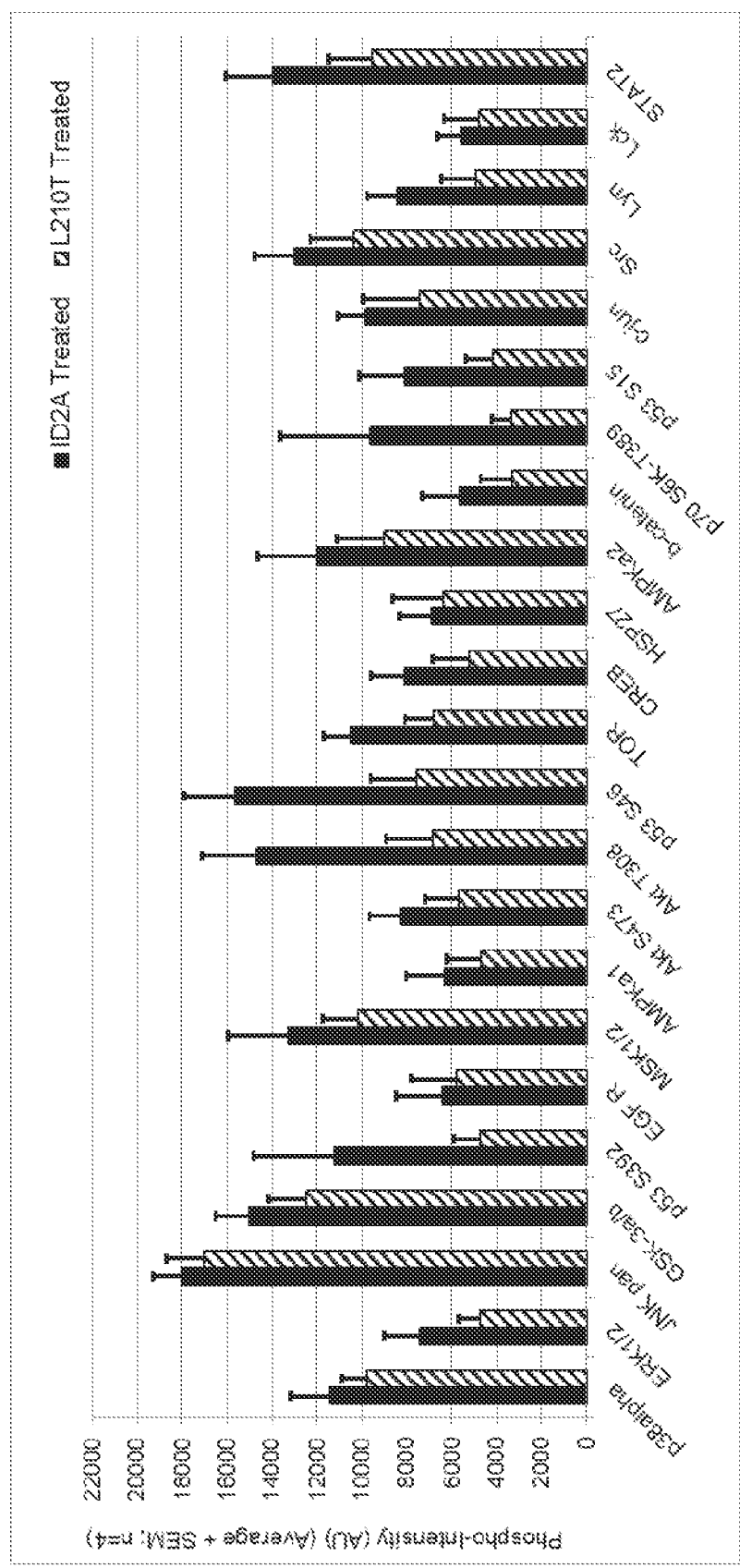
FIG. 1—Average phospho-intensity values for ex vivo UC inflamed colonic mucosal tissue treated with ID-L210T FIG. 2—Average phospho-intensity values for ex vivo UC inflamed colonic mucosal tissue treated with ID-L210T (continued)

SEQ ID NO: 1—Polypeptide sequence of ID-L253T CDR1
SEQ ID NO: 2—Polypeptide sequence of ID-L253T CDR2
SEQ ID NO: 3—Polypeptide sequence of ID-L253T CDR3
SEQ ID NO: 4—Polypeptide sequence of ID-L253T FR1
SEQ ID NO: 5—Polypeptide sequence of ID-L253T FR2
SEQ ID NO: 6—Polypeptide sequence of ID-L253T FR3
SEQ ID NO: 7—Polypeptide sequence of ID-L253T FR4
SEQ ID NO: 8—Polypeptide sequence of ID-L253T
SEQ ID NO: 9—Polynucleotide sequence encoding ID-L253T (with stop codons)
SEQ ID NO: 10—Polynucleotide sequence encoding ID-L253T (without stop codons)
SEQ ID NO: 11—Polypeptide sequence of 12G1
SEQ ID NO: 12—Polypeptide sequence of 1E2
SEQ ID NO: 13—Polypeptide sequence of 10E2
SEQ ID NO: 14—Polypeptide sequence of 10E2 CDR1
SEQ ID NO: 15—Polypeptide sequence of 10E2 CDR2
SEQ ID NO: 16—Polypeptide sequence of 10E2 CDR3
SEQ ID NO: 17—Polypeptide sequence of 10E2 FR1
SEQ ID NO: 18—Polypeptide sequence of 10E2 FR2
SEQ ID NO: 19—Polypeptide sequence of 10E2 FR3
SEQ ID NO: 20—Polypeptide sequence of 10E2 FR4
SEQ ID NO: 21—Polypeptide sequence of 10G10
SEQ ID NO: 22—Polypeptide sequence of 10G10 CDR1
SEQ ID NO: 23—Polypeptide sequence of 10G10 CDR2
SEQ ID NO: 24—Polypeptide sequence of 10G10 CDR3
SEQ ID NO: 25—Polypeptide sequence of 10G10 FR1
SEQ ID NO: 26—Polypeptide sequence of 10G10 FR2
SEQ ID NO: 27—Polypeptide sequence of 10G10 FR3
SEQ ID NO: 28—Polypeptide sequence of 10G10 FR4
SEQ ID NO: 29—Polypeptide sequence of ID-L210T
SEQ ID NO: 30—Polypeptide sequence of ID-L237T
SEQ ID NO: 31—Polypeptide sequence of ID-L238T
SEQ ID NO: 32—Polypeptide sequence of ID-L239T
SEQ ID NO: 33—Polypeptide sequence of ID-L240T
SEQ ID NO: 34—Polypeptide sequence of ID-L241T
SEQ ID NO: 35—Polypeptide sequence of ID-L242T
SEQ ID NO: 36—Polypeptide sequence of ID-L243T
SEQ ID NO: 37—Polypeptide sequence of ID-L244T
SEQ ID NO: 38—Polypeptide sequence of ID-L245T
SEQ ID NO: 39—Polypeptide sequence of ID-L246T
SEQ ID NO: 40—Polypeptide sequence of ID-L247T
SEQ ID NO: 41—Polypeptide sequence of ID-L248T
SEQ ID NO: 42—Polypeptide sequence of ID-L249T
SEQ ID NO: 43—Polypeptide sequence of ID-L250T
SEQ ID NO: 44—Polypeptide sequence of ID-L251T
SEQ ID NO: 45—Polypeptide sequence of ID-L252T
SEQ ID NO: 46—Polypeptide sequence of FA1K
SEQ ID NO: 47—Polypeptide sequence of ID-38F arm in FA1K
SEQ ID NO: 48—Polypeptide sequence of ID-L253T arm in FA1K
SEQ ID NO: 49—Polypeptide sequence of labile linker in FA1K
SEQ ID NO: 50—Polynucleotide sequence encoding ID-L210T
SEQ ID NO: 51—Polynucleotide sequence encoding ID-L237T
SEQ ID NO: 52—Polynucleotide sequence encoding ID-L238T
SEQ ID NO: 53—Polynucleotide sequence encoding ID-L239T
SEQ ID NO: 54—Polynucleotide sequence encoding ID-L240T
SEQ ID NO: 55—Polynucleotide sequence encoding ID-L241T
SEQ ID NO: 56—Polynucleotide sequence encoding ID-L242T
SEQ ID NO: 57—Polynucleotide sequence encoding ID-L243T
SEQ ID NO: 58—Polynucleotide sequence encoding ID-L244T
SEQ ID NO: 59—Polynucleotide sequence encoding ID-L245T
SEQ ID NO: 60—Polynucleotide sequence encoding ID-L246T
SEQ ID NO: 61—Polynucleotide sequence encoding ID-L247T
SEQ ID NO: 62—Polynucleotide sequence encoding ID-L248T
SEQ ID NO: 63—Polynucleotide sequence encoding ID-L249T
SEQ ID NO: 64—Polynucleotide sequence encoding ID-L250T
SEQ ID NO: 65—Polynucleotide sequence encoding ID-L251T
SEQ ID NO: 66—Polynucleotide sequence encoding ID-L252T
SEQ ID NO: 67—Polypeptide sequence of ID-38F
SEQ ID NO: 68—Polynucleotide sequence of 3' primer containing the SpeI site
SEQ ID NO: 69—Polypeptide sequence of 37D5
SEQ ID NO: 70—Brazikumab heavy chain
SEQ ID NO: 71—Brazikumab light chain
SEQ ID NO: 72—Polypeptide sequence of IL-23p19
SEQ ID NO: 73—Polypeptide sequence of IL-23p40
SEQ ID NO: 74—Polypeptide sequence of a protease-labile linker formula
SEQ ID NO: 75—Polypeptide sequence of a protease-labile linker
SEQ ID NO: 76—Polypeptide sequence of a non-protease-labile linker formula
SEQ ID NO: 77—Polypeptide sequence of a non-protease-labile linker

DETAILED DESCRIPTION OF THE INVENTION

Polypeptides Including Antibodies and Antibody Fragments Including the VH and VHH A conventional antibody or immunoglobulin (Ig) is a protein comprising four polypeptide chains: two heavy (H) chains and two light (L) chains. Each chain is divided into a constant region and a variable domain. The heavy chain variable domains are abbreviated herein as VHC, and the light (L) chain variable domains are abbreviated herein as VLC. These domains, domains related thereto and domains derived therefrom, are referred to herein as immunoglobulin chain variable domains. The VHC and VLC domains can be further subdivided into regions of hypervariability, termed "complementarity determining regions" ("CDRs"), interspersed with regions that are more conserved, termed "framework regions" ("FRs"). The framework and complementarity determining regions have been precisely defined (Kabat et al 1991). In a conventional antibody, each VHC and VLC is composed of three CDRs and four FRs, arranged from amino-terminus to carboxy-terminus in the following order: FR1, CDR1, FR2, CDR2, FR3, CDR3, FR4. The conventional antibody tetramer of two heavy immunoglobulin chains and two light immunoglobulin chains is formed with the heavy and the light immunoglobulin chains interconnected by e.g. disulfide bonds, and the heavy chains similarity connected. The heavy chain constant region includes three domains, CH1, CH2 and CH3. The light chain constant region is comprised of one domain, CL. The variable domain of the heavy chains and the variable domain of the light chains are binding domains that interact with an antigen. The constant regions of the antibodies typically mediate the binding of the antibody to host tissues or factors, including various cells of the immune system (e.g. effector cells) and the first component (C1q) of the classical complement system. The term antibody includes immunoglobulins of types IgA, IgG, IgE, IgD, IgM (as well as subtypes thereof), wherein the light chains of the immunoglobulin may be kappa or lambda types. The overall structure of immunoglobulin-gamma (IgG) antibodies assembled from two identical heavy (H)-chain and two identical light (L)-chain polypeptides is well established and highly conserved in mammals (Padlan 1994).

An exception to conventional antibody structure is found in sera of Camelidae. In addition to conventional antibodies, these sera possess special IgG antibodies. These IgG antibodies, known as heavy-chain antibodies (HCAbs), are devoid of the L chain polypeptide and lack the first constant domain (CH1). At its N-terminal region, the H chain of the homodimeric protein contains a dedicated immunoglobulin chain variable domain, referred to as the VHH, which serves to associate with its cognate antigen (Muyldermans 2013, Hamers-Casterman et al 1993, Muyldermans et al 1994).

An antigen-binding fragment (or "antibody fragment" or "immunoglobulin fragment") as used herein refers to a portion of an antibody that specifically binds to IL-23 (e.g. a molecule in which one or more immunoglobulin chains is not full length, but which specifically binds to IL-23). Examples of binding fragments encompassed within the term antigen-binding fragment include:
(i) a Fab fragment (a monovalent fragment consisting of the VLC, VHC, CL and CH1 domains);
(ii) a F(ab')2 fragment (a bivalent fragment comprising two Fab fragments linked by a disulfide bridge at the hinge region);
(iii) a Fd fragment (consisting of the VHC and CH1 domains);
(iv) a Fv fragment (consisting of the VLC and VHC domains of a single arm of an antibody);
(v) an scFv fragment (consisting of VLC and VHC domains joined, using recombinant methods, by a synthetic linker that enables them to be made as a single protein chain in which the VLC and VHC regions pair to form monovalent molecules);
(vi) a VH (an immunoglobulin chain variable domain consisting of a VHC domain (Ward et al 1989);
(vii) a VL (an immunoglobulin chain variable domain consisting of a VLC domain);
(viii) a V-NAR (an immunoglobulin chain variable domain consisting of a VHC domain from chondrichthyes IgNAR (Roux et al 1998 and Griffiths et al 2013) (ix) a VHH.

The total number of amino acid residues in a VHH or VH may be in the region of 110-130, is suitably 115-125, and is most suitably 121.

Immunoglobulin chain variable domains of the invention may for example be obtained by preparing a nucleic acid encoding an immunoglobulin chain variable domain using techniques for nucleic acid synthesis, followed by expression of the nucleic acid thus obtained According to a specific embodiment, an immunoglobulin chain variable domain of the invention does not have an amino acid sequence which is exactly the same as (i.e. shares 100% sequence identity with) the amino acid sequence of a naturally occurring polypeptide such as a VH or VHH domain of a naturally occurring antibody.

The examples provided herein relate to immunoglobulin chain variable domains per se which bind to IL-23. The principles of the invention disclosed herein are, however, equally applicable to any polypeptide comprising an immunoglobulin chain variable domain which binds to IL-23, such as antibodies and antibody fragments. For example, the anti-IL-23 immunoglobulin chain variable domains disclosed herein may be incorporated into a polypeptide such as a full length antibody. Such an approach is demonstrated by McCoy et al 2014, who provide an anti-HIV VHH engineered as a fusion with a human Fc region (including hinge, CH2 and CH3 domains), expressed as a dimer construct.

Substituting at least one amino acid residue in the framework region of a non human immunoglobulin variable domain with the corresponding residue from a human variable domain is humanisation. Humanisation of a variable domain may reduce immunogenicity in humans.

Suitably, the polypeptide of the present invention comprises an immunoglobulin chain variable domain. More suitably, the polypeptide of the present invention consists of an immunoglobulin chain variable domain, such as an immunoglobulin heavy chain variable domain. Suitably, the polypeptide of the present invention is an antibody or an antibody fragment. More suitably the polypeptide of the present invention is an antibody fragment. Suitably the antibody fragment is an immunoglobulin chain variable domain such as a VHH, a VH or a VL. Suitably the antibody fragment is a VHH, a VH, a VL, a V-NAR, an scFv, a Fab fragment, or a F(ab')2 fragment. Suitably the antibody fragment is an immunoglobulin heavy chain variable domain. More suitably the antibody fragment is a VHH or VH, and most suitably a VHH.

Specificity, Affinity, Avidity and Cross-Reactivity

Specificity refers to the number of different types of antigens or antigenic determinants to which a particular antigen-binding polypeptide can bind. The specificity of an antigen-binding polypeptide is the ability of the antigen-binding polypeptide to recognise a particular antigen as a unique molecular entity and distinguish it from another.

Affinity, represented by the equilibrium constant for the dissociation of an antigen with an antigen-binding polypeptide (Kd), is a measure of the binding strength between an antigenic determinant and an antigen-binding site on the antigen-binding polypeptide: the lesser the value of the Kd, the stronger the binding strength between an antigenic determinant and the antigen-binding polypeptide (alternatively, the affinity can also be expressed as the affinity constant (Ka), which is 1/Kd). Affinity can be determined by known methods, depending on the specific antigen of interest. Suitably, affinity is determined using a dynamically switchable biosurface (e.g. "switchSENSE®", see Knezevic et al 2012) or by surface plasmon resonance.

Avidity is the measure of the strength of binding between an antigen-binding polypeptide and the pertinent antigen. Avidity is related to both the affinity between an antigenic determinant and its antigen binding site on the antigen-binding polypeptide and the number of pertinent binding sites present on the antigen-binding polypeptide.

Suitably, polypeptide of the invention will bind to IL-23 with a dissociation constant (Kd) of $10^{-6}$ M or less, more suitably $10^{-7}$ M or less, more suitably $10^{-8}$ M or less, more suitably $10^{-8}$ M or less, more suitably $10^{-10}$ M or less, more suitably $10^{-11}$ M or less, more suitably $10^{-12}$ M or less, more suitably $10^{-13}$ M or less.

Any Kd value less than $10^{-6}$ M is considered to indicate binding. Specific binding of an antigen-binding polypeptide to an antigen or antigenic determinant can be determined in any suitable known manner, including, for example, Scatchard analysis and/or competitive binding assays, such as radioimmunoassays (RIA), enzyme immunoassays (EIA) and sandwich competition assays, and the different variants thereof known in the art. Suitably, the affinity of the polypeptide is determined by surface plasmon resonance.

In one embodiment, the affinity of the polypeptide is established at 25° C. by amine coupling an α-p40 capture antibody in a pH 5, 10 mM Sodium acetate buffer to a sensor chip. IL-23 is then immobilised on the chip by flowing either 2 µg/mL or 0.5 µg/mL at 10 µL/min for 60 seconds. This leaves the P19 subunit free to bind polypeptide. The test polypeptides are then added for 300 seconds on and 300 seconds off at 30 µl/min at five different concentrations between 0.0195 and 5 nM (L253T) or 0.8 to 500 nM (Brazikumab Fab preparation) in pH 7.4, 0.01 M HEPES, 0.15 M NaCl, 0.05% polysorbate 20 and 3 mM EDTA buffer. The bound-anti-P40 is regenerated between cycles with 10 mM Glycine, pH 2 at 10 µl/min for 60 seconds. This methodology was used in example 5.2 below.

An anti-IL-23 polypeptide, a polypeptide which interacts with IL-23, or a polypeptide against IL-23, are all effectively polypeptides which bind to IL-23. A polypeptide of the invention may bind to a linear or conformational epitope on IL-23.

Suitably, the polypeptide of the invention binds to human IL-23. More suitably, the polypeptide of the invention will bind to both human and at least one additional primate IL-23 selected from the group consisting of baboon IL-23, marmoset IL-23, cynomolgus IL-23 and rhesus IL-23. More suitably, the polypeptide of the invention binds to both human and cynomolgus IL-23.

Suitably, the polypeptide of the invention neutralises human IL-23. More suitably, the polypeptide of the invention will neutralise both human and at least one additional primate IL-23 selected from the group consisting of baboon IL-23, marmoset IL-23, cynomolgus IL-23 and rhesus IL-23. More suitably, the polypeptide of the invention neutralises both human and cynomolgus IL-23.

Suitably, IL-23 is a polypeptide comprising SEQ ID NOs: 72 (p19 subunit) and 73 (p40 subunit), more suitably IL-23 is a polypeptide consisting of SEQ ID NOs: 72 and 73. Suitably, IL-23p19 is a polypeptide comprising SEQ ID NO: 72. More suitably IL-23p19 is a polypeptide consisting of SEQ ID NO: 72. The p19 and p40 subunits used in the examples below also incorporated a single C-terminal 6×His tag each.

Polypeptides capable of reacting with IL-23 from humans and IL-23 from another species ("cross-reacting"), such as with cynomolgus monkey IL-23, are advantageous because they allow preclinical studies to be more readily performed in animal models.

Suitably the polypeptide of the invention is directed against epitopes on IL-23 that lie in and/or form part of the receptor binding site(s) of IL-23, such that said polypeptide of the invention, upon binding to IL-23, is capable inhibiting or reducing the IL-23 receptor crosslinking that is mediated by said IL-23 and/or the signal transduction that is mediated by such receptor crosslinking.

The polypeptides of the present invention bind to one or more epitope(s) on IL-23. In one aspect of the invention there is provided a polypeptide which binds to the same epitope on IL-23 as ID-L253T, 12G1, 1E2, 10E2 or 10G10; more suitably ID-L253T. Recitation of "IL-23 throughout the description may also be replaced with "p19" as appropriate, due to the polypeptide of the invention being expected to be specific for the p19 subunit of IL-23.

Suitably, the polypeptide of the invention is isolated. An "isolated" polypeptide is one that is removed from its original environment. For example, a naturally-occurring polypeptide of the invention is isolated if it is separated from some or all of the coexisting materials in the natural system.

Potency, Inhibition and Neutralisation

Potency is a measure of the activity of a therapeutic agent expressed in terms of the amount required to produce an effect of given intensity. A highly potent agent evokes a greater response at low concentrations compared to an agent of lower potency that evokes a smaller response at low concentrations. Potency is a function of affinity and efficacy. Efficacy refers to the ability of therapeutic agent to produce a biological response upon binding to a target ligand and the quantitative magnitude of this response. The term half maximal effective concentration (EC50) refers to the concentration of a therapeutic agent which causes a response halfway between the baseline and maximum after a specified exposure time. The therapeutic agent may cause inhibition or stimulation. It is commonly used, and is used herein, as a measure of potency.

A neutralising polypeptide for the purposes of the invention is a polypeptide which binds to IL-23, inhibiting the binding of IL-23 to its cognate receptor (IL-23R) as measured by ELISA, such as the ELISA described in the Examples, Evaluation Method A.

Suitably the polypeptide of the invention neutralizes human IL-23 in the IL-23-IL-23R neutralisation ELISA (see Examples, Evaluation Method A) with an EC50 of 5 nM or less, such as 4 nM or less, such as 3 nM or less, such as 2 nM or less, such as 1.7 nM or less, such as 1.5 nM or less, such as 1.4 nM or less, such as 1.3 nM or less, such as 1.2 nM or less, such as 1.1 nM or less, such as 1.0 nM or less, such as 0.9 nM or less, such as 0.8 nM or less, such as 0.75 nM or less, such as 0.70 nM or less, such as 0.65 nM or less, such as 0.60 nM or less, such as 0.55 nM or less, such as 0.50 nM or less, such as 0.45 nM or less, such as 0.40 nM or less.

Polypeptide and Polynucleotide Sequences

For the purposes of comparing two closely-related polypeptide sequences, the "% sequence identity" between a first polypeptide sequence and a second polypeptide sequence may be calculated using NCBI BLAST v2.0, using standard settings for polypeptide sequences (BLASTP). For the purposes of comparing two closely-related polynucleotide sequences, the "% sequence identity" between a first nucleotide sequence and a second nucleotide sequence may be calculated using NCBI BLAST v2.0, using standard settings for nucleotide sequences (BLASTN). The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989))

alignments (B) of 50, expectation (E) of 10, M=5, N=−4, and a comparison of both strands. The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more suitably less than about 0.01, and most suitably less than about 0.001.

Polypeptide or polynucleotide sequences are said to be the same as or identical to other polypeptide or polynucleotide sequences, if they share 100% sequence identity over their entire length. Residues in sequences are numbered from left to right, i.e. from N- to C-terminus for polypeptides; from 5' to 3' terminus for polynucleotides.

A "difference" between sequences refers to an insertion, deletion or substitution of a single amino acid residue in a position of the second sequence, compared to the first sequence. Two polypeptide sequences can contain one, two or more such amino acid differences. Insertions, deletions or substitutions in a second sequence which is otherwise identical (100% sequence identity) to a first sequence result in reduced % sequence identity. For example, if the identical sequences are 9 amino acid residues long, one substitution in the second sequence results in a sequence identity of 88.9%. If the identical sequences are 17 amino acid residues long, two substitutions in the second sequence results in a sequence identity of 88.2%. If the identical sequences are 7 amino acid residues long, three substitutions in the second sequence results in a sequence identity of 57.1%. If first and second polypeptide sequences are 9 amino acid residues long and share 6 identical residues, the first and second polypeptide sequences share greater than 66% identity (the first and second polypeptide sequences share 66.7% identity). If first and second polypeptide sequences are 17 amino acid residues long and share 16 identical residues, the first and second polypeptide sequences share greater than 94% identity (the first and second polypeptide sequences share 94.1% identity). If first and second polypeptide sequences are 7 amino acid residues long and share 3 identical residues, the first and second polypeptide sequences share greater than 42% identity (the first and second polypeptide sequences share 42.9% identity).

Alternatively, for the purposes of comparing a first, reference polypeptide sequence to a second, comparison polypeptide sequence, the number of additions, substitutions and/or deletions made to the first sequence to produce the second sequence may be ascertained. An addition is the addition of one amino acid residue into the sequence of the first polypeptide (including addition at either terminus of the first polypeptide). A substitution is the substitution of one amino acid residue in the sequence of the first polypeptide with one different amino acid residue. A deletion is the deletion of one amino acid residue from the sequence of the first polypeptide (including deletion at either terminus of the first polypeptide).

For the purposes of comparing a first, reference polynucleotide sequence to a second, comparison polynucleotide sequence, the number of additions, substitutions and/or deletions made to the first sequence to produce the second sequence may be ascertained. An addition is the addition of one nucleotide residue into the sequence of the first polynucleotide (including addition at either terminus of the first polynucleotide). A substitution is the substitution of one nucleotide residue in the sequence of the first polynucleotide with one different nucleotide residue. A deletion is the deletion of one nucleotide residue from the sequence of the first polynucleotide (including deletion at either terminus of the first polynucleotide).

A "conservative" amino acid substitution is an amino acid substitution in which an amino acid residue is replaced with another amino acid residue of similar chemical structure and which is expected to have little influence on the function, activity or other biological properties of the polypeptide. Such conservative substitutions suitably are substitutions in which one amino acid within the following groups is substituted by another amino acid residue from within the same group:

| Group | Amino acid residue |
| --- | --- |
| Non-polar aliphatic | Glycine |
| | Alanine |
| | Valine |
| | Leucine |
| | Isoleucine |
| Aromatic | Phenylalanine |
| | Tyrosine |
| | Tryptophan |
| Polar uncharged | Serine |
| | Threonine |
| | Asparagine |
| | Glutamine |
| Negatively charged | Aspartate |
| | Glutamate |
| Positively charged | Lysine |
| | Arginine |

Suitably, a hydrophobic amino acid residue is a non-polar amino acid. More suitably, a hydrophobic amino acid residue is selected from V, I, L, M, F, W or C.

As used herein, numbering of polypeptide sequences and definitions of CDRs and FRs are as defined according to the Kabat system (Kabat et al 1991). A "corresponding" amino acid residue between a first and second polypeptide sequence is an amino acid residue in a first sequence which shares the same position according to the Kabat system with an amino acid residue in a second sequence, whilst the amino acid residue in the second sequence may differ in identity from the first. Suitably corresponding residues will share the same number (and letter) if the framework and CDRs are the same length according to Kabat definition. Alignment can be achieved manually or by using, for example, a known computer algorithm for sequence alignment such as NCBI BLAST v2.0 (BLASTP or BLASTN) using standard settings.

Suitably, the polynucleotides used in the present invention are isolated. An "isolated" polynucleotide is one that is removed from its original environment. For example, a naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

In one aspect of the invention there is provided a polynucleotide encoding the polypeptide of the invention. Suitably the polynucleotide comprises or consists of a sequence sharing 70% or greater, such as 80% or greater, such as 90% or greater, such as 95% or greater, such as 99% or greater sequence identity with SEQ ID NOs: 9, 10 or 50 to 66. More suitably the polynucleotide comprises or consists of any one of SEQ ID NOs: 9, 10 or 50 to 66. In a further aspect there is provided a cDNA comprising said polynucleotide.

In one aspect of the invention there is provided a polynucleotide comprising or consisting of a sequence sharing 70% or greater, such as 80% or greater, such as 90% or greater, such as 95% or greater, such as 99% or greater sequence identity with any one of the portions of SEQ ID NOs: 9, 10 or 50 to 66 which encodes CDR1, CDR2 or CDR3 of the encoded immunoglobulin chain variable domain.

Suitably, the polypeptide sequence of the present invention contains at least one alteration with respect to a native sequence. Suitably, the polynucleotide sequences of the present invention contain at least one alteration with respect to a native sequence. Suitably the alteration to the polypeptide sequence or polynucleotide sequence is made to increase stability of the polypeptide or encoded polypeptide to proteases present in the intestinal tract (for example trypsin and chymotrypsin).

Figure 8:
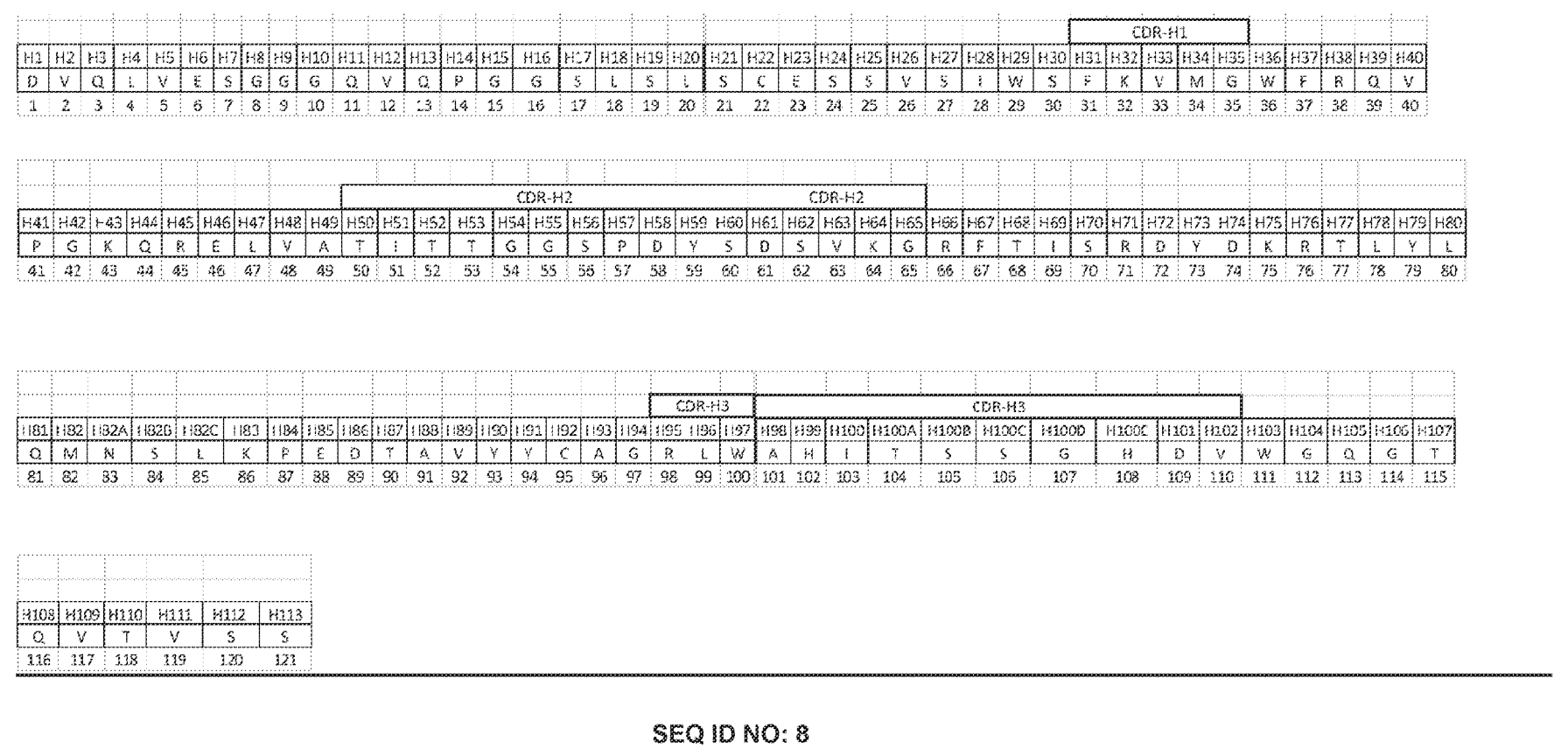

Embodiments relating to the sequences of particular polypeptides of the invention are outlined as follows.
ID-L253T and Related Polypeptides
The Polypeptide Sequence of ID-L253T in Kabat Format The polypeptide sequence of ID-L253T (SEQ ID NO: 8), a particularly advantageous polypeptide of the invention, is set out in FIG. 8 in Kabat format. CDR1 (SEQ ID NO: 1) is labelled 'CDR-H1', CDR2 (SEQ ID NO: 2) is labelled 'CDR-H2' and CDR3 (SEQ ID NO: 3) is labelled 'CDR-H3'. The top row provides Kabat numbering of each polypeptide residue (with 'H' prefix), the middle row provides polypeptide residues and the bottom row provides sequential numbering of each polypeptide residue (see FIG. 8).
CDRs of ID-L253T and Related Polypeptides Suitably CDR1 of the polypeptide of the present invention comprises or more suitably consists of a sequence sharing 80% or greater sequence identity with SEQ ID NO: 1.

Alternatively, CDR1 of the polypeptide of the present invention comprises or more suitably consists of a sequence having no more than 2, more suitably no more than 1 addition(s) compared to SEQ ID NO: 1. Suitably, CDR1 of the polypeptide of the present invention comprises or more suitably consists of a sequence having no more than 2, more suitably no more than 1 substitution(s) compared to SEQ ID NO: 1. Suitably, CDR1 of the polypeptide of the present invention comprises or more suitably consists of a sequence having no more than 2, more suitably no more than 1 deletion(s) compared to SEQ ID NO: 1.

Suitably any residues of CDR1 differing from their corresponding residues in SEQ ID NO: 1 are conservative substitutions with respect to their corresponding residues. Suitably CDR1 comprises or more suitably consists of SEQ ID NO: 1.

Suitably CDR2 of the polypeptide of the present invention comprises or more suitably consists of a sequence sharing 55% or greater, more suitably 60% or greater, more suitably 70% or greater, more suitably 75% or greater, more suitably 80% or greater, more suitably 85% or greater, more suitably 90% or greater sequence identity, with SEQ ID NO: 2.

Alternatively, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 2. Suitably, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 2. Suitably, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 2.

Suitably any residues of CDR2 differing from their corresponding residues in SEQ ID NO: 2 are conservative substitutions with respect to their corresponding residues.

Suitably the residue of CDR2 corresponding to residue number 9 of SEQ ID NO: 2 is D or H. Suitably the residue of CDR2 corresponding to residue number 10 of SEQ ID NO: 2 is Y or D. Suitably the residue of CDR2 corresponding to residue number 11 of SEQ ID NO: 2 is S, G, R or A (more suitably S, R or A, more suitably S or A). Suitably the residue of CDR2 corresponding to residue number 14 of SEQ ID NO: 2 is V or A.

Suitably the residue of CDR2 corresponding to residue number 9 of SEQ ID NO: 2 is D or H; the residue of CDR2 corresponding to residue number 10 of SEQ ID NO: 2 is Y or D; the residue of CDR2 corresponding to residue number 11 of SEQ ID NO: 2 is S, G, R or A (more suitably S, R or A, more suitably S or A) and the residue of CDR2 corresponding to residue number 14 of SEQ ID NO: 2 is V or A.

Suitably CDR2 comprises or more suitably consists of SEQ ID NO: 2.

Suitably CDR3 of the polypeptide of the present invention comprises or more suitably consists of a sequence sharing 60% or greater, more suitably 65% or greater, more suitably 75% or greater, more suitably 80% or greater, more suitably 90% or greater sequence identity with SEQ ID NO: 3.

Alternatively, CDR3 of the polypeptide of the present invention comprises or more suitably consists of a sequence having no more than 3, more suitably no more than 2, more suitably no more than 1 addition(s) compared to SEQ ID NO: 3. Suitably, CDR3 of the polypeptide of the present invention comprises or more suitably consists of a sequence having no more than 3, more suitably no more than 2, more suitably no more than 1 substitution(s) compared to SEQ ID NO: 3. Suitably, CDR3 of the polypeptide of the present invention comprises or more suitably consists of a sequence having no more than 3, more suitably no more than 2, more suitably no more than 1 deletion(s) compared to SEQ ID NO: 3. Suitably, any substitutions are conservative, with respect to their corresponding residues in SEQ ID NO: 3.

Suitably any residues of CDR3 differing from their corresponding residues in SEQ ID NO: 3 are conservative substitutions with respect to their corresponding residues.

Suitably the residue of CDR3 corresponding to residue number 6 of SEQ ID NO: 3 is I or L.

Suitably (a) the residue of CDR2 corresponding to residue number 9 of SEQ ID NO: 2 is D or H; the residue of CDR2 corresponding to residue number 10 of SEQ ID NO: 2 is Y or D; the residue of CDR2 corresponding to residue number 11 of SEQ ID NO: 2 is S, G, R or A (more suitably S, R or A, more suitably S or A) and the residue of CDR2 corresponding to residue number 14 of SEQ ID NO: 2 is V or A and (b) the residue of CDR3 corresponding to residue number 6 of SEQ ID NO: 3 is I or L.

FRs of ID-L253T and Related Polypeptides

Suitably FR1 of the polypeptide of the present invention comprises or more suitably consists of a sequence sharing 5%, 12%, 18%, 26%, 32%, 38%, 46%, 52%, 58%, 62%, 66%, 68%, 72%, 75%, 78%, 82%, 85%, 90%, 95% or greater sequence identity, with SEQ ID NO: 4.

Alternatively, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 4. Suitably, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 4. Suitably, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 4.

Suitably any residues of FR1 differing from their corresponding residues in SEQ ID NO: 4 are conservative substitutions with respect to their corresponding residues.

Suitably the residue of FR1 corresponding to residue number 1 of SEQ ID NO: 4 is D or E. Suitably the residue of FR1 corresponding to residue number 11 of SEQ ID NO: 4 is Q or L. Suitably the residue of FR1 corresponding to residue number 19 of SEQ ID NO: 4 is S or R. Suitably the residue of FR1 corresponding to residue number 23 of SEQ ID NO: 4 is E or A. Suitably the residue of FR1 corresponding to residue number 24 of SEQ ID NO: 4 is S or A.

Suitably the residue of FR1 corresponding to residue number 1 of SEQ ID NO: 4 is D or E; the residue of FR1 corresponding to residue number 11 of SEQ ID NO: 4 is Q or L; the residue of FR1 corresponding to residue number 19 of SEQ ID NO: 4 is S or R; the residue of FR1 corresponding to residue number 23 of SEQ ID NO: 4 is E or A and the residue of FR1 corresponding to residue number 24 of SEQ ID NO: 4 is S or A.

Suitably FR1 comprises or more suitably consists of SEQ ID NO: 4.

Suitably FR2 of the polypeptide of the present invention comprises or more suitably consists of a sequence sharing 10%, 15%, 25%, 30%, 40%, 45%, 55%, 60%, 70%, 75%, 85%, 90% or greater sequence identity, with SEQ ID NO: 5.

Alternatively, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 5. Suitably, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 5. Suitably, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 5.

Suitably any residues of FR2 differing from their corresponding residues in SEQ ID NO: 5 are conservative substitutions with respect to their corresponding residues.

Suitably the residue of FR2 corresponding to residue number 2 of SEQ ID NO: 5 is F or Y. Suitably the residue of FR2 corresponding to residue number 5 of SEQ ID NO: 5 is V or A. Suitably the residue of FR2 corresponding to residue number 8 of SEQ ID NO: 5 is K or H. Suitably the residue of FR2 corresponding to residue number 9 of SEQ ID NO: 5 is Q or E. Suitably the residue of FR2 corresponding to residue number 10 of SEQ ID NO: 5 is R or L. Suitably the residue of FR2 corresponding to residue number 12 of SEQ ID NO: 5 is L or F.

Suitably the residue of FR2 corresponding to residue number 2 of SEQ ID NO: 5 is F or Y; the residue of FR2 corresponding to residue number 5 of SEQ ID NO: 5 is V or A; the residue of FR2 corresponding to residue number 8 of SEQ ID NO: 5 is K or H; the residue of FR2 corresponding to residue number 9 of SEQ ID NO: 5 is Q or E; the residue of FR2 corresponding to residue number 10 of SEQ ID NO: 5 is R or L and the residue of FR2 corresponding to residue number 12 of SEQ ID NO: 5 is L or F.

Suitably FR3 of the polypeptide of the present invention comprises or more suitably consists of a sequence sharing 8%, 15%, 20%, 26%, 32%, 40%, 45%, 52%, 58%, 65%, 70%, 76%, 80%, 82%, 85%, 90%, 92%, 95% or greater sequence identity, with SEQ ID NO: 6.

Alternatively, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 addition(s) compared to SEQ ID NO: 6. Suitably, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 6. Suitably, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 6.

Suitably the residue of FR3 corresponding to residue number 4 of SEQ ID NO: 6 is I, L or M (more suitably I or M). Suitably the residue of FR3 corresponding to residue number 13 of SEQ ID NO: 6 is L or V. Suitably the residue of FR3 corresponding to residue number 14 of SEQ ID NO: 6 is Y or F. Suitably the residue of FR3 corresponding to residue number 16 of SEQ ID NO: 6 is Q or E. Suitably the residue of FR3 corresponding to residue number 18 of SEQ ID NO: 6 is N or D. Suitably the residue of FR3 corresponding to residue number 20 of SEQ ID NO: 6 is L or V. Suitably the residue of FR3 corresponding to residue number 22 of SEQ ID NO: 6 is P or S. Suitably the residue of FR3 corresponding to residue number 25 of SEQ ID NO: 6 is T or A. Suitably the residue of FR3 corresponding to residue number 27 of SEQ ID NO: 6 is V or R. Suitably the residue of FR3 corresponding to residue number 31 of SEQ ID NO: 6 is A or N.

Suitably the residue of FR3 corresponding to residue number 4 of SEQ ID NO: 6 is I, L or M (more suitably I or M); the residue of FR3 corresponding to residue number 13 of SEQ ID NO: 6 is L or V; the residue of FR3 corresponding to residue number 14 of SEQ ID NO: 6 is Y or F; the residue of FR3 corresponding to residue number 16 of SEQ ID NO: 6 is Q or E; the residue of FR3 corresponding to residue number 18 of SEQ ID NO: 6 is N or D; the residue of FR3 corresponding to residue number 20 of SEQ ID NO: 6 is L or V; the residue of FR3 corresponding to residue number 22 of SEQ ID NO: 6 is P or S; the residue of FR3 corresponding to residue number 25 of SEQ ID NO: 6 is T or A; the residue of FR3 corresponding to residue number 27 of SEQ ID NO: 6 is V or R and the residue of FR3 corresponding to residue number 31 of SEQ ID NO: 6 is A or N.

Suitably any residues of FR3 differing from their corresponding residues in SEQ ID NO: 6 are conservative substitutions with respect to their corresponding residues. Suitably FR3 comprises or more suitably consists of SEQ ID NO: 6.

Suitably FR4 of the polypeptide of the present invention comprises or more suitably consists of a sequence sharing 5%, 10%, 20%, 30%, 40%, 50%, 60%, 70%, 80%, 90% or greater sequence identity, with SEQ ID NO: 7.

Alternatively, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 7. Suitably, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 7. Suitably, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 7.

Suitably any residues of FR4 differing from their corresponding residues in SEQ ID NO: 7 are conservative substitutions with respect to their corresponding residues. Suitably FR4 comprises or more suitably consists of SEQ ID NO: 7.

Suitably the residue of FR4 corresponding to residue number 6 of SEQ ID NO: 7 is Q or R.

Full Length Sequences of ID-L253T and Related Polypeptides

Suitably the polypeptide of the present invention comprises or more suitably consists of a sequence sharing 50% or greater, more suitably 55% or greater, more suitably 60% or greater, more suitably 65% or greater, more suitably 70% or greater, more suitably 75% or greater, more suitably 80% or greater, more suitably 85% or greater, more suitably 90% or greater, more suitably 95% or greater, more suitably 96% or greater, more suitably 97% or greater, more suitably 98% or greater, more suitably 99% or greater sequence identity, with SEQ ID NO: 8.

Alternatively, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 8. Suitably, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 8. Suitably, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 8.

Suitably the N-terminus of the polypeptide is D. Suitably the polypeptide comprises or more suitably consists of SEQ ID NO: 8.

10E2 and Related Polypeptides

CDRs of 10E2 and Related Polypeptides

Suitably CDR1 of the polypeptide of the present invention comprises or more suitably consists of a sequence sharing 80% or greater sequence identity with SEQ ID NO: 14.

Alternatively, CDR1 of the polypeptide of the present invention comprises or more suitably consists of a sequence having no more than 2, more suitably no more than 1 addition(s) compared to SEQ ID NO: 14. Suitably, CDR1 of the polypeptide of the present invention comprises or more suitably consists of a sequence having no more than 2, more suitably no more than 1 substitution(s) compared to SEQ ID NO: 14. Suitably, CDR1 of the polypeptide of the present invention comprises or more suitably consists of a sequence having no more than 2, more suitably no more than 1 deletion(s) compared to SEQ ID NO: 14.

Suitably any residues of CDR1 differing from their corresponding residues in SEQ ID NO: 14 are conservative substitutions with respect to their corresponding residues. Suitably CDR1 comprises or more suitably consists of SEQ ID NO: 14.

Suitably CDR2 of the polypeptide of the present invention comprises or more suitably consists of a sequence sharing 55% or greater, more suitably 60% or greater, more suitably 70% or greater, more suitably 75% or greater, more suitably 80% or greater, more suitably 85% or greater, more suitably 90% or greater sequence identity, with SEQ ID NO: 15.

Alternatively, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 15. Suitably, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 15. Suitably, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 15.

Suitably any residues of CDR2 differing from their corresponding residues in SEQ ID NO: 15 are conservative substitutions with respect to their corresponding residues.

Suitably CDR2 comprises or more suitably consists of SEQ ID NO: 15.

Suitably CDR3 of the polypeptide of the present invention comprises or more suitably consists of a sequence sharing 60% or greater, more suitably 65% or greater, more suitably 75% or greater, more suitably 80% or greater, more suitably 90% or greater sequence identity with SEQ ID NO: 16.

Alternatively, CDR3 of the polypeptide of the present invention comprises or more suitably consists of a sequence having no more than 3, more suitably no more than 2, more suitably no more than 1 addition(s) compared to SEQ ID NO: 16. Suitably, CDR3 of the polypeptide of the present invention comprises or more suitably consists of a sequence having no more than 3, more suitably no more than 2, more suitably no more than 1 substitution(s) compared to SEQ ID NO: 16. Suitably, CDR3 of the polypeptide of the present invention comprises or more suitably consists of a sequence having no more than 3, more suitably no more than 2, more suitably no more than 1 deletion(s) compared to SEQ ID NO: 16. Suitably, any substitutions are conservative, with respect to their corresponding residues in SEQ ID NO: 16.

Suitably any residues of CDR3 differing from their corresponding residues in SEQ ID NO: 16 are conservative substitutions with respect to their corresponding residues.

FRs of 10E2 and Related Polypeptides

Suitably FR1 of the polypeptide of the present invention comprises or more suitably consists of a sequence sharing 5%, 12%, 18%, 26%, 32%, 38%, 46%, 52%, 58%, 62%, 66%, 68%, 72%, 75%, 78%, 82%, 85%, 90%, 95% or greater sequence identity, with SEQ ID NO: 17.

Alternatively, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 17. Suitably, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 17. Suitably, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 17.

Suitably any residues of FR1 differing from their corresponding residues in SEQ ID NO: 17 are conservative substitutions with respect to their corresponding residues.

Suitably FR1 comprises or more suitably consists of SEQ ID NO: 17.

Suitably FR2 of the polypeptide of the present invention comprises or more suitably consists of a sequence sharing 10%, 15%, 25%, 30%, 40%, 45%, 55%, 60%, 70%, 75%, 85%, 90% or greater sequence identity, with SEQ ID NO: 18.

Alternatively, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 18. Suitably, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 18. Suitably, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 18.

Suitably any residues of FR2 differing from their corresponding residues in SEQ ID NO: 18 are conservative substitutions with respect to their corresponding residues.

Suitably FR3 of the polypeptide of the present invention comprises or more suitably consists of a sequence sharing 8%, 15%, 20%, 26%, 32%, 40%, 45%, 52%, 58%, 65%, 70%, 76%, 80%, 82%, 85%, 90%, 92%, 95% or greater sequence identity, with SEQ ID NO: 19.

Alternatively, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 addition(s) compared to SEQ ID NO: 19. Suitably, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 19. Suitably, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 19.

Suitably any residues of FR3 differing from their corresponding residues in SEQ ID NO: 19 are conservative substitutions with respect to their corresponding residues.

Suitably FR3 comprises or more suitably consists of SEQ ID NO: 19.

Suitably FR4 of the polypeptide of the present invention comprises or more suitably consists of a sequence sharing 5%, 10%, 20%, 30%, 40%, 50%, 60%, 70%, 80%, 90% or greater sequence identity, with SEQ ID NO: 20.

Alternatively, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 20. Suitably, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 20. Suitably, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 20.

Suitably any residues of FR4 differing from their corresponding residues in SEQ ID NO: 20 are conservative substitutions with respect to their corresponding residues.

Suitably FR4 comprises or more suitably consists of SEQ ID NO: 20.

Full Length Sequences of 10E2 and Related Polypeptides

Suitably the polypeptide of the present invention comprises or more suitably consists of a sequence sharing 50% or greater, more suitably 55% or greater, more suitably 60% or greater, more suitably 65% or greater, more suitably 70% or greater, more suitably 75% or greater, more suitably 80% or greater, more suitably 85% or greater, more suitably 90% or greater, more suitably 95% or greater, more suitably 96% or greater, more suitably 97% or greater, more suitably 98% or greater, more suitably 99% or greater sequence identity, with SEQ ID NO: 13.

Alternatively, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 13. Suitably, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 13. Suitably, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 13.

Suitably the N-terminus of the polypeptide is D. Suitably the polypeptide comprises or more suitably consists of SEQ ID NO: 13.

10G10 and Related Polypeptides

CDRs of 10G10 and Related Polypeptides

Suitably CDR1 of the polypeptide of the present invention comprises or more suitably consists of a sequence sharing 80% or greater sequence identity with SEQ ID NO: 22

Alternatively, CDR1 of the polypeptide of the present invention comprises or more suitably consists of a sequence having no more than 2, more suitably no more than 1 addition(s) compared to SEQ ID NO: 22. Suitably, CDR1 of the polypeptide of the present invention comprises or more suitably consists of a sequence having no more than 2, more suitably no more than 1 substitution(s) compared to SEQ ID NO: 22. Suitably, CDR1 of the polypeptide of the present invention comprises or more suitably consists of a sequence having no more than 2, more suitably no more than 1 deletion(s) compared to SEQ ID NO: 22.

Suitably any residues of CDR1 differing from their corresponding residues in SEQ ID NO: 22 are conservative substitutions with respect to their corresponding residues. Suitably CDR1 comprises or more suitably consists of SEQ ID NO: 22.

Suitably CDR2 of the polypeptide of the present invention comprises or more suitably consists of a sequence sharing 55% or greater, more suitably 60% or greater, more suitably 70% or greater, more suitably 75% or greater, more suitably 80% or greater, more suitably 85% or greater, more suitably 90% or greater sequence identity, with SEQ ID NO: 23.

Alternatively, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 23. Suitably, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 23. Suitably, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 23.

Suitably any residues of CDR2 differing from their corresponding residues in SEQ ID NO: 23 are conservative substitutions with respect to their corresponding residues.

Suitably CDR2 comprises or more suitably consists of SEQ ID NO: 23.

Suitably CDR3 of the polypeptide of the present invention comprises or more suitably consists of a sequence sharing 60% or greater, more suitably 65% or greater, more suitably 75% or greater, more suitably 80% or greater, more suitably 90% or greater sequence identity with SEQ ID NO: 24.

Alternatively, CDR3 of the polypeptide of the present invention comprises or more suitably consists of a sequence having no more than 3, more suitably no more than 2, more suitably no more than 1 addition(s) compared to SEQ ID NO: 24. Suitably, CDR3 of the polypeptide of the present invention comprises or more suitably consists of a sequence having no more than 3, more suitably no more than 2, more suitably no more than 1 substitution(s) compared to SEQ ID NO: 24. Suitably, CDR3 of the polypeptide of the present invention comprises or more suitably consists of a sequence having no more than 3, more suitably no more than 2, more suitably no more than 1 deletion(s) compared to SEQ ID NO: 24. Suitably, any substitutions are conservative, with respect to their corresponding residues in SEQ ID NO: 24.

Suitably any residues of CDR3 differing from their corresponding residues in SEQ ID NO: 24 are conservative substitutions with respect to their corresponding residues.

FRs of 10G10 and Related Polypeptides

Suitably FR1 of the polypeptide of the present invention comprises or more suitably consists of a sequence sharing 5%, 12%, 18%, 26%, 32%, 38%, 46%, 52%, 58%, 62%, 66%, 68%, 72%, 75%, 78%, 82%, 85%, 90%, 95% or greater sequence identity, with SEQ ID NO: 25.

Alternatively, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 25. Suitably, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 25. Suitably, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 25.

Suitably any residues of FR1 differing from their corresponding residues in SEQ ID NO: 25 are conservative substitutions with respect to their corresponding residues.

Suitably FR1 comprises or more suitably consists of SEQ ID NO: 25.

Suitably FR2 of the polypeptide of the present invention comprises or more suitably consists of a sequence sharing 10%, 15%, 25%, 30%, 40%, 45%, 55%, 60%, 70%, 75%, 85%, 90% or greater sequence identity, with SEQ ID NO: 26.

Alternatively, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 26. Suitably, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 26. Suitably, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 26.

Suitably any residues of FR2 differing from their corresponding residues in SEQ ID NO: 26 are conservative substitutions with respect to their corresponding residues.

Suitably FR3 of the polypeptide of the present invention comprises or more suitably consists of a sequence sharing 8%, 15%, 20%, 26%, 32%, 40%, 45%, 52%, 58%, 65%, 70%, 76%, 80%, 82%, 85%, 90%, 92%, 95% or greater sequence identity, with SEQ ID NO: 27.

Alternatively, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 addition(s) compared to SEQ ID NO: 27. Suitably, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 27. Suitably, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 27.

Suitably any residues of FR3 differing from their corresponding residues in SEQ ID NO: 27 are conservative substitutions with respect to their corresponding residues. Suitably FR3 comprises or more suitably consists of SEQ ID NO: 27.

Suitably FR4 of the polypeptide of the present invention comprises or more suitably consists of a sequence sharing 5%, 10%, 20%, 30%, 40%, 50%, 60%, 70%, 80%, 90% or greater sequence identity, with SEQ ID NO: 28.

Alternatively, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 28. Suitably, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 28. Suitably, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 28.

Suitably any residues of FR4 differing from their corresponding residues in SEQ ID NO: 28 are conservative substitutions with respect to their corresponding residues. Suitably FR4 comprises or more suitably consists of SEQ ID NO: 28.

Full Length Sequences of 10G10 and Related Polypeptides

Suitably the polypeptide of the present invention comprises or more suitably consists of a sequence sharing 50% or greater, more suitably 55% or greater, more suitably 60% or greater, more suitably 65% or greater, more suitably 70% or greater, more suitably 75% or greater, more suitably 80% or greater, more suitably 85% or greater, more suitably 90% or greater, more suitably 95% or greater, more suitably 96% or greater, more suitably 97% or greater, more suitably 98% or greater, more suitably 99% or greater sequence identity, with SEQ ID NO: 21.

Alternatively, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 21. Suitably, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 21. Suitably, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 21.

Suitably the N-terminus of the polypeptide is D. Suitably the polypeptide comprises or more suitably consists of SEQ ID NO: 21.

Further Embodiments Relating to ID-L253T, 10E2, 10G10 and Related Polypeptides

In one embodiment, there is provided a polypeptide comprising an immunoglobulin chain variable domain which binds to IL-23, wherein the immunoglobulin chain variable domain comprises three complementarity determining regions (CDR1-CDR3) and four framework regions (FR1-FR4), wherein the complementarity determining regions (and more suitably the framework regions) are selected from the complementarity determining regions (and framework regions) disclosed herein.

In one embodiment, there is provided a polypeptide comprising an immunoglobulin chain variable domain which binds to IL-23, wherein the immunoglobulin chain variable domain comprises three complementarity determining regions (CDR1-CDR3) and four framework regions (FR1-FR4), wherein:

CDR1 comprises a sequence selected from SEQ ID NO: 1, SEQ ID NO: 14, or SEQ ID NO: 22;
CDR2 comprises a sequence selected from SEQ ID NO: 2, SEQ ID NO: 15, or SEQ ID NO: 23;
CDR3 comprises a sequence selected from SEQ ID NO: 3, SEQ ID NO: 16 or SEQ ID NO: 24.

Suitably the polypeptide disclosed herein comprises or more suitably consists of a sequence sharing 70% or greater, more suitably 80% or greater, more suitably 90% or greater, more suitably 95% or greater, more suitably 98% or greater, more suitably 99% or greater, more suitably 99.5% or greater sequence identity with any one of SEQ ID Nos: 8, 11, 12, 13, 21 or 29-45.

In one embodiment there is provided a polypeptide comprising or more suitably consisting of a sequence sharing 70% or greater, more suitably 80% or greater, more suitably 90% or greater, more suitably 95% or greater, more suitably 98% or greater, more suitably 99% or greater, more suitably 99.5% or greater sequence identity with any one of SEQ ID Nos: 8, 11, 12, 13, 21 or 29-45.

Linkers and Multimers

A construct according to the invention comprises multiple polypeptides and therefore may suitably be multivalent. Such a construct may comprise at least two identical polypeptides according to the invention. A construct consisting of two identical polypeptides according to the invention is a "homobihead". In one aspect of the invention there is provided a construct comprising two or more identical polypeptides of the invention.

Alternatively, a construct may comprise at least two polypeptides which are different, but are both still polypeptides according to the invention (a "heterobihead").

Alternatively, such a construct may comprise (a) at least one polypeptide according to the invention and (b) at least one polypeptide such as an antibody or antigen-binding fragment thereof, which is not a polypeptide of the invention (also a "heterobihead"). The at least one polypeptide of (b) may bind IL-23 (for example via a different epitope to that of (a)), or alternatively may bind to a target other than IL-23. Suitably the different polypeptide (b) binds to, for example: an interleukin (such as IL-1, IL-1ra, IL-4, IL-5, IL-6, IL-7, IL-8, IL-9, IL-10, IL-11, IL-12, IL-13, IL-15, IL-17 and IL-18), an interleukin receptor (such as IL-6R and IL-7R), a transcription factor (such as NF-kB), a cytokine (such as TNF-alpha, IFN-gamma TGF-beta and TSLP), a transmembrane protein (such as gp130 and CD3), a surface glycoprotein (such as CD4, CD20, CD40), a soluble protein (such as CD40L), an integrin (such as a4b7 and AlphaEbeta7), an adhesion molecule (such as MAdCAM), a chemokine (such as IP10 and CCL20), a chemokine receptor (such as CCR2 and CCR9), an inhibitory protein (such as SMAD7), a kinase (such as JAK3), a G protein-coupled receptor (such as sphingosine-1-P receptor), other inflammatory mediators or immunologically relevant ligands involved in human pathological processes. Thus the different polypeptide (b) binds to, for example, IL-6R, IL-6, IL-12, IL-1-beta, IL-17A, TNF-alpha or CD3; or other inflammatory mediators or immunologically relevant ligands involved in human pathological processes. Most suitably, the different polypeptide (b) binds to TNF-alpha, more suitably the different polypeptide (b) is ID-38F.

Constructs can be multivalent and/or multispecific. A multivalent construct (such as a bivalent construct) comprises two or more binding polypeptides therefore presents two or more sites at which attachment to one or more antigens can occur. An example of a multivalent construct could be a homobihead or a heterobihead. A multispecific construct (such as a bispecific construct) comprises two or more different binding polypeptides which present two or more sites at which either (a) attachment to two or more different antigens can occur or (b) attachment to two or more different epitopes on the same antigen can occur. An example of a multispecific construct could be a heterobihead. A multispecific construct is multivalent.

Suitably, the polypeptides comprised within the construct are antibody fragments. More suitably, the polypeptides comprised within the construct are selected from the list consisting of: VHH, a VH, a VL, a V-NAR, an scFv, a Fab fragment, or a F(ab')2 fragment. More suitably, the polypeptides comprised within the construct are VHs or VHHs, most suitably VHHs.

The polypeptides of the invention can be linked to each other directly (i.e. without use of a linker) or via a linker. Suitably, the linker is a protease-labile ('a labile linker') or a non-protease-labile linker. The linker is suitably a polypeptide and will be selected so as to allow binding of the polypeptides to their epitopes. If used for therapeutic purposes, the linker is suitably non-immunogenic in the subject to which the polypeptides are administered.

Suitably the protease-labile linker is of the format:

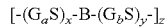

wherein
a is 1 to 10;
b is 1 to 10;
x is 1 to 10;
y is 1 to 10;
z is 1 to 10 and
B is K or R (SEQ ID NO: 74).
and more suitably:

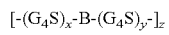

wherein
x is 1 to 10;
y is 1 to 10
z is 1 to 10 and
B is K or R.

More suitably a is 2 to 5, b is 2 to 5, x is 1 to 3, y is 1 to 3, z is 1 and B is K.

More suitably the protease-labile linker is of the format $-(G_4S)_2-K-(G_4S)_2-$ (SEQ ID NO: 75).

Suitably the polypeptides are all connected by non-protease-labile linkers. Suitably non-protease-labile linkers are of the format $(G_4S)_x$ wherein x is 1 to 10 (SEQ ID NO: 76). Most suitably x is 6 (SEQ ID NO: 77).

Accordingly, there is provided a construct comprising at least one polypeptide according to the invention and at least one different polypeptide, wherein the different polypeptide binds to TNF-alpha. Suitably the polypeptide which binds to TNF-alpha is ID-38F or a variant thereof, such as a polypeptide sharing at least 70% sequence identity, such as at least 80% sequence identity, such as at least 90% sequence identity, such as at least 95% sequence identity, such as at least 99% sequence identity with ID-38F (SEQ ID NO: 67). More suitably, the polypeptide which binds to TNF-alpha is ID-38F. In one embodiment, this construct comprises a non-protease-labile linker, such as $(G_4S)_6$. Alternatively, this construct comprises a protease-labile linker, such as $-(G_4S)_2-K-(G_4S)_2-$. Suitably, this construct shares at least 80%, such as at least 90%, such as at least 95% sequence identity with FA1K (SEQ ID NO: 46).

In embodiments wherein the construct comprises a non-protease-labile linker, then suitably the construct as a whole (i.e. the binding polypeptides (which may be immunoglobulin chain variable domains) and the non-protease-labile linker) is substantially resistant to proteases such as trypsin and chymotrypsin. In embodiments wherein the construct comprises a protease-labile linker, then suitably the polypeptides (i.e. the binding polypeptides, which may be immunoglobulin chain variable domains) are substantially resistant to proteases such as trypsin and chymotrypsin but the protease-labile linker is labile to proteases such as trypsin or chymotrypsin.

Vectors and Hosts

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian and yeast vectors). Other vectors (e.g. non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g. replication defective retroviruses. adenoviruses and adeno-associated viruses), which serve equivalent functions, and also bacteriophage and phagemid systems. The invention also relates to nucleotide sequences that encode polypeptide sequences or multivalent and/or multispecific constructs. The term "recombinant host cell" (or simply "host cell"), as used herein, is intended to refer to a cell into which a recombinant expression vector has been introduced. Such terms are intended to refer not only to the particular subject cell but to the progeny of such a cell.

In one aspect of the invention there is provided a vector comprising the polynucleotide encoding the polypeptide or construct of the invention or cDNA comprising said polynucleotide. In a further aspect of the invention there is provided a host cell transformed with said vector, which is capable of expressing the polypeptide or construct of the invention. Suitably the host cell is a bacterium such as *Escherichia coli*, a yeast belonging to the genera *Aspergillus, Saccharomyces, Kluyveromyces, Hansenula* or *Pichia*, such as *Saccharomyces cerevisiae* or *Pichia pastoris*.

Stability

Suitably, the polypeptide or construct of the present invention substantially retains neutralisation ability and/or potency when delivered orally and after exposure to the intestinal tract (for example, after exposure to proteases of the small and/or large intestine and/or IBD inflammatory proteases). Such proteases include enteropeptidase, trypsin, chymotrypsin, and irritable bowel disease inflammatory proteases (such as MMP3, MMP12 and cathepsin). Proteases of, or produced in, the small and/or large intestine include proteases sourced from intestinal commensal microflora and/or pathogenic bacteria, for example wherein the proteases are cell membrane-attached proteases, excreted proteases and proteases released on cell lysis). Most suitably the proteases are trypsin and chymotrypsin.

Suitably the intestinal tract is the intestinal tract of a dog, pig, human, cynomolgus monkey or mouse. More suitably the intestinal tract is the intestinal tract of a human, cynomolgus monkey or mouse, more suitably a mouse or human, most suitably a human. The small intestine suitably consists of the duodenum, jejunum and ileum. The large intestine suitably consists of the cecum, colon, rectum and anal canal.

The intestinal tract, as opposed to the gastrointestinal tract, consists of only the small intestine and the large intestine.

The polypeptide or construct of the present invention substantially retains neutralisation ability when suitably 10% or more, more suitably 20% or more, more suitably 30% or more, more suitably 40% or more, more suitably 50% or more, more suitably 60% or more, more suitably 70% or more, more suitably 80% or more, more suitably 90% or more, more suitably 95% or more, or most suitably 100% of the original neutralisation ability of the polypeptide of the invention or construct is retained after exposure to proteases present in the small and/or large intestine and/or IBD inflammatory proteases.

Suitably the polypeptide or construct of the invention substantially retains neutralisation ability after exposure to proteases present in the small and/or large intestine and/or IBD inflammatory proteases for, for example, up to at least 1, more suitably up to at least 2, more suitably up to at least 3, more suitably up to at least 4, more suitably up to at least 7, more suitably up to at least 16 hours at 37° C.

By 'substantially retains neutralisation ability' it is suitably meant that the polypeptide or construct of the invention retains 10% or more, more suitably 20% or more, more suitably 30% or more, more suitably 40% or more, more suitably 50% or more, more suitably 60% or more, more suitably 70% or more, more suitably 80% or more, more suitably 90% or more of the neutralisation ability of the polypeptide or construct of the invention.

Suitably 10% or more, more suitably 20% or more, more suitably 30% or more, more suitably 40% or more, more suitably 50% or more, more suitably 60% or more, more suitably 70% or more of the neutralisation ability of the polypeptide or construct of the invention is retained after 4 hours of exposure to conditions of the intestinal tract, more suitably the small or large intestine, more suitably human faecal extract.

Suitably 10% or more, more suitably 20% or more, more suitably 30% or more, more suitably 40% or more, more suitably 50% or more, more suitably 60% or more, more suitably 70% or more of the neutralisation ability of the polypeptide or construct of the invention is retained after 7 hours of exposure to conditions of the intestinal tract, more suitably the small or large intestine, more suitably human faecal extract.

Suitably 10% or more, more suitably 20% or more, more suitably 30% or more, more suitably 40% or more, more suitably 50% or more, more suitably 60% or more, more suitably 70% or more of the neutralisation ability of the polypeptide or construct of the invention is retained after 16 hours of exposure to conditions of the intestinal tract, more suitably the small or large intestine, more suitably human faecal extract.

Suitably 10% or more, more suitably 20% or more, more suitably 30% or more, more suitably 40% or more, more suitably 50% or more, more suitably 60% or more, more suitably 70% or more of the neutralisation ability of the polypeptide or construct of the invention is retained after 1 hour of exposure to conditions of the intestinal tract, more suitably the small or large intestine, more suitably mouse small intestinal supernatant.

Suitably 10% or more, more suitably 20% or more, more suitably 30% or more, more suitably 40% or more, more suitably 50% or more, more suitably 60% or more, more suitably 70% or more of the neutralisation ability of the polypeptide or construct of the invention is retained after 4 hours of exposure to conditions of the intestinal tract, more suitably the small or large intestine, more suitably mouse small intestinal supernatant.

Suitably 10% or more, more suitably 20% or more, more suitably 30% or more, more suitably 40% or more, more suitably 50% or more, more suitably 60% or more, more suitably 70% or more of the administered dose of polypeptides or constructs of the invention retain neutralisation ability against IL-23 and remain in the faeces of a mouse, cynomolgus monkey and/or human (suitably excreted faeces or faeces removed from the intestinal tract) after 1, 2, 3, 4, 5, 6 or 7 hours of exposure to conditions of the intestinal tract.

A polypeptide of the invention or construct of the invention remains substantially intact when suitably 10% or more, more suitably 20% or more, more suitably 30% or more, more suitably 40% or more, more suitably 50% or more, more suitably 60% or more, more suitably 70% or more, more suitably 80% or more, more suitably 90% or more, more suitably 95% or more, more suitably 99% or more, most suitably 100% of the administered quantity of polypeptide of the invention or construct remains intact after exposure to proteases present in the small and/or large intestine and/or IBD inflammatory proteases.

Therapeutic Use and Delivery

A therapeutically effective amount of a polypeptide, pharmaceutical composition or construct of the invention, is an amount which is effective, upon single or multiple dose administration to a subject, in neutralising IL-23 to a significant extent in a subject. A therapeutically effective amount may vary according to factors such as the disease state, age, sex, and weight of the individual, and the ability of the polypeptide, pharmaceutical composition or construct to elicit a desired response in the individual. A therapeutically effective amount is also one in which any toxic or detrimental effects of the polypeptide of the invention, pharmaceutical composition or construct are outweighed by the therapeutically beneficial effects. The polypeptide or construct of the invention can be incorporated into pharmaceutical compositions suitable for administration to a subject. The polypeptide or construct of the invention can be in the form of a pharmaceutically acceptable salt.

A pharmaceutical composition of the invention may suitably be formulated for oral, intramuscular, subcutaneous or intravenous delivery. The pharmaceutical compositions of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. Solid dosage forms are preferred. The polypeptide of the invention, pharmaceutical composition or construct may be incorporated with excipients and used in the form of ingestible tablets, buccal tablets, troches, capsules, elixirs, suspensions, syrups, wafers, and the like.

Typically, the pharmaceutical composition comprises a polypeptide or construct of the invention and a pharmaceutically acceptable diluent or carrier. Examples of pharmaceutically acceptable carriers include one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the polypeptide or construct of the invention. Pharmaceutical compositions may include antiadherents, binders, coatings, disintegrants, flavours, colours, lubricants, sorbents, preservatives, sweeteners, freeze dry excipients (including lyoprotectants) or compression aids.

Most suitably, the polypeptide, pharmaceutical composition or construct of the invention is administered orally. A key problem with oral delivery is ensuring that sufficient polypeptide, pharmaceutical composition or construct reaches the area of the intestinal tract where it is required. Factors which prevent a polypeptide, pharmaceutical composition or construct of the invention reaching the area of the intestinal tract where it is required include the presence of proteases in digestive secretions which may degrade a polypeptide, pharmaceutical composition or construct of the invention. Suitably, the polypeptide, pharmaceutical composition or construct of the invention are substantially stable in the presence of one or more of such proteases by virtue of the inherent properties of the polypeptide or construct itself. Suitably, the polypeptide or construct of the invention is lyophilised before being incorporated into a pharmaceutical composition.

A polypeptide of the invention may also be provided with an enteric coating. An enteric coating is a polymer barrier applied on oral medication which helps to protect the polypeptide from the low pH of the stomach. Materials used for enteric coatings include fatty acids, waxes, shellac, plastics, and plant fibers. Suitable enteric coating components include methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate and stearic acid. Suitable enteric coatings include pH-dependent release polymers. These are polymers which are insoluble at the highly acidic pH found in the stomach, but which dissolve rapidly at a less acidic pH. Thus, suitably, the enteric coating will not dissolve in the acidic juices of the stomach (pH ~3), but will do so in the higher pH environment present in the small intestine (pH above 6) or in the colon (pH above 7.0). The pH-dependent release polymer is selected such that the polypeptide or construct of the invention will be released at about the time that the dosage reaches the small intestine.

A polypeptide, construct or pharmaceutical composition of the invention can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilisers, isotonic agents, suspending agents, emulsifying agents, stabilisers and preservatives. Acceptable carriers, excipients and/or stabilisers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as polysorbates, POE ethers, poloxamers, Triton-X, or polyethylene glycol.

A pharmaceutical composition of the invention may be delivered topically to the skin (for example for use in the treatment of an autoimmune disease such as psoriasis or eczema). Such a pharmaceutical composition may suitably be in the form of a cream, ointment, lotion, gel, foam, transdermal patch, powder, paste or tincture and may suitably include vitamin D3 analogues (e.g calcipotriol and maxacalcitol), steroids (e.g. fluticasone propionate, betamethasone valerate and clobetasol propionate), retinoids (e.g. tazarotene), coal tar and dithranol. Topical medicaments are often used in combination with each other (e.g. a vitamin D3 and a steroid) or with further agents such as salicylic acid. If the pharmaceutical composition of the invention is to be delivered topically for the treatment of psoriasis or eczema, suitably a further substance considered to be effective in treating psoriasis or eczema may be included in the composition such as steroids especially Class 4 or Class 5 steroids such as hydrocortisone (eg 1% hydrocortisone cream); cyclosporin or similar macrolide agent or retinoids.

For all modes of delivery, the polypeptide, pharmaceutical composition or construct of the invention may be formulated in a buffer, in order to stabilise the pH of the composition, at a concentration between 5-50, or more suitably 15-40 or more suitably 25-30 g/litre. Examples of suitable buffer components include physiological salts such as sodium citrate and/or citric acid. Suitably buffers contain 100-200, more suitably 125-175 mM physiological salts such as sodium chloride. Suitably the buffer is selected to have a pKa close to the pH of the composition or the physiological pH of the patient.

Exemplary polypeptide or construct concentrations in a pharmaceutical composition may range from about 1 mg/mL to about 200 mg/ml or from about 50 mg/mL to about 200 mg/mL, or from about 150 mg/mL to about 200 mg/mL.

An aqueous formulation of the polypeptide, construct or pharmaceutical composition of the invention may be prepared in a pH-buffered solution, e.g., at pH ranging from about 4.0 to about 7.0, or from about 5.0 to about 6.0, or alternatively about 5.5. Examples of suitable buffers include phosphate-, histidine-, citrate-, succinate-, acetate-buffers and other organic acid buffers. The buffer concentration can be from about 1 mM to about 100 mM, or from about 5 mM to about 50 mM, depending, for example, on the buffer and the desired tonicity of the formulation.

The tonicity of the pharmaceutical composition may be altered by including a tonicity modifier. Such tonicity modifiers can be charged or uncharged chemical species. Typical uncharged tonicity modifiers include sugars or sugar alcohols or other polyols, preferably trehalose, sucrose, mannitol, glycerol, 1,2-propanediol, raffinose, sorbitol or lactitol (especially trehalose, mannitol, glycerol or 1,2-propanediol). Typical charged tonicity modifiers include salts such as a combination of sodium, potassium or calcium ions, with chloride, sulfate, carbonate, sulfite, nitrate, lactate, succinate, acetate or maleate ions (especially sodium chloride or sodium sulphate); or amino acids such as arginine or histidine. Suitably, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 1 mM to 500 nM. Suitably, at least one isotonic agent is included in the composition.

A surfactant may also be added to the pharmaceutical composition to reduce aggregation of the formulated polypeptide or construct and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, and polysorbate 80. Exemplary concentrations of surfactant may range from about 0.001% to about 10% w/v.

A lyoprotectant may also be added in order to protect the polypeptide or construct of the invention against destabilizing conditions during the lyophilization process. For example, known lyoprotectants include sugars (including glucose, sucrose, mannose and trehalose); polyols (including mannitol, sorbitol and glycerol); and amino acids (including alanine, glycine and glutamic acid). Lyoprotectants can be included in an amount of about 10 mM to 500 mM.

The dosage ranges for administration of the polypeptide of the invention, pharmaceutical composition or construct of the invention are those to produce the desired therapeutic effect. The dosage range required depends on the precise nature of the polypeptide of the invention, pharmaceutical composition or construct, the route of administration, the nature of the formulation, the age of the patient, the nature, extent or severity of the patient's condition, contraindications, if any, and the judgement of the attending physician. Variations in these dosage levels can be adjusted using standard empirical routines for optimisation.

Suitable daily dosages of the polypeptide of the invention, pharmaceutical composition or construct of the invention are in the range of 50 ng-50 mg per kg, such as 50 ug-40 mg per kg, such as 5-30 mg per kg of body weight. The unit dosage can vary from less than 100 mg, but typically will be in the region of 250-2000 mg per dose, which may be administered daily or more frequently, for example 2, 3 or 4 times per day or less frequently for example every other day or once per week, once per fortnight or once per month.

In one aspect of the invention there is provided the use of the polypeptide, pharmaceutical composition or construct of the invention in the manufacture of a medicament for the treatment of autoimmune disease. In a further aspect of the invention there is provided a method of treating autoimmune disease comprising administering to a person in need thereof a therapeutically effective amount of the polypeptide, pharmaceutical composition or construct of the invention.

The word 'treatment' is intended to embrace prophylaxis as well as therapeutic treatment. Treatment of diseases also embraces treatment of exacerbations thereof and also embraces treatment of patients in remission from disease symptoms to prevent relapse of disease symptoms.

Combination Therapy

A pharmaceutical composition of the invention may also comprise one or more active agents (e.g. active agents suitable for treating the diseases mentioned herein). It is within the scope of the invention to use the pharmaceutical composition of the invention in therapeutic methods for the treatment of autoimmune diseases as an adjunct to, or in conjunction with, other established therapies normally used in the treatment of autoimmune diseases.

For the treatment of IBD (such as Crohn's disease or ulcerative colitis), possible combinations include combinations with, for example, one or more active agents selected from the list comprising: 5-aminosalicylic acid, or a prodrug thereof (such as sulfasalazine, olsalazine or bisalazide); corticosteroids (e.g. prednisolone, methylprednisolone, or budesonide); immunosuppressants (e.g. cyclosporin, tacrolimus, methotrexate, azathioprine or 6-mercaptopurine); anti-TNF-alpha antibodies (e.g., infliximab, adalimumab, certolizumab pegol or golimumab); anti-IL12/IL23 antibodies (e.g., ustekinumab); anti-IL6R antibodies or small molecule IL12/1L23 inhibitors (e.g., apilimod); Anti-alpha-4-beta-7 antibodies (e.g., vedolizumab); MAdCAM-1 blockers (e.g., PF-00547659); antibodies against the cell adhesion molecule alpha-4-integrin (e.g., natalizumab); antibodies against the IL2 receptor alpha subunit (e.g., daclizumab or basiliximab); JAK3 inhibitors (e.g., tofacitinib or R348); Syk inhibitors and prodrugs thereof (e.g., fostamatinib and R-406); Phosphodiesterase-4 inhibitors (e.g., tetomilast); HMPL-004; probiotics; Dersalazine; semapimod/CPSI-2364; and protein kinase C inhibitors (e.g. AEB-071). The most suitable combination agents are infliximab, adalimumab, certolizumab pegol or golimumab.

Hence another aspect of the invention provides a pharmaceutical composition of the invention in combination with one or more further active agents, for example one or more active agents described above.

In a further aspect of the invention, the polypeptide, pharmaceutical composition or construct is administered sequentially, simultaneously or separately with at least one active agent selected from the list above.

Similarly, another aspect of the invention provides a combination product comprising:

(A) a polypeptide, pharmaceutical composition or construct of the present invention; and (B) one or more other active agents, wherein each of components (A) and (B) is formulated in admixture with a pharmaceutically-acceptable adjuvant, diluent or carrier. In this aspect of the invention, the combination product may be either a single (combination) formulation or a kit-of-parts. Thus, this aspect of the invention encompasses a combination formulation including a polypeptide, pharmaceutical composition or construct of the present invention and another therapeutic agent, in admixture with a pharmaceutically acceptable adjuvant, diluent or carrier.

The invention also encompasses a kit of parts comprising components:

(i) a polypeptide, pharmaceutical composition or construct of the present invention in admixture with a pharmaceutically acceptable adjuvant, diluent or carrier; and (ii) a formulation including one or more other active agents, in admixture with a pharmaceutically-acceptable adjuvant, diluent or carrier, which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier. The one or more other active agents (i.e. component (B) above) may be, for example, any of the agents mentioned above in connection with the treatment of autoimmune diseases such as IBD (e.g. Crohn's disease and/or ulcerative colitis). If component (B) is more than one further active agent, these further active agents can be formulated with each other or formulated with component (A) or they may be formulated separately. In one embodiment component (B) is one other therapeutic agent. In another embodiment component (B) is two other therapeutic agents. The combination product (either a combined preparation or kit-of-parts) of this aspect of the invention may be used in the treatment or prevention of an autoimmune disease (e.g. the autoimmune diseases mentioned herein).

Suitably the polypeptide, pharmaceutical composition or construct of the invention is for use as a medicament and more suitably for use in the treatment of an autoimmune and/or inflammatory disease.

Autoimmune Diseases and/or Inflammatory Diseases

Autoimmune diseases develop when the immune system responds adversely to normal body tissues. Autoimmune disorders may result in damage to body tissues, abnormal organ growth and/or changes in organ function. The disorder may affect only one organ or tissue type or may affect multiple organs and tissues. Organs and tissues commonly affected by autoimmune disorders include blood components such as red blood cells, blood vessels, connective tissues, endocrine glands such as the thyroid or pancreas, muscles, joints and skin. An inflammatory disease is a disease characterised by inflammation. Many inflammatory diseases are autoimmune diseases and vice-versa.

Autoimmune Diseases and/or Inflammatory Diseases of the GIT

The chronic inflammatory bowel diseases (IBD) Crohn's disease and ulcerative colitis, which afflict both children and adults, are examples of autoimmune and inflammatory diseases of the GIT (Hendrickson et al 2002). Ulcerative colitis is defined as a condition where the inflammatory response and morphologic changes remain confined to the colon. The rectum is involved in 95% of patients. Inflammation is largely limited to the mucosa and consists of continuous involvement of variable severity with ulceration, edema, and hemorrhage along the length of the colon (Hendrickson et al 2002). Ulcerative colitis is usually manifested by the presence of blood and mucus mixed with stool, along with lower abdominal cramping which is most severe during the passage of bowel movements. Clinically, the presence of diarrhoea with blood and mucus differentiates ulcerative colitis from irritable bowel syndrome, in which blood is absent. Unlike ulcerative colitis, the presentation of Crohn's disease is usually subtle, which leads to a later diagnosis. Factors such as the location, extent, and severity of involvement determine the extent of gastrointestinal symptoms. Patients who have ileocolonic involvement usually have postprandial abdominal pain, with tenderness in the right lower quadrant and an occasional inflammatory mass. Symptoms associated with gastroduodenal Crohn's disease include early satiety, nausea, emesis, epigastric pain, or dysphagia. Perianal disease is common, along with anal tags, deep anal fissures, and fistulae (Hendrickson et al 2002). Other diseases of the GIT include for example the inflammatory disease mucositis (suitably drug- and radiation induced-mucositis). In mucositis the lesions can occur anywhere from mouth to anus and for mouth and oesophagus lesions a mouthwash or cream preparation containing the variable domain may be used. For anal and rectal lesions, suppositories, creams or foams containing the variable domain would be suitable for topical application. The immunoglobulin chain variable domains will be cleared from the lamina propria or other inflammatory sites via absorption into the bloodstream at sites of inflammation or via lymphatic clearance and subsequent entry into the bloodstream. The domains will therefore reach the liver via the bloodstream and will be cleared via glomerular filtration in the kidney. There is therefore good rationale that the domains will function therapeutically in diseases such as autoimmune hepatitis, type II diabetes and glomerular nephritis.

Suitably the polypeptide, pharmaceutical composition or construct of the invention is used in the treatment of an autoimmune and/or inflammatory disease of the GI (gastrointestinal) tract where IL-23 contributes to the pathology of such disease.

Suitably the polypeptide, pharmaceutical composition or construct of the invention is for use in the treatment of an autoimmune and/or inflammatory disease of the GI tract selected from the list consisting of Crohn's disease, ulcerative colitis, irritable bowel disease, diabetes type II, glomerulonephritis, autoimmune hepatitis, Sjogren's syndrome, celiac disease and drug- or radiation-induced mucositis (more suitably Crohn's disease or ulcerative colitis, most suitably ulcerative colitis).

Oral delivery of the immunoglobulin chain variable domain will ideally treat inflammatory diseases where IL-23 contributes to at least a proportion of the pathology and the immunoglobulin chain variable domain can access the tissue where the IL-23 is biologically active.

Autoimmune Diseases and/or Inflammatory Diseases of the Skin

Psoriasis is a debilitating autoimmune, dermatological, disease. Plaque psoriasis, the most common form of the disease, is characterized by red skin covered with silvery scales. Histologically the picture is one of disordered differentiation and hyperproliferation of keratinocytes within the psoriatic plaque with inflammatory cell infiltrates (Ortonne, 1999). The psoriatic skin lesions are inflammatory, red, sharply delimited plaques of various shapes with characteristic silvery lustrous scaling. The term psoriasis includes psoriasis and the symptoms of psoriasis including erythema, skin thickening/elevation and scaling.

Biological agents of use in the treatment of psoriasis include anti-TNF-alpha therapies (such as monoclonal antibodies against TNF, e.g. adalimumab and infliximab, or TNF-alpha receptor fusion proteins such as etanercept), humanised antibodies to CD11a (efalizumab) or agents which bind to CD2 such as alefacept (thereby blocking the CD2 LFA3 interaction). It should be noted that not all the biological agents listed here have been approved for use in the treatment of psoriasis.

The polypeptide of the invention may be incorporated into a cream/ointment or other topical carrier for administration to inflammatory skin lesions where IL-23 contributes to the pathology of such lesions.

Suitably the polypeptide, pharmaceutical composition or construct of the invention is for use in the treatment of an autoimmune and/or inflammatory disease of the skin selected from the list consisting of pemphigus, psoriasis, eczema and scleroderma.

Suitably the polypeptide, pharmaceutical composition or construct is for use in the treatment of other autoimmune/inflammatory diseases in which IL-23 is responsible for a proportion of the pathology observed.

Preparative Methods

Polypeptides of the invention can be obtained and manipulated using the techniques disclosed for example in Green and Sambrook 2012 *Molecular Cloning: A Laboratory Manual* 4$^{th}$ Edition Cold Spring Harbour Laboratory Press.

Monoclonal antibodies can be produced using hybridoma technology, by fusing a specific antibody-producing B cell with a myeloma (B cell cancer) cell that is selected for its ability to grow in tissue culture and for an absence of antibody chain synthesis (Köhler and Milstein 1975 and Nelson et al 2000).

A monoclonal antibody directed against a determined antigen can, for example, be obtained by:

a) immortalizing lymphocytes obtained from the peripheral blood of an animal previously immunized with a determined antigen, with an immortal cell and preferably with myeloma cells, in order to form a hybridoma, b) culturing the immortalized cells (hybridoma) formed and recovering the cells producing the antibodies having the desired specificity.

Alternatively, the use of a hybridoma cell is not required. Accordingly, monoclonal antibodies can be obtained by a process comprising the steps of:

a) cloning into vectors, especially into phages and more particularly filamentous bacteriophages, DNA or cDNA sequences obtained from lymphocytes especially peripheral blood lymphocytes of an animal (suitably previously immunized with determined antigens), b) transforming prokaryotic cells with the above vectors in conditions allowing the production of the antibodies, c) selecting the antibodies by subjecting them to antigen-affinity selection, d) recovering the antibodies having the desired specificity.

Methods for immunizing camelids, cloning the VHH repertoire of B cells circulating in blood (Chomezynnski and Sacchi 1987), and isolation of antigen-specific VHHs from immune (Arbabi-Ghahroudi et al 1997) and nonimmune (Tanha et al 2002) libraries using phage, yeast, or ribosome display are known (WO92/01047, Nguyen et al 2001 and Harmsen et al 2007).

Antigen-binding fragments of antibodies such as the scFv and Fv fragments can be isolated and expressed in *E. coli* (Miethe et al 2013, Skerra et al 1988 and Ward et al 1989).

Mutations can be made to the DNA or cDNA that encode polypeptides which are silent as to the amino acid sequence of the polypeptide, but which provide preferred codons for translation in a particular host. The preferred codons for translation of a nucleic acid in, e.g., *E. coli* and *S. cerevisiae*, are known.

Mutation of polypeptides can be achieved for example by substitutions, additions or deletions to a nucleic acid encoding the polypeptide. The substitutions, additions or deletions to a nucleic acid encoding the polypeptide can be introduced by many methods, including for example error-prone PCR, shuffling, oligonucleotide-directed mutagenesis, assembly PCR, PCR mutagenesis, in vivo mutagenesis, cassette mutagenesis, recursive ensemble mutagenesis, exponential ensemble mutagenesis, site-specific mutagenesis (Ling et al 1997), gene reassembly, Gene Site Saturation Mutagenesis (GSSM), synthetic ligation reassembly (SLR) or a combination of these methods. The modifications, additions or deletions to a nucleic acid can also be introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, ensemble mutagenesis, chimeric nucleic acid multimer creation, or a combination thereof.

In particular, artificial gene synthesis may be used (Nambiar et al 1984, Sakamar and Khorana 1988, Wells et al 1985 and Grundstrom et al 1985). A gene encoding a polypeptide of the invention can be synthetically produced by, for example, solid-phase DNA synthesis. Entire genes may be synthesized de novo, without the need for precursor template DNA. To obtain the desired oligonucleotide, the building blocks are sequentially coupled to the growing oligonucleotide chain in the order required by the sequence of the product. Upon the completion of the chain assembly, the product is released from the solid phase to solution, deprotected, and collected. Products can be isolated by high-performance liquid chromatography (HPLC) to obtain the desired oligonucleotides in high purity (Verma and Eckstein 1998)

Expression of immunoglobulin chain variable domains such as VHs and VHHs can be achieved using a suitable expression vector such as a prokaryotic cell such as bacteria, for example *E. coli* (for example according to the protocols disclosed in WO94/04678, which is incorporated herein by reference and detailed further below). Expression of immunoglobulin chain variable domains such as VHs and VHHs can also be achieved using eukaryotic cells, for example insect cells, CHO cells, Vero cells or suitably yeast cells such as yeasts belonging to the genera *Aspergillus, Saccharomyces, Kluyveromyces, Hansenula* or *Pichia*. Suitably *S. cerevisiae* is used (for example according to the protocols disclosed in WO94/025591, which is incorporated herein by reference and detailed further below).

Specifically, VHHs can be prepared according to the methods disclosed in WO94/04678 using *E. coli* cells by a process comprising the steps of:

a) cloning in a Bluescript vector (Agilent Technologies) a DNA or cDNA sequence coding for the VHH (for example obtained from lymphocytes of camelids or produced synthetically) optionally including a His-tag, b) recovering the cloned fragment after amplification using a 5' primer specific for the VHH containing an XhoI site and a 3' primer containing the Spel site having the sequence TC TTA ACT AGT GAG GAG ACG GTG ACC TG (SEQ ID NO: 68), c) cloning the recovered fragment in phase in the Immuno PBS vector (Huse et al 1989) after digestion of the vector with XhoI and Spel restriction enzymes, d) transforming host cells, especially *E. coli* by transfection with the recombinant Immuno PBS vector of step c, e) recovering the expression product of the VHH coding sequence, for instance by affinity purification such as by chromatography on a column using Protein A, cation exchange, or a nickel-affinity resin if the VHH includes a His-tag.

Alternatively, immunoglobulin chain variable domains such as VHs and VHHs are obtainable by a process comprising the steps of:

a) obtaining a DNA or cDNA sequence coding for a VHH, having a determined specific antigen binding site, b) amplifying the obtained DNA or cDNA, using a 5' primer containing an initiation codon and a HindIII site, and a 3' primer containing a termination codon having a XhoI site, c) recombining the amplified DNA or cDNA into the HindIII (position 2650) and XhoI (position 4067) sites of a plasmid pMM984 (Merchlinsky et al 1983), d) transfecting permissive cells especially NB-E cells (Faisst et al 1995) with the recombinant plasmid, e) recovering the obtained products.

Further, immunoglobulin chain variable domains such as VHHs or VHs can be produced using *E. coli* or *S. cerevisiae* according to the methods disclosed in Frenken et al 2000 and WO99/23221 (herein incorporated by reference in their entirety) as follows:

After taking a blood sample from an immunised llama and enriching the lymphocyte population via Ficoll (a neutral, highly branched, high-mass, hydrophilic polysaccharide which dissolves readily in aqueous solutions—Pharmacia) discontinuous gradient centrifugation, isolating total RNA by acid guanidium thiocyanate extraction (Chomezynnski and Sacchi 1987), and first strand cDNA synthesis (e.g. using a cDNA kit such as RPN 1266 (Amersham)), DNA fragments encoding VHH and VH fragments and part of the short or long hinge region are amplified by PCR using the specific primers detailed on pages 22 and 23 of WO99/23221. Upon digestion of the PCR fragments with PstI and HindIII or BstEII, the DNA fragments with a length between about 300 and 450 bp are purified via agarose gel electrophoresis and ligated in the E. coli phagemid vector pUR4536 or the episomal S. cerevisiae expression vector pUR4548, respectively. pUR4536 is derived from pHEN (Hoogenboom et al 1991) and contains the lacI$^q$ gene and unique restriction sites to allow the cloning of the llama VHH and VH genes. pUR4548 is derived from pSY1 (Harmsen et al 1993). From this plasmid, the BstEII site in the leu2 gene is removed via PCR and the cloning sites between the SUC2 signal sequence and the terminator are replaced in order to facilitate the cloning of the VH/VHH gene fragments. The VH/VHHs have the c-myc tag at the C-terminus for detection. Individual E. coli JM109 colonies are transferred to 96 well microtiter plates containing 150 ml 2TY medium supplemented with 1% glucose and 100 mg L$^{-1}$ ampicillin. After overnight growth (37 degrees C.), the plates are duplicated in 2TY medium containing 100 mg L$^{-1}$ ampicillin and 0.1 mM IPTG. After another overnight incubation and optionally freezing and thawing, cells are centrifuged and pelleted and the supernatant can be used in an ELISA. Individual S. cerevisiae colonies are transferred to test tubes containing selective minimal medium (comprising 0.7% yeast nitrogen base, 2% glucose, supplemented with the essential amino acids and bases) and are grown for 48 h at 30 degrees C. Subsequently, the cultures are diluted ten times in YPGaI medium (comprising 1% yeast extract, 2% bacto peptone and 5% galactose). After 24 and 48 h of growth, the cells are pelleted and the culture supernatant can be analysed in an ELISA. Absorbance at 600 nm (OD600) is optionally measured.

Further, immunoglobulin chain variable domains such as VH/VHHs can be produced using S. cerevisiae using the procedure as follows:

Isolate a naturally-occurring DNA sequence encoding the VH/VHH or obtain a synthetically produced DNA sequence encoding the VH/VHH, including a 5'-UTR, signal sequence, stop codons and flanked with SacI and HindIII sites (such a synthetic sequence can be produced as outlined above or for example may be ordered from a commercial supplier such as Geneart (Life Technologies)).

Use the restriction sites for transfer of the VH/VHH gene to the multi-copy integration (MCI) vector pUR8569 or pUR8542, as follows. Cut the DNA sequence encoding the VHH optionally contained within a shuttle vector, cassette or other synthetic gene construct and the MCI vector with SacI and HindIII using: 25 ul VHH DNA (Geneart plasmid or MCI vector), 1 ul SacI, 1 ul HindIII, 3 ul of a suitable buffer for double digestion such as NEB buffer 1 (New England Biolabs) overnight at 37 degrees C. Run 25 ul of digested DNA encoding the VHH and 25 ul of digested MCI vector on a 1.5% agarose gel with 1×TAE buffer and then perform gel extraction for example using QIAquick Gel Extraction Kit (Qiagen)). Set-up a ligation of digested MCI vector and digested DNA encoding the VH/VHH as follows: 100 ng vector, 30 ng VHH gene, 1.5 ul 10× ligase buffer, 1 ul T4 DNA ligase, and ddH$_2$O. Then perform ligation overnight at 16 degrees C.

Next transform the E. coli cells. For chemical competent XL-1 blue cells, thaw 200 ul heat competent XL-1 blue cells and add 5 ul ligation mix on ice for about 30 minutes followed by heat shock for 90 seconds at 42 degrees C. Then add 800 ul Luria-Bertani low salt medium supplemented with 2% glucose and recover cells for 2 hours at 37 degrees C. Plate cells on Luria-Bertani agar and ampicillin (100 ug/ml) plates and keep overnight at 37 degrees C. For electro competent TG1 E. coli cells, use an electroporation cuvette. In the electroporation cuvette: thaw 50 ul electro competent TG1 cells and 1 ul ligation mix on ice for about 15 minutes. Place the cuvette in the holder and pulse. Add 500 ul of 2TY medium and recover cells for 30 minutes at 37 degrees C. Plate 100 ul of cells on Luria-Bertani, agar, containing ampicillin (100 ug/ml) and 2% glucose plates. Keep plates at 37 degrees C. overnight.

After cloning of the VH/VHH gene into E. coli as detailed above, S. cerevisiae can be transformed with the linearized MCI vector. Before transformation is carried out, some steps are performed: (i) the DNA should be changed from circular to linear by digestion or else the DNA cannot be integrated into the yeast genome and (ii) the digested DNA should be cleaned of impurities by ethanol precipitation. Also, during the transformation process, the yeast cells are made semi-permeable so the DNA can pass the membrane.

Preparation for yeast transformation: perform a HpaI digestion of the midi-prep prepared from the selected E. coli colony expressing the VH/VHH gene as follows. Prepare a 100 ul solution containing 20 ng of midi-prep, 5 ul HpaI, 10 ul of appropriate buffer such as NEB4 buffer (BioLabs), and ddH$_2$O.

Cut the DNA with the HpaI at room temperature overnight. Next perform an ethanol precipitation (and put to one side a 5 ul sample from HpaI digestion). Add 300 ul ethanol 100% to 95 ul HpaI digested midiprep, vortex, and spin at full speed for 5 minutes. Carefully decant when a pellet is present, add 100 ul of ethanol 70%, then spin again for 5 minutes at full speed. Decant the sample again, and keep at 50-60 degrees C. until the pellet is dry. Re-suspend the pellet in 50 ul ddH$_2$O. Run 5 ul on a gel beside the 5 ul HpaI digested sample.

Yeast transformation: prepare YNBglu plates. Use 10 g agar+425 ml water (sterilised), 25 ml filtered 20×YNB (3.35 g YNB (yeast nitrogen base) in 25 ml sterilized H$_2$O) and 50 ml sterile 20% glucose and pour into petri dishes. Pick one yeast colony from the masterplate and grow in 3 ml YPD (Yeast Extract Peptone Dextrose) overnight at 30 degrees C. Next day prepare about 600 ml YPD and use to fill 3 flasks with 275 ml, 225 ml and 100 ml YPD. Add 27.5 ul yeast YPD culture to the first flask and mix gently. Take 75 ml from the first flask and put this in the second flask, mix gently. Take 100 ml from the second flask and put in the third one, mix gently. Grow until reaching an OD660 of between 1 and 2. Divide the flask reaching this OD over 4 Falcon tubes, ±45 ml in each. Spin for 2 minutes at 4200 rpm. Discard the supernatant. Dissolve the pellets in two Falcon tubes with 45 ml H$_2$O (reducing the number of tubes from 4 to 2). Spin for 2 minutes at 4200 rpm. Dissolve the pellets in 45 ml H$_2$O (from 2 tubes to 1). Spin for 2 minutes at 4200 rpm. Gently dissolve the pellets in 5 ml lithium acetate (LiAc) (100 mM), and spin for a few seconds. Carefully discard some LiAc, but retain over half of the LiAc in the tube. Vortex the cells, boil carrier DNA for 5 minutes and quickly chill in ice-water. Add to a 15 ml tube containing:

240 ul PEG, 50 ul cells, 36 uLiAc (1M), 25 ul carrier DNA, 45 ul ethanol precipitated VH/VHH. Mix gently after each step (treat the blank sample the same, only without ethanol precipitated VH/VHH). Incubate for 30 minutes at 30 degrees C., gently invert the tube 3-4 times, then heat shock for 20-25 minutes at 42 degrees C. Spin up to 6000 rpm for a brief time. Gently remove the supernatant and add 250 ul ddH$_2$O and mix. Streak all of it on an YNBglu plate until plates are dry and grow for 4-5 days at 30 degrees C. Finally, prepare YNBglu plates by dividing plates in 6 equal parts, number the parts 1 to 6, inoculate the biggest colony and streak out number 1. Repeat for other colonies from big to small from 1 to 6. Grow at 30 degrees C. for 3-4 days large until colonies are produced. The VH/VHH clones are grown using glucose as a carbon source, and induction of VH/VHH expression is done by turning on the Galactose-7-promoter by adding 0.5% galactose. Perform a 3 mL small scale culture to test the colonies and choose which one shows the best expression of the VH or VHH. This colony is then used in purification.

Purification: the VH/VHH is purified by cation exchange chromatography with a strong anion resin (such as Capto S). On day 1, inoculate the selected yeast colony expressing the VH/VHH in 5 ml YPD medium (YP medium+2% glucose) and grow the cells in 25 mL sealed sterile tubes at 30 degrees C. overnight (shaking at 180 rpm). On day 2, dilute the 5 ml overnight culture in 50 mL freshly prepared YP medium+2% glucose+0.5% galactose, grow the cells in 250 ml aerated baffled flasks at 30 degrees C. for two nights (shaking at 180 rpm). On day 4, spin the cells down in a centrifuge at 4200 rpm for 20 min. Cation exchange purification step using a strong anion resin: adjust the pH of the supernatant containing the ligand to 3.5. Wash 0.75 ml resin (+/−0.5 mL slurry) per of 50 mL supernatant with 50 mL of ddH$_2$O followed by three washes with binding buffer. Add the washed resin to the supernatant and incubate the suspension at 4 degrees C. on a shaker for 1.5 hours. Pellet the resin-bound VH/VHH by centrifugation at 500 g for 2 minutes and wash it with wash buffer. Decant supernatant and re-suspend the resin with 10 mL of binding buffer. Put a filter in a PD-10 column, pour the resin in the column and let the resin settle for a while, then add a filter above the resin. Wait until all binding buffer has run through. Elute the VH/VHH with 6×0.5 ml elution buffer. Collect the elution fractions in eppendorf tubes. Measure the protein concentration of the 6 eluted fractions with a Nanodrop. Pool the fractions that contain the VHH and transfer the solution into a 3,500 Da cutoff dialysis membrane. Dialyze the purified protein solution against 3 L of PBS overnight at 4 degrees C. On day 5, dialyze the purified protein solution against 2 L of fresh PBS for an additional 2 hours at 4 degrees C. Finally, calculate the final concentration by BCA.

Although discussed in the context of the VH/VHH, the techniques described above could also be used for scFv, Fab, Fv and other antibody fragments if required.

Multiple antigen-binding fragments (suitably VH/VHHs) can be fused by chemical cross-linking by reacting amino acid residues with an organic derivatising agent such as described by Blattler et al 1985. Alternatively, the antigen-binding fragments may be fused genetically at the DNA level i.e. a polynucleotide construct formed which encodes the complete polypeptide construct comprising one or more antigen-binding fragments. One way of joining multiple antigen-binding fragments via the genetic route is by linking the antigen-binding fragment coding sequences either directly or via a peptide linker. For example, the carboxy-terminal end of the first antigen-binding fragment may be linked to the amino-terminal end of the next antigen-binding fragment. This linking mode can be extended in order to link antigen-binding fragments for the construction of tri-, tetra-, etc. functional constructs. A method for producing multivalent (such as bivalent) VHH polypeptide constructs is disclosed in WO 96/34103 (herein incorporated by reference in its entirety).

Suitably, the polypeptide of the invention (in particular, a VHH of the invention) can be produced in a fungus such as a yeast (for example, S. cerevisiae) comprising growth of the fungus on a medium comprising a carbon source wherein 50-100 wt % of said carbon source is ethanol, according to the methods disclosed in WO02/48382. Large scale production of VHH fragments in S. cerevisiae is described in Thomassen et al 2002.

In one aspect of the invention there is provided a process for the preparation of the polypeptide or construct of the invention comprising the following steps:

i) cloning into a vector, such as a plasmid, the polynucleotide of the invention, ii) transforming a cell, such as a bacterial cell or a yeast cell capable of producing the polypeptide or construct of the invention, with said vector in conditions allowing the production of the polypeptide or construct, iii) recovering the polypeptide or construct, such as by affinity chromatography.

Clauses Setting Out Further Embodiments of the Invention are as Follows:

1. A polypeptide comprising an immunoglobulin chain variable domain which binds to IL-23, wherein the immunoglobulin chain variable domain comprises three complementarity determining regions (CDR1-CDR3) and four framework regions (FR1-FR4), wherein CDR1 comprises a sequence sharing 60% or greater sequence identity with SEQ ID NO: 1, CDR2 comprises a sequence sharing 50% or greater sequence identity with SEQ ID NO: 2 and CDR3 comprises a sequence sharing 50% or greater sequence identity with SEQ ID NO: 3.

2. The polypeptide according to clause 1, wherein CDR3 comprises a sequence sharing 80% or greater sequence identity with SEQ ID NO: 3.

3. The polypeptide according to clause 2, wherein CDR3 consists of a sequence sharing 80% or greater sequence identity with SEQ ID NO: 3.

4. The polypeptide according to either clause 2 or 3, wherein any residues of CDR3 differing from their corresponding residues in SEQ ID NO: 3 are conservative substitutions with respect to their corresponding residues.

5. The polypeptide according to either clause 2 or 3, wherein the residue of CDR3 corresponding to residue number 6 of SEQ ID NO: 3 is I.

6. The polypeptide according to either clause 2 or 3, wherein the residue of CDR3 corresponding to residue number 6 of SEQ ID NO: 3 is L.

7. The polypeptide according to clause 4, wherein the residue of CDR3 corresponding to residue number 6 of SEQ ID NO: 3 is I or L and any other residues of CDR3 differing from their corresponding residues in SEQ ID NO: 3 are conservative substitutions with respect to their corresponding residues.

8. The polypeptide according to clause 2, wherein CDR3 comprises SEQ ID NO: 3.

9. The polypeptide according to clause 3, wherein CDR3 consists of SEQ ID NO: 3.

10. The polypeptide according to any one of clauses 1 to 9, wherein CDR1 comprises a sequence sharing 80% or greater sequence identity with SEQ ID NO: 1.

11. The polypeptide according to clause 10, wherein CDR1 consists of a sequence sharing 80% or greater sequence identity with SEQ ID NO: 1.
12. The polypeptide according to any one of clauses 1 to 9, wherein any residues of CDR1 differing from their corresponding residues in SEQ ID NO: 1 are conservative substitutions with respect to their corresponding residues.
13. The polypeptide according to clause 11, wherein CDR1 comprises SEQ ID NO: 1.
14. The polypeptide according to clause 13, wherein CDR1 consists of SEQ ID NO: 1.
15. The polypeptide according to any one of clauses 1 to 14, wherein CDR2 comprises a sequence sharing 55% or greater sequence identity, such as sharing 60% or greater sequence identity, such as sharing 70% or greater sequence identity, such as sharing 75% or greater sequence identity, such as sharing 80% or greater sequence identity, such as sharing 85% or greater sequence identity, such as sharing 90% or greater sequence identity, with SEQ ID NO: 2.
16. The polypeptide according to clause 15, wherein CDR2 consists of a sequence sharing 55% or greater sequence identity, such as sharing 60% or greater sequence identity, such as sharing 70% or greater sequence identity, such as sharing 75% or greater sequence identity, such as sharing 80% or greater sequence identity, such as sharing 85% or greater sequence identity, such as sharing 90% or greater sequence identity, with SEQ ID NO: 2.
17. The polypeptide according to any one of clauses 1 to 16, wherein the residue of CDR2 corresponding to residue number 9 of SEQ ID NO: 2 is D or H and/or the residue of CDR2 corresponding to residue number 10 of SEQ ID NO: 2 is Y or D and/or the residue of CDR2 corresponding to residue number 11 of SEQ ID NO: 2 is S, G, R or A (such as S, R or A, such as S or A) and/or the residue of CDR2 corresponding to residue number 14 of SEQ ID NO: 2 is V or A.
18. The polypeptide according to any one of clauses 1 to 17, wherein any residues of CDR2 differing from their corresponding residues in SEQ ID NO: 2 are conservative substitutions with respect to their corresponding residues.
19. The polypeptide according to clause 15, wherein CDR2 comprises SEQ ID NO: 2.
20. The polypeptide according to clause 19, wherein CDR2 consists of SEQ ID NO: 2.
21. The polypeptide according to any one of clauses 1 to 20, wherein FR1 comprises a sequence sharing 5% or greater sequence identity, such as sharing 12% or greater sequence identity, such as sharing 18% or greater sequence identity, such as sharing 26% or greater sequence identity, such as sharing 32% or greater sequence identity, such as sharing 38% or greater sequence identity, such as sharing 46% or greater sequence identity, such as sharing 52% or greater sequence identity, such as sharing 58% or greater sequence identity, such as sharing 62% or greater sequence identity, such as sharing 66% or greater sequence identity, such as sharing 68% or greater sequence identity, such as sharing 72% or greater sequence identity, such as sharing 75% or greater sequence identity, such as sharing 78% or greater sequence identity, such as sharing 82% or greater sequence identity, such as sharing 85% or greater sequence identity, such as sharing 90% or greater sequence identity, such as sharing 95% or greater sequence identity, with SEQ ID NO: 4.
22. The polypeptide according to clause 21, wherein FR1 consists of a sequence sharing 5% or greater sequence identity, such as sharing 12% or greater sequence identity, such as sharing 18% or greater sequence identity, such as sharing 26% or greater sequence identity, such as sharing 32% or greater sequence identity, such as sharing 38% or greater sequence identity, such as sharing 46% or greater sequence identity, such as sharing 52% or greater sequence identity, such as sharing 58% or greater sequence identity, such as sharing 62% or greater sequence identity, such as sharing 66% or greater sequence identity, such as sharing 68% or greater sequence identity, such as sharing 72% or greater sequence identity, such as sharing 75% or greater sequence identity, such as sharing 78% or greater sequence identity, such as sharing 82% or greater sequence identity, such as sharing 85% or greater sequence identity, such as sharing 90% or greater sequence identity, such as sharing 95% or greater sequence identity, with SEQ ID NO: 4.
23. The polypeptide according to any one of clauses 1 to 22, wherein the residue of FR1 corresponding to residue number 1 of SEQ ID NO: 4 is D or E.
24. The polypeptide according to clause 23, wherein the residue of FR1 corresponding to residue number 1 of SEQ ID NO: 4 is D.
25. The polypeptide according to clause 24, wherein the residues of FR1 corresponding to residue numbers 1 to 5 of SEQ ID NO: 4 are DVQLV.
26. The polypeptide according to any one of clauses 1 to 25, wherein any residues of FR1 differing from their corresponding residues in SEQ ID NO: 4 are conservative substitutions with respect to their corresponding residues.
27. The polypeptide according to clause 21, wherein FR1 comprises SEQ ID NO: 4.
28. The polypeptide according to clause 27, wherein FR1 consists of SEQ ID NO: 4.
29. The polypeptide according to any one of clauses 1 to 28, wherein FR2 comprises a sequence sharing 10% or greater sequence identity, such as sharing 15% or greater sequence identity, such as sharing 25% or greater sequence identity, such as sharing 30% or greater sequence identity, such as sharing 40% or greater sequence identity, such as sharing 45% or greater sequence identity, such as sharing 55% or greater sequence identity, such as sharing 60% or greater sequence identity, such as sharing 70% or greater sequence identity, such as sharing 75% or greater sequence identity, such as sharing 85% or greater sequence identity, such as sharing 90% or greater sequence identity, with SEQ ID NO: 5.
30. The polypeptide according to clause 29, wherein FR2 consists of a sequence sharing 10% or greater sequence identity, such as sharing 15% or greater sequence identity, such as sharing 25% or greater sequence identity, such as sharing 30% or greater sequence identity, such as sharing 40% or greater sequence identity, such as sharing 45% or greater sequence identity, such as sharing 55% or greater sequence identity, such as sharing 60% or greater sequence identity, such as sharing 70% or greater sequence identity, such as sharing 75% or greater sequence identity, such as sharing 85% or greater sequence identity, such as sharing 90% or greater sequence identity, with SEQ ID NO: 5.
31. The polypeptide according to any one of clauses 1 to 30, wherein any residues of FR2 differing from their corresponding residues in SEQ ID NO: 5 are conservative substitutions with respect to their corresponding residues.
32. The polypeptide according to clause 29, wherein FR2 comprises SEQ ID NO: 5.
33. The polypeptide according to clause 32, wherein FR2 consists of SEQ ID NO: 5.
34. The polypeptide according to any one of clauses 1 to 33, wherein FR3 comprises a sequence sharing 8% or greater sequence identity, such as sharing 15% or greater sequence identity, such as sharing 20% or greater sequence identity, such as sharing 26% or greater sequence identity, such as sharing 32% or greater sequence identity, such as sharing 40% or greater sequence identity, such as sharing 45% or greater sequence identity, such as sharing 52% or greater sequence identity, such as sharing 58% or greater sequence identity, such as sharing 65% or greater sequence identity, such as sharing 70% or greater sequence identity, such as sharing 76% or greater sequence identity, such as sharing 80% or greater sequence identity, such as sharing 82% or greater sequence identity, such as sharing 85% or greater sequence identity, such as sharing 90% or greater sequence identity, such as sharing 92% or greater sequence identity, such as sharing 95% or greater sequence identity, with SEQ ID NO: 6.
35. The polypeptide according to clause 34, wherein FR3 consists of a sequence sharing 8% or greater sequence identity, such as sharing 15% or greater sequence identity, such as sharing 20% or greater sequence identity, such as sharing 26% or greater sequence identity, such as sharing 32% or greater sequence identity, such as sharing 40% or greater sequence identity, such as sharing 45% or greater sequence identity, such as sharing 52% or greater sequence identity, such as sharing 58% or greater sequence identity, such as sharing 65% or greater sequence identity, such as sharing 70% or greater sequence identity, such as sharing 76% or greater sequence identity, such as sharing 80% or greater sequence identity, such as sharing 82% or greater sequence identity, such as sharing 85% or greater sequence identity, such as sharing 90% or greater sequence identity, such as sharing 92% or greater sequence identity, such as sharing 95% or greater sequence identity, with SEQ ID NO: 6.
36. The polypeptide according to any one of clauses 1 to 35, wherein any residues of FR3 differing from their corresponding residues in SEQ ID NO: 6 are conservative substitutions with respect to their corresponding residues.
37. The polypeptide according to clause 34, wherein FR3 comprises SEQ ID NO: 6.
38. The polypeptide according to clause 37, wherein FR3 consists of SEQ ID NO: 6.
39. The polypeptide according to any one of clauses 1 to 38, wherein FR4 comprises a sequence sharing 5% or greater sequence identity, such as sharing 10% or greater sequence identity, such as sharing 20% or greater sequence identity, such as sharing 30% or greater sequence identity, such as sharing 40% or greater sequence identity, such as sharing 50% or greater sequence identity, such as sharing 60% or greater sequence identity, such as sharing 70% or greater sequence identity, such as sharing 80% or greater sequence identity, such as sharing 90% or greater sequence identity, with SEQ ID NO: 7.
40. The polypeptide according to clause 39, wherein FR4 consists of a sequence sharing 5% or greater sequence identity, such as sharing 10% or greater sequence identity, such as sharing 20% or greater sequence identity, such as sharing 30% or greater sequence identity, such as sharing 40% or greater sequence identity, such as sharing 50% or greater sequence identity, such as sharing 60% or greater sequence identity, such as sharing 70% or greater sequence identity, such as sharing 80% or greater sequence identity, such as sharing 90% or greater sequence identity, with SEQ ID NO: 7.
41. The polypeptide according to any one of clauses 1 to 40, wherein any residues of FR4 differing from their corresponding residues in SEQ ID NO: 7 are conservative substitutions with respect to their corresponding residues.
42. The polypeptide according to clause 39, wherein FR4 comprises SEQ ID NO: 7.
43. The polypeptide according to clause 42 wherein FR4 consists of SEQ ID NO: 7.
44. The polypeptide according to any one of clauses 1 to 43 which comprises a sequence sharing 50% or greater sequence identity, such as sharing 55% or greater sequence identity, such as sharing 60% or greater sequence identity, such as sharing 65% or greater sequence identity, such as sharing 70% or greater sequence identity, such as sharing 75% or greater sequence identity, such as sharing 80% or greater sequence identity, such as sharing 85% or greater sequence identity, such as sharing 90% or greater sequence identity, such as sharing 95% or greater sequence identity, such as sharing 96% or greater sequence identity, such as sharing 97% or greater sequence identity, such as sharing 98% or greater sequence identity, such as sharing 99% or greater sequence identity, with SEQ ID NO: 8.
45. The polypeptide according to clause 44 which consists of a sequence sharing 50% or greater sequence identity, such as sharing 55% or greater sequence identity, such as sharing 60% or greater sequence identity, such as sharing 65% or greater sequence identity, such as sharing 70% or greater sequence identity, such as sharing 75% or greater sequence identity, such as sharing 80% or greater sequence identity, such as sharing 85% or greater sequence identity, such as sharing 90% or greater sequence identity, such as sharing 95% or greater sequence identity, such as sharing 96% or greater sequence identity, such as sharing 97% or greater sequence identity, such as sharing 98% or greater sequence identity, such as sharing 99% or greater sequence identity, with SEQ ID NO: 8.
46. The polypeptide according to any one of clauses 1 to 45, wherein the N-terminus of the polypeptide is D.
47. The polypeptide according to clause 44 which comprises SEQ ID NO: 8.
48. The polypeptide according to clause 47 which consists of SEQ ID NO: 8.
49. A polypeptide comprising an immunoglobulin chain variable domain which binds to IL-23, wherein the immunoglobulin chain variable domain comprises three complementarity determining regions (CDR1-CDR3) and four framework regions (FR1-FR4), wherein:
  (a) CDR1 consists of a sequence sharing 60% or greater sequence identity with SEQ ID NO: 1, CDR2 consists of a sequence sharing 70% or greater sequence identity with SEQ ID NO: 2 and CDR3 consists of a sequence sharing 70% or greater sequence identity with SEQ ID NO: 3;
  (b) FR1 consists of a sequence sharing 70% or greater sequence identity with SEQ ID NO: 4, FR2 consists of a sequence sharing 70% or greater sequence identity with SEQ ID NO: 5, FR3 consists of a sequence sharing 70% or greater sequence identity with SEQ ID NO: 6 and FR4 consists of a sequence sharing 70% or greater sequence identity with SEQ ID NO: 7; and (c) the polypeptide consists of a sequence sharing 70% or greater sequence identity with SEQ ID NO: 8.

50. A polypeptide comprising an immunoglobulin chain variable domain which binds to IL-23, wherein the immunoglobulin chain variable domain comprises three complementarity determining regions (CDR1-CDR3) and four framework regions (FR1-FR4), wherein CDR1 comprises a sequence sharing 60% or greater sequence identity with SEQ ID NO: 14 CDR2 comprises a sequence sharing 50% or greater sequence identity with SEQ ID NO: 15 and CDR3 comprises a sequence sharing 50% or greater sequence identity with SEQ ID NO: 16.

51. The polypeptide according to clause 50, wherein CDR3 comprises a sequence sharing 60% or greater sequence identity, such as 80% or greater sequence identity, with SEQ 52. The polypeptide according to clause 51, wherein CDR3 consists of a sequence sharing 60% or greater sequence identity, such as 80% or greater sequence identity, with SEQ ID NO: 16.

53. The polypeptide according to any one of clauses 50 to 52, wherein any residues of CDR3 differing from their corresponding residues in SEQ ID NO: 16 are conservative substitutions with respect to their corresponding residues.

54. The polypeptide according to clause 51, wherein CDR3 comprises SEQ ID NO: 16.

55. The polypeptide according to clause 54, wherein CDR3 consists of SEQ ID NO: 16.

56. The polypeptide according to any one of clauses 50 to 55, wherein CDR1 comprises a sequence sharing 80% or greater sequence identity with SEQ ID NO: 14.

57. The polypeptide according to clause 56, wherein CDR1 consists of a sequence sharing 80% or greater sequence identity with SEQ ID NO: 14.

58. The polypeptide according to any one of clauses 50 to 57, wherein any residues of CDR1 differing from their corresponding residues in SEQ ID NO: 14 are conservative substitutions with respect to their corresponding residues.

59. The polypeptide according to clause 56, wherein CDR1 comprises SEQ ID NO: 14.

60. The polypeptide according to clause 59, wherein CDR1 consists of SEQ ID NO: 14.

61. The polypeptide according to any one of clauses 50 to 60, wherein CDR2 comprises a sequence sharing 55% or greater sequence identity, such as sharing 60% or greater sequence identity, such as sharing 70% or greater sequence identity, such as sharing 75% or greater sequence identity, such as sharing 80% or greater sequence identity, such as sharing 85% or greater sequence identity, such as sharing 90% or greater sequence identity, with SEQ ID NO: 15.

62. The polypeptide according to clause 61, wherein CDR2 consists of a sequence sharing 60% or greater sequence identity, such as sharing 70% or greater sequence identity, such as sharing 75% or greater sequence identity, such as sharing 80% or greater sequence identity, such as sharing 85% or greater sequence identity, such as sharing 90% or greater sequence identity, with SEQ ID NO: 15.

63. The polypeptide according to any one of clauses 50 to 62, wherein any residues of CDR2 differing from their corresponding residues in SEQ ID NO: 15 are conservative substitutions with respect to their corresponding residues.

64. The polypeptide according to clause 61, wherein CDR2 comprises SEQ ID NO: 15.

65. The polypeptide according to clause 64, wherein CDR2 consists of SEQ ID NO: 15.

66. The polypeptide according to any one of clauses 50 to 65, wherein:

(a) FR1 comprises a sequence sharing 5% or greater sequence identity, such as sharing 12% or greater sequence identity, such as sharing 18% or greater sequence identity, such as sharing 26% or greater sequence identity, such as sharing 32% or greater sequence identity, such as sharing 38% or greater sequence identity, such as sharing 46% or greater sequence identity, such as sharing 52% or greater sequence identity, such as sharing 58% or greater sequence identity, such as sharing 62% or greater sequence identity, such as sharing 66% or greater sequence identity, such as sharing 68% or greater sequence identity, such as sharing 72% or greater sequence identity, such as sharing 75% or greater sequence identity, such as sharing 78% or greater sequence identity, such as sharing 82% or greater sequence identity, such as sharing 85% or greater sequence identity, such as sharing 90% or greater sequence identity, such as sharing 95% or greater sequence identity, with SEQ ID NO: 17;

(b) FR2 comprises a sequence sharing 10% or greater sequence identity, such as sharing 15% or greater sequence identity, such as sharing 25% or greater sequence identity, such as sharing 30% or greater sequence identity, such as sharing 40% or greater sequence identity, such as sharing 45% or greater sequence identity, such as sharing 55% or greater sequence identity, such as sharing 60% or greater sequence identity, such as sharing 70% or greater sequence identity, such as sharing 75% or greater sequence identity, such as sharing 85% or greater sequence identity, such as sharing 90% or greater sequence identity, with SEQ ID NO: 18;

(c) FR3 comprises a sequence sharing 8% or greater sequence identity, such as sharing 15% or greater sequence identity, such as sharing 20% or greater sequence identity, such as sharing 26% or greater sequence identity, such as sharing 32% or greater sequence identity, such as sharing 40% or greater sequence identity, such as sharing 45% or greater sequence identity, such as sharing 52% or greater sequence identity, such as sharing 58% or greater sequence identity, such as sharing 65% or greater sequence identity, such as sharing 70% or greater sequence identity, such as sharing 76% or greater sequence identity, such as sharing 80% or greater sequence identity, such as sharing 82% or greater sequence identity, such as sharing 85% or greater sequence identity, such as sharing 90% or greater sequence identity, such as sharing 92% or greater sequence identity, such as sharing 95% or greater sequence identity, with SEQ ID NO: 19; and/or (d) FR4 comprises a sequence sharing 5% or greater sequence identity, such as sharing 10% or greater sequence identity, such as sharing 20% or greater sequence identity, such as sharing 30% or greater sequence identity, such as sharing 40% or greater sequence identity, such as sharing 50% or greater sequence identity, such as sharing 60% or greater sequence identity, such as sharing 70% or greater sequence identity, such as sharing 80% or greater sequence identity, such as sharing 90% or greater sequence identity, with SEQ ID NO: 20.
67. The polypeptide according to clause 66, wherein FR1 comprises SEQ ID NO: 17 and/or FR2 comprises SEQ ID NO: 18 and/or FR3 comprises SEQ ID NO: 19 and/or FR4 comprises SEQ ID NO: 20.
68. The polypeptide according to any one of clauses 50 to 67 which comprises a sequence sharing 50% or greater sequence identity, such as sharing 55% or greater sequence identity, such as sharing 60% or greater sequence identity, such as sharing 65% or greater sequence identity, such as sharing 70% or greater sequence identity, such as sharing 75% or greater sequence identity, such as sharing 80% or greater sequence identity, such as sharing 85% or greater sequence identity, such as sharing 90% or greater sequence identity, such as sharing 95% or greater sequence identity, such as sharing 96% or greater sequence identity, such as sharing 97% or greater sequence identity, such as sharing 98% or greater sequence identity, such as sharing 99% or greater sequence identity, with SEQ ID NO: 13.
69. The polypeptide according to clause 68 which comprises or consists of SEQ ID NO: 13.
70. A polypeptide comprising an immunoglobulin chain variable domain which binds to IL-23, wherein the immunoglobulin chain variable domain comprises three complementarity determining regions (CDR1-CDR3) and four framework regions (FR1-FR4), wherein CDR1 comprises a sequence sharing 60% or greater sequence identity with SEQ ID NO: 22 CDR2 comprises a sequence sharing 50% or greater sequence identity with SEQ ID NO: 23 and CDR3 comprises a sequence sharing 50% or greater sequence identity with SEQ ID NO: 24.
71. The polypeptide according to clause 70, wherein CDR3 comprises a sequence sharing 60% or greater sequence identity, such as 80% or greater sequence identity, with SEQ ID NO: 24.
72. The polypeptide according to clause 71, wherein CDR3 consists of a sequence sharing 60% or greater sequence identity, such as 80% or greater sequence identity, with SEQ ID NO: 24.
73. The polypeptide according to any one of clauses 70 to 72, wherein any residues of CDR3 differing from their corresponding residues in SEQ ID NO: 24 are conservative substitutions with respect to their corresponding residues.
74. The polypeptide according to clause 71, wherein CDR3 comprises SEQ ID NO: 24.
75. The polypeptide according to clause 74, wherein CDR3 consists of SEQ ID NO: 24.
76. The polypeptide according to any one of clauses 70 to 75, wherein CDR1 comprises a sequence sharing 80% or greater sequence identity with SEQ ID NO: 22.
77. The polypeptide according to clause 76, wherein CDR1 consists of a sequence sharing 80% or greater sequence identity with SEQ ID NO: 22.
78. The polypeptide according to any one of clauses 70 to 77, wherein any residues of CDR1 differing from their corresponding residues in SEQ ID NO: 22 are conservative substitutions with respect to their corresponding residues.
79. The polypeptide according to clause 76, wherein CDR1 comprises SEQ ID NO: 22.
80. The polypeptide according to clause 79, wherein CDR1 consists of SEQ ID NO: 22.
81. The polypeptide according to any one of clauses 70 to 80, wherein CDR2 comprises a sequence sharing 55% or greater sequence identity, such as sharing 60% or greater sequence identity, such as sharing 70% or greater sequence identity, such as sharing 75% or greater sequence identity, such as sharing 80% or greater sequence identity, such as sharing 85% or greater sequence identity, such as sharing 90% or greater sequence identity, with SEQ ID NO: 23.
82. The polypeptide according to clause 81, wherein CDR2 consists of a sequence sharing 60% or greater sequence identity, such as sharing 70% or greater sequence identity, such as sharing 75% or greater sequence identity, such as sharing 80% or greater sequence identity, such as sharing 85% or greater sequence identity, such as sharing 90% or greater sequence identity, with SEQ ID NO: 23.
83. The polypeptide according to any one of clauses 70 to 82, wherein any residues of CDR2 differing from their corresponding residues in SEQ ID NO: 23 are conservative substitutions with respect to their corresponding residues.
84. The polypeptide according to clause 81, wherein CDR2 comprises SEQ ID NO: 23.
85. The polypeptide according to clause 84, wherein CDR2 consists of SEQ ID NO: 23.
86. The polypeptide according to any one of clauses 70 to 85, wherein:
(a) FR1 comprises a sequence sharing 5% or greater sequence identity, such as sharing 12% or greater sequence identity, such as sharing 18% or greater sequence identity, such as sharing 26% or greater sequence identity, such as sharing 32% or greater sequence identity, such as sharing 38% or greater sequence identity, such as sharing 46% or greater sequence identity, such as sharing 52% or greater sequence identity, such as sharing 58% or greater sequence identity, such as sharing 62% or greater sequence identity, such as sharing 66% or greater sequence identity, such as sharing 68% or greater sequence identity, such as sharing 72% or greater sequence identity, such as sharing 75% or greater sequence identity, such as sharing 78% or greater sequence identity, such as sharing 82% or greater sequence identity, such as sharing 85% or greater sequence identity, such as sharing 90% or greater sequence identity, such as sharing 95% or greater sequence identity, with SEQ ID NO: 25;
(b) FR2 comprises a sequence sharing 10% or greater sequence identity, such as sharing 15% or greater sequence identity, such as sharing 25% or greater sequence identity, such as sharing 30% or greater sequence identity, such as sharing 40% or greater sequence identity, such as sharing 45% or greater sequence identity, such as sharing 55% or greater sequence identity, such as sharing 60% or greater sequence identity, such as sharing 70% or greater sequence identity, such as sharing 75% or greater sequence identity, such as sharing 85% or greater sequence identity, such as sharing 90% or greater sequence identity, with SEQ ID NO: 26;
(c) FR3 comprises a sequence sharing 8% or greater sequence identity, such as sharing 15% or greater sequence identity, such as sharing 20% or greater sequence identity, such as sharing 26% or greater sequence identity, such as sharing 32% or greater sequence identity, such as sharing 40% or greater
sequence identity, such as sharing 45% or greater
sequence identity, such as sharing 52% or greater
sequence identity, such as sharing 58% or greater
sequence identity, such as sharing 65% or greater
sequence identity, such as sharing 70% or greater
sequence identity, such as sharing 76% or greater
sequence identity, such as sharing 80% or greater
sequence identity, such as sharing 82% or greater
sequence identity, such as sharing 85% or greater
sequence identity, such as sharing 90% or greater
sequence identity, such as sharing 92% or greater
sequence identity, such as sharing 95% or greater
sequence identity, with SEQ ID NO: 27; and/or
(d) FR4 comprises a sequence sharing 5% or greater
sequence identity, such as sharing 10% or greater
sequence identity, such as sharing 20% or greater
sequence identity, such as sharing 30% or greater
sequence identity, such as sharing 40% or greater
sequence identity, such as sharing 50% or greater
sequence identity, such as sharing 60% or greater
sequence identity, such as sharing 70% or greater
sequence identity, such as sharing 80% or greater
sequence identity, such as sharing 90% or greater
sequence identity, with SEQ ID NO: 28.
87. The polypeptide according to clause 86, wherein FR1 comprises SEQ ID NO: 25 and/or FR2 comprises SEQ ID NO: 26 and/or FR3 comprises SEQ ID NO: 27 and/or FR4 comprises SEQ ID NO: 28.
88. The polypeptide according to any one of clauses 70 to 87 which comprises a sequence sharing 50% or greater
sequence identity, such as sharing 55% or greater
sequence identity, such as sharing 60% or greater
sequence identity, such as sharing 65% or greater
sequence identity, such as sharing 70% or greater
sequence identity, such as sharing 75% or greater
sequence identity, such as sharing 80% or greater
sequence identity, such as sharing 85% or greater
sequence identity, such as sharing 90% or greater
sequence identity, such as sharing 95% or greater
sequence identity, such as sharing 96% or greater
sequence identity, such as sharing 97% or greater
sequence identity, such as sharing 98% or greater
sequence identity, such as sharing 99% or greater
sequence identity, with SEQ ID NO: 21.
89. The polypeptide according to clause 88 which comprises or consists of SEQ ID NO: 21.
90 The polypeptide according to any one of clauses 1 to 89, wherein the polypeptide is an antibody.
91. The polypeptide according to clause 90, wherein the polypeptide is an antibody fragment.
92. The polypeptide according to clause 91, which is selected from the list consisting of: a VHH, a VH, a VL, a V-NAR, a Fab fragment and a F(ab')2 fragment.
93. The polypeptide according to clause 92, wherein the polypeptide is a VHH.
94. The polypeptide according to clause 92, wherein the polypeptide is a VH.
95. A construct comprising two or more identical polypeptides according to any one of clauses 1 to 94.
96. A construct comprising at least one polypeptide according to any one of clauses 1 to 94 and at least one different polypeptide, wherein the different polypeptide binds to TNF-alpha.
97. A construct comprising at least one polypeptide according to any one of clauses 1 to 94 and at least one different polypeptide, wherein the different polypeptide binds to a target other than TNF-alpha.
98. The construct according to any one of clauses 95 to 97 wherein the polypeptides are connected by at least one protease-labile linker.
99. The construct according to clause 98, wherein the protease-labile linker is of the format:

$$[-(G_aS)_x-B-(G_bS)_y-]_z$$

wherein
a is 1 to 10;
b is 1 to 10;
x is 1 to 10;
y is 1 to 10;
z is 1 to 10 and
B is K or R.
100. The construct according to clause 99 wherein a is 2 to 5, b is 2 to 5, x is 1 to 3, y is 1 to 3, z is 1 and B is K.
101. The construct according to clause 100 wherein the construct comprises or more suitably consists of SEQ ID NO: 46.
102. The construct according to any one of clauses 95 to 97 wherein the polypeptides are all connected by non-protease-labile linkers.
103. The construct according to clause 102, wherein the non-protease-labile linkers are of the format $$(G_4S)_x$$

wherein
x is 1 to 10.
104. The construct according to clause 103 wherein x is 6.
105. The polypeptide or construct according to any one of clauses 1 to 104, which neutralizes human IL-23 in the IL-23-IL-23R neutralisation ELISA (Evaluation Method A) with an EC50 of 5 nM or less, such as 4 nM or less, such as 3 nM or less, such as 2 nM or less, such as 1.7 nM or less, such as 1.5 nM or less, such as 1.4 nM or less, such as 1.3 nM or less, such as 1.2 nM or less, such as 1.1 nM or less, such as 1.0 nM or less, such as 0.9 nM or less, such as 0.8 nM or less, such as 0.75 nM or less, such as 0.70 nM or less, such as 0.65 nM or less, such as 0.60 nM or less, such as 0.55 nM or less, such as 0.50 nM or less, such as 0.45 nM or less, such as 0.40 nM or less, such as 0.35 nM or less, such as 0.30 nM or less, such as 0.25 nM or less, such as 0.20 nM or less.
106. The polypeptide or construct according to any one of clauses 1 to 105, which is substantially resistant to one or more proteases.
107. The polypeptide or construct according to clause 106, wherein the one or more proteases are present in the stomach or the small or large intestine.
108. The polypeptide or construct according to clause 107, wherein the one or more proteases are present in the small intestine.
109. The polypeptide or construct according to clause 106, wherein the one or more proteases are selected from the group consisting of enteropeptidase, trypsin, chymotrypsin and inflammatory bowel disease inflammatory proteases.
110. The polypeptide or construct according to clause 109, wherein the one or more proteases are selected from the group consisting of trypsin, chymotrypsin and inflammatory bowel disease inflammatory proteases.
111. The polypeptide or construct according to either clause 109 or 110, wherein the inflammatory bowel disease inflammatory proteases are one or more proteases selected from the group consisting of MMP3, MMP12 and cathepsin.

112. The polypeptide or construct according to clause 110, wherein the proteases are trypsin and chymotrypsin.

113. A pharmaceutical composition comprising the polypeptide or construct according to any one of clauses 1 to 112 and one or more pharmaceutically acceptable diluents or carriers.

114. The pharmaceutical composition according to clause 113 wherein the composition is presented in enterically coated form.

115. The pharmaceutical composition according to either clause 113 or 114 comprising at least one further active agent.

116. The pharmaceutical composition according to clause 115 wherein the at least one further active agent is selected from the list consisting of: 5-aminosalicylic acid, or a prodrug thereof (such as sulfasalazine, olsalazine or bisalazide); corticosteroids (e.g. prednisolone, methylprednisolone, or budesonide); immunosuppressants (e.g. cyclosporin, tacrolimus, methotrexate, azathioprine or 6-mercaptopurine); anti-TNF-alpha antibodies (e.g., infliximab, adalimumab, certolizumab pegol or golimumab); anti-IL12/1L23 antibodies (e.g., ustekinumab); anti-IL6R antibodies or small molecule IL12/1L23 inhibitors (e.g., apilimod); Anti-alpha-4-beta-7 antibodies (e.g., vedolizumab); MAdCAM-1 blockers (e.g., PF-00547659); antibodies against the cell adhesion molecule alpha-4-integrin (e.g., natalizumab); antibodies against the 1L2 receptor alpha subunit (e.g., daclizumab or basiliximab); JAK3 inhibitors (e.g., tofacitinib or R348); Syk inhibitors and prodrugs thereof (e.g., fostamatinib and R-406); Phosphodiesterase-4 inhibitors (e.g., tetomilast); HMPL-004; probiotics; Dersalazine; semapimod/CPSI-2364; and protein kinase C inhibitors (e.g. AEB-071).

117. The pharmaceutical composition according to clause 116 wherein the at least one further active agent is 5-aminosalicylic acid.

118. The polypeptide, pharmaceutical composition or construct according to any one of clauses 1 to 117 for use as a medicament.

119. The polypeptide, pharmaceutical composition or construct according to clause 118 for use in the treatment of an autoimmune and/or inflammatory disease.

120. The polypeptide, pharmaceutical composition or construct according to clause 119 wherein the autoimmune and/or inflammatory disease is selected from the list consisting of Crohn's disease, ulcerative colitis, irritable bowel disease, diabetes type II, glomerulonephritis, autoimmune hepatitis, Sjogren's syndrome, celiac disease, drug- or radiation-induced mucositis, pemphigus, psoriasis, eczema and scleroderma.

121. The polypeptide, pharmaceutical composition or construct for use according to clause 120, wherein the autoimmune and/or inflammatory disease is Crohn's disease.

122. The polypeptide, pharmaceutical composition or construct for use according to any one of clauses 118 to 121, which is administered orally.

123. The polypeptide, pharmaceutical composition or construct for use according to any one of clauses 118 to 119, which is administered topically to the skin.

124. Use of the polypeptide, pharmaceutical composition or construct according to any one of clauses 1 to 117 in the manufacture of a medicament for the treatment of autoimmune and/or inflammatory disease.

125. Use of the polypeptide, pharmaceutical composition or construct according to clause 124 wherein the autoimmune and/or inflammatory disease is selected from the list consisting of Crohn's disease, ulcerative colitis, irritable bowel disease, diabetes type II, glomerulonephritis, autoimmune hepatitis, Sjogren's syndrome, celiac disease, drug- or radiation-induced mucositis, pemphigus, psoriasis, eczema and scleroderma.

126. The use according to clause 125 wherein the autoimmune and/or inflammatory disease is Crohn's disease.

127. The use according to any one of clauses 124 to 126 wherein the medicament is administered orally.

128. The use according to clause 124 wherein the medicament is administered topically to the skin.

129. A method of treating autoimmune and/or inflammatory disease comprising administering to a person in need thereof a therapeutically effective amount of the polypeptide, pharmaceutical composition or construct according to any one of clauses 1 to 117.

130. The method of treating autoimmune and/or inflammatory disease according to clause 129 wherein the autoimmune and/or inflammatory disease is selected from the list consisting of Crohn's disease, ulcerative colitis, irritable bowel syndrome, diabetes type II, glomerulonephritis, autoimmune hepatitis, Sjogren's syndrome, celiac disease, drug- or radiation-induced mucositis, pemphigus, psoriasis, eczema and scleroderma.

131. The method of treating autoimmune disease according to clause 130 wherein the autoimmune disease is Crohn's disease.

132. The method of treating autoimmune disease according to any one of clauses 129 to 131 wherein the polypeptide, pharmaceutical composition or construct is administered orally.

133. The method of treating autoimmune disease according to clause 129 wherein the polypeptide, pharmaceutical composition or construct is administered topically to the skin.

134. The polypeptide, pharmaceutical composition, construct, use or method according to any one of clauses 118 to 133 wherein the polypeptide, pharmaceutical composition or construct is administered sequentially, simultaneously or separately with at least one active agent selected from the list consisting of 5-aminosalicylic acid, or a prodrug thereof (such as sulfasalazine, olsalazine or bisalazide); corticosteroids (e.g. prednisolone, methylprednisolone, or budesonide); immunosuppressants (e.g. cyclosporin, tacrolimus, methotrexate, azathioprine or 6-mercaptopurine); anti-TNF-alpha antibodies (e.g., infliximab, adalimumab, certolizumab pegol or golimumab); anti-IL12/1L23 antibodies (e.g., ustekinumab); anti-IL6R antibodies or small molecule IL12/IL23 inhibitors (e.g., apilimod); Anti-alpha-4-beta-7 antibodies (e.g., vedolizumab); MAdCAM-1 blockers (e.g., PF-00547659); antibodies against the cell adhesion molecule alpha-4-integrin (e.g., natalizumab); antibodies against the IL2 receptor alpha subunit (e.g., daclizumab or basiliximab); JAK3 inhibitors (e.g., tofacitinib or R348); Syk inhibitors and prodrugs thereof (e.g., fostamatinib and R-406); Phosphodiesterase-4 inhibitors (e.g., tetomilast); HMPL-004; probiotics; Dersalazine; semapimod/CPS1-2364; and protein kinase C inhibitors (e.g. AEB-071).

135. The polypeptide, pharmaceutical composition, construct or method according to clause 134 wherein the polypeptide, pharmaceutical composition or construct is administered sequentially, simultaneously or separately with infliximab, adalimumab, certolizumab pegol or golimumab.
136. A polynucleotide comprising or consisting of a sequence sharing 70% or greater, such as 80% or greater, such as 90% or greater, such as 95% or greater, such as 99% or greater sequence identity with any one of the portions of SEQ ID NO: 10 which encode CDR1, CDR2 or CDR3 of the encoded immunoglobulin chain variable domain.
137. A polynucleotide encoding the polypeptide or construct according to any one of clauses 1 to 135.
138. The polynucleotide according to clause 137, wherein the polynucleotide comprises or consists of a sequence sharing 70% or greater, such as 80% or greater, such as 90% or greater, such as 95% or greater, such as 99% or greater sequence identity with SEQ ID NO: 10.
139. The polynucleotide according to clause 138, wherein the polynucleotide comprises or consists of SEQ ID NO: 10.
140. A cDNA comprising the polynucleotide according to any one of clauses 136 to 139.
141. A vector comprising the polynucleotide or cDNA according to any one of clauses 136 to 140.
142. A host cell transformed with a vector according to clause 141 and which is capable of expressing the polypeptide or construct according to any one of clauses 1 to 112.
143. The host cell transformed with a vector according to clause 142 wherein the host cell is a yeast cell such as *S. cerevisiae* or *P. pastoris*.
144. The host cell transformed with a vector according to clause 142 wherein the host cell is a bacterial cell such as *E. coli*.
145. A process for the preparation of the polypeptide or construct according to any one of clauses 1 to 112, comprising the following steps:
    i) cloning into a vector, such as a plasmid, the polynucleotide according to any one of clauses 136 to 139
    ii) transforming a cell, such as a bacterial cell or a yeast cell capable of producing the polypeptide or construct according to any one of clauses 1 to 112, with said vector in conditions allowing the production of the polypeptide or construct,
    iii) recovering the polypeptide or construct, such as by affinity chromatography.

Additional Clauses Setting Out Further Embodiments of the Invention are as Follows:
1. A polypeptide comprising an immunoglobulin chain variable domain which binds to IL-23, wherein the immunoglobulin chain variable domain comprises three complementarity determining regions (CDR1-CDR3) and four framework regions (FR1-FR4), wherein CDR1 comprises a sequence sharing 60% or greater sequence identity with SEQ ID NO: 1, CDR2 comprises a sequence sharing 50% or greater sequence identity with SEQ ID NO: 2 and CDR3 comprises a sequence sharing 50% or greater sequence identity with SEQ ID NO: 3.
2. The polypeptide according to clause 1, wherein CDR1 comprises a sequence sharing 80% or greater sequence identity with SEQ ID NO: 1, CDR2 comprises a sequence sharing 80% or greater sequence identity with SEQ ID NO: 2 and CDR3 comprises a sequence sharing 80% or greater sequence identity with SEQ ID NO: 3.
3. The polypeptide according to clause 3, wherein CDR1 consists of SEQ ID NO: 1, CDR2 consists of SEQ ID NO: 2 and CDR3 consists of SEQ ID NO: 3.
4. The polypeptide according to any one of clauses 1 to 3, wherein FR1 comprises a sequence sharing 80% or greater sequence identity with SEQ ID NO: 4, FR2 comprises a sequence sharing 80% or greater sequence identity with SEQ ID NO: 5, FR3 comprises a sequence sharing 80% or greater sequence identity with SEQ ID NO: 6 and FR4 comprises a sequence sharing 80% or greater sequence identity with SEQ ID NO: 7.
5. The polypeptide according to any one of clauses 1 to 4 which comprises a sequence sharing 70% or greater sequence identity with SEQ ID NO: 8.
6. The polypeptide according to any one of clauses 1 to 5 wherein the polypeptide is an antibody or fragment thereof.
7. The polypeptide according to clause 6 wherein the polypeptide is a VH or a VHH.
8. A construct comprising at least one polypeptide according to any one of clauses 1 to 7 and at least one different polypeptide, wherein the different polypeptide binds to TNF-alpha.
9. The construct according to clause 8 wherein the polypeptides are connected by at least one protease-labile linker.
10. The polypeptide or construct according to any one of clauses 1 to 9, wherein the polypeptide or construct neutralizes human IL-23 in the IL-23-IL-23R neutralisation ELISA (Evaluation Method A) with an EC50 of 2 nM or less.
11. The polypeptide or construct according to any one of clauses 1 to 10, wherein the polypeptide or construct is substantially resistant to one or more proteases present in the small intestine.
12. The polypeptide or construct according to clause 11, wherein the proteases are trypsin and chymotrypsin.
13. The polypeptide, pharmaceutical composition or construct according to any one of clauses 1 to 12 for use in the treatment of an autoimmune and/or inflammatory disease.
14. The polypeptide, pharmaceutical composition or construct for use according to clause 13, wherein the polypeptide, pharmaceutical composition or construct for use is administered orally.
15. A polynucleotide encoding the polypeptide or construct according to any one of clauses 1 to 14.

The present invention will now be further described by means of the following non-limiting examples.

EXAMPLES

Evaluation Methods Used in the Examples
Evaluation Method A: IL-23-IL-23R Neutralisation ELISA
Maxisorp 96-well plates were coated overnight with 50 μl/well 0.3 μg/ml IL-23R-Fc then blocked with 4% milk, 1% BSA. ICVDs were serially diluted in 4% milk, 1% BSA and mixed 1:1 with 40 ng/ml recombinant human IL-23. ICVDs mixed with IL-23 were afterwards added to the IL-23R-coated plates. Bound IL-23 was detected with BAF219 anti-p40 biotinylated pAb (R&D systems) followed by Extravidin-HRP. This allowed calculation of the IL-23 neutralising activity in the sample.
Evaluation Method B: IL-23-IL-23R Neutralisation ELISA Using a High Salt Buffer
A high salt IL-23-IL-23R ELISA was used to measure anti-IL-23 ICVD concentrations in faecal extracts. This ELISA was the same as the ELISA above (Evaluation Method A) except that the buffer used for the faecal supernatant dilution and IL-23 preparation was 1% BSA, 4% milk in PBS containing 0.6M NaCl, 0.05% Tween20 and protease inhibitors.

Evaluation Method C: Mouse Splenocytes Assay

Splenocytes were isolated from mouse spleen and plated in 96-well round-bottom microplates at $4\times10^5$ cells/50 µL/well in culture medium containing 20 ng/mL mouse IL-2 (2× the assay concentration). Top concentrations of ICVDs were prepared at 300 nM (2×) in culture medium containing 10 ng/mL THP-1 derived nhIL-23 (2x the assay concentration), and subsequent 2.6 fold dilutions were made directly in culture medium containing nhIL-23 (2×). 50 µL of each ICVD mix (2×) were then transferred onto cells (50 µL) to obtain a final 1x assay concentration of ICVD, hIL-23, and mIL-2. 'mIL-2 only' and 'mIL-2+hIL-23' were used as negative and positive controls, respectively, for mouse IL-17 stimulation and secretion in culture supernatants. Following 3 days incubation at 37° C., 5% $CO_2$, plates were spun for 2 minutes at 2000 rpm and 50 µL of culture supernatant were recovered from each well. Levels of mIL-17 in the culture supernatants were measured using an IL-17 binding ELISA and the neutralization of hIL-23 was determined.

Example 1: Immunisations, Phage Library Selections, Master Plate Screening and Production of ICVDs in *E. coli*

Example 1.1: Immunisation and Phaqe Library Construction

Llamas were immunised with soluble human recombinant IL-23 and good titres of serum antibodies were obtained in both animals. RNA was isolated from white blood cells collected from each llama following several boosting immunisations of IL-23.

Peripheral blood mononuclear cells (PBMCs) collected from each llama at the end of each immunisation phase were used to generate seven separate phage display libraries. Construction of the ICVD phage display libraries and the primary selection of phages expressing ICVDs with IL-23-binding activity were performed using standard reagents and protocols. In general, total RNA was extracted from the peripheral blood lymphocytes that were isolated from each of the immunised llamas. The RNA was then used to generate cDNA and PCR was performed to amplify specifically the variable regions of ICVD heavy chain only antibodies. cDNA fragments encoding the ICVD repertoire were cloned into a phagemid vector and the library introduced into *E. coli*. The phage libraries were produced by culturing the *E. coli* with helper phage, and precipitation of the resulting ICVD-displaying phage. The numbers in each library were determined by titration and infection of log-phase *E. coli* strain TG1 with the different dilutions. The libraries were each estimated to contain between $6\times10^7$ and $5\times10^8$ ICVD sequences.

Example 1.2: Library Selections for Phages with Human IL-23-Binding Activity: Propagation and Generation of Periplasmic Extracts Phage library selection strategies were set up to enrich for ICVD that bind specifically to the IL-23p19 subunit. Phages were selected for by panning on either hIL-23 or biotinylated hIL-23 in the presence of soluble hIL-12. Bound ICVDs were washed using different methods and removed from the plates using either specific elution with IL-23R or total elution with TEA. The selection and elution conditions were established to isolate ICVDs that bind with high affinity to epitopes of p19 that are present on the active soluble form of IL-23 and that interfere with the binding of IL-23 to the IL-23 receptor (IL-23R).

Phages present in eluates from the selections were used to infect *E. coli* TG1 cells. Colonies were picked randomly into twelve 96-well master plates and propagated to generate clonal cultures. Bacterial cell outer membranes were lysed by freeze-thawing to release the ICVD-containing periplasmic fraction (also referred to herein as "peri"). Cell debris was removed by centrifugation and the supernatants transferred to fresh 96-well plates for evaluation of ICVD properties.

Example 1.3: Screening of Periplasmic Extracts

In order to identify ICVDs specific for inhibiting IL-23 signalling, periplasmic extracts were tested for their ability to disrupt three interactions: 1) IL-23 binding to IL-23R, 2) IL-23 binding to IL-12Rβ1, and 3) IL-12 binding to IL-12Rβ1. These interactions were each tested by ELISA.

Three plate-ELISA formats were developed whereby periplasmic extracts containing the ICVD were mixed with the appropriate cytokine before applying the mixture to a Maxisorp plate coated with the appropriate cytokine receptor. In the absence of interference in cytokine-receptor binding by the ICVD, this allowed capture of the cytokine, which in all cases could be detected by a biotinylated anti-p40 antibody and, subsequently, Extravidin-HRP. The neutralising activity of each ICVD was measured as the ability to reduce binding of the cytokine to its receptor relative to an "irrelevant" VHH control. Promising ICVD clones were selected for production in *E. coli* and further evaluation.

Example 1.4: Production of Selected Clones in *E. coli*

DNA sequences of selected ICVDs were re-cloned into the vector pMEK222 (thus introducing C-terminal FLAG and 6×His tags) for production in *E. coli* and the ICVDs affinity purified on Talon resin via the 6×His tag for more detailed evaluation studies. ICVDs that failed to express well from *E. coli* were excluded from further analysis.

Example 2: Potency of Purified Primary Clones

IL-23-IL-23R-neutralising activities of the purified ICVDs were evaluated in an IL-23-IL-23R neutralisation ELISA (Evaluation Method A) to assess potency against human IL-23. The ICVDs found to have had higher potency than comparative example monoclonal antibody brazikumab (heavy chain SEQ ID NO: 70, light chain SEQ ID NO: 71) are set out in the table below.

| Clone # | Family | IL-23:IL-23R ELISA EC50 (nM) |
|---|---|---|
| 12G1 | L | 0.387 |
| 1E2 | L | 0.546 |
| 10E2 | — | 1.454 |
| 10G10 | — | 1.466 |
| Brazikumab (comparative example) | — | 2.23 |

The ELISA results showed that Family L clones (12G1 and 1E2) are remarkably potent, not only displaying higher potency in the IL-23-IL-23R ELISA than the comparative example anti-IL-23 antibody brazikumab, but even displaying sub-nanomolar potency. Clones 10E2 and 10G10 also demonstrated higher potency in this assay than the brazikumab comparative example.

10E2, 12G1 and 1E2 were also tested in a cynomolgus monkey IL-23-IL-23R neutralisation ELISA and all showed high neutralising potencies in this assay (data not shown), similar to those demonstrated in the standard IL-23-IL-23R ELISA. It was also established that these clones were not capable of neutralising the interaction of IL-23 with IL-12R or IL-12 with IL-12R. Whilst not wishing to be bound by theory, the inventors believe that these clones are specific for the p19 subunit of IL-23.

Example 3: Intrinsic Protease Stability of Purified Primary Clones

Orally administered ICVDs are likely to be susceptible to proteolytic digestion during passage through the small and large intestines. To further investigate resistance to intestinal proteases, the (retention of) potency of purified ICVDs was tested after incubation in the presence of both mouse small intestinal supernatant and a supernatant prepared from pooled human faecal samples.

Mouse small intestinal supernatant: the contents of the small intestines from seven C57BL/6 male mice were removed with 0.9% saline, combined, homogenised and centrifuged. The resulting supernatant was removed, aliquoted and frozen.

Human faecal supernatant: faecal samples from five humans were turned into slurries with addition of 1x PBS. The slurries were then pooled, centrifuged and the supernatants removed, aliquoted and stored at −80° C. This process removes the faecal matrix, including any cellular material.

Following incubation of the ICVDs for different periods at 37° C., anti-IL-23 activities of the "digested" ICVD samples were assayed using the IL-23-IL-23R neutralisation ELISA (Evaluation Method B) and the percentage of activity maintained from the "undigested" ICVD to the "digested" ICVD calculated. The results are provided in the table below.

| Clone # | Family | Protease stability | |
| --- | --- | --- | --- |
| | | 1 hour digestion in mouse small intestinal material | 4 hours digestion in human faecal material |
| 12G1 | L | 51.2% | 5.6% |
| 1E2 | L | 41.3% | 6.1% |
| 10E2 | — | 19.3% | 14.3% |

The ICVDs demonstrated substantial intrinsic stability to proteases present in mouse small intestinal material and human faecal material. The Family L ICVD 12G1 was chosen for further optimisation based on its potency and intrinsic protease resistance.

Example 4: Production and Characterisation of Optimised Variants of 12G1

The Family L ICVD 12G1 underwent sequence modification to produce multiple variant ICVDs. These variant ICVDs were tested in the potency and protease stability assays detailed above. The variant ICVDs, their mutations relative to ID-L253T and their performance in these assays are detailed in the table below (wherein EC50 values are provided in nM, 'mouse splenocyte' refers to data obtained using Evaluation Method C above and residues are numbered using N- to C-terminal numbering, as opposed to Kabat numbering).

It was noted that high potency and protease stability was generally maintained amongst the variant ICVDs. Variants of ID-L253T may therefore be expected to generally substantially maintain high potency and protease stability.

Of these variant ICVDs, ID-L253T was finally chosen to be taken forward for further characterisation. 12G1 varies from ID-L253T by the following mutations: E1D, L11Q, R19S, A23E, A24S, Y37F, A60S, M69I, V78L, F79Y, E81Q, D83N, V85L, A90T, N96A, L103I and R116Q (using N- to C-terminal numbering, as opposed to Kabat numbering).

| clone # | Mutations relative to ID-L253T | Potency (EC50) | Protease stability | | | | Mouse splenocyte |
| --- | --- | --- | --- | --- | --- | --- | --- |
| | | | Mouse SI material | | Human Faecal material | | |
| | | | Pool A 4 h | Pool B 4 h | 7 h | 16 h | |
| ID-L210T | D1E, S19R, V92R | 0.32 ± 0.17* | 57.4% ± 15 | 53.4% ± 23 | 37% ± 13 | 23.4% ± 5.1 | 5.63 ± 2.1 |
| ID-L237T | D1E, V92R | 0.24 | 58.0% | — | 56.0% | 26.0% | 6.35 |
| ID-L238T | D1E, S19R, V40A, V92R | 0.2 | 71.0% | — | 34.7% | 26.0% | 5.54 |
| ID-L239T | D1E, S19R, R45L, V92R | 0.26 | 95.0% | — | 35.5% | 24.0% | 3.84 |
| ID-L240T | D1E, S19R, D58H, Y59D, S60G, V63A, V92R | not tested | 5.0% | — | 2.5% | not tested | not tested |
| ID-L241T | D1E, S19R, D58H, V92R | 0.31 | 89.0% | — | 33.9% | 28.0% | 3.51 |
| ID-L242T | D1E, S19R, S60R, V92R | 0.22 | 80.0% | — | not tested | 7.3% | 3.01 |
| ID-L243T | D1E, S19R, P87S, V92R | 0.27 | 69.0% | — | 46.3% | 20.0% | 5.00 |
| ID-L244T | D1E, S19R | 0.24 | 84.0% | — | 48.0% | 23.0% | 6.62 |
| ID-L245T | D1E | 0.25 ± 0.1 | 38.7% | 56.7% | 53% ± 7 | 28% ± 2 | 3.99 or 13.67 |
| ID-L246T | D1E, V40A, I69L, L78V | 2.15 | not tested | — | not tested | not tested | not tested |
| ID-L247T | D1E, V40A, R45L | 0.31 | 51.8% | — | 55% ± 14 | 28% ± 7 | 4.52 |
| ID-L248T | D1E, K43H, R45L | 0.17 | 39.3% | — | 61% ± 13 | 27.0% | 4.47 |
| ID-L249T | D1E, V40A, R45L, D58H | 0.74 | 55.7% | — | 55.3% | 27.5% | 4.27 |
| ID-L250T | D1E, V40A, R45L, L47F, D58H | 6.95 | not tested | — | not tested | not tested | not tested |
| ID-L251T | D1E, S19R, Q44E, L47F, D58H | 1.99 | 23.8% | 54.3% | 31.9% | 13.5% | 5.74 |

-continued

| | | | Protease stability | | | |
| --- | --- | --- | --- | --- | --- | --- |
| | | | Mouse SI material | | | |
| | | Potency | Pool A | Pool B | Human Faecal material | Mouse |
| clone # | Mutations relative to ID-L253T | (EC50) | 4 h | 4 h | 7 h | 16 h | splenocyte |
| ID-L252T | D1E, V40A, Q44E, R45L, I69L, L78V | 0.26 | 38.8% | — | 42% ± 5 | 25% ± 1 | 5.20 |
| ID-L253T | — | 0.23 ± 0.04 | — | 51% ± 16 | — | 29% | 13.51 ± 4.32 |

*average of 5 independent experiments excluding 1 experiment where an outlier value of 1.1 nM was obtained
**average of 8 independent experiments, excluding 1 experiment where an outlier value of 1.03 nM was obtained

Example 5: ID-L253T Potency, Binding Affinity and Protease Stability Compared to Comparative Examples Brazikumab and 37D5

Brazikumab is a fully human IgG$_2$ monoclonal antibody of the prior art that selectively binds the p19 subunit of IL-23. 37D5 is a domain antibody (VHH) of the prior art that selectively binds the p19 subunit of IL-23 (Desmyter et al 2017, SEQ ID NO: 69). The potency, binding affinity and protease stability of ID-L253T was assessed relative to these anti-IL-23 agents of the prior art.

Example 5.1: Potency of ID-L253T Compared to Brazikumab

ID-L253T and clinical comparator brazikumab were tested, side-by-side, for potency in the IL-23-IL-23R inhibition ELISA (Evaluation Method A). The results are summarised in the table below.

| Anti-IL-23 agent | IL-23-IL-23R ELISA (EC$_{50}$, nM) |
| --- | --- |
| ID-L253T | 0.202 |
| Brazikumab (comparative example) | 0.441 |

As expected based on the potency of progenitor ICVD 12G1 and variants of ID-L253T described above, ID-L253T demonstrated higher potency than brazikumab in the IL-23-IL-23R ELISA.

Example 5.2: Affinity of ID-L253T Compared to Brazikumab Fab

The binding kinetics of ID-L253T were compared against a brazikumab Fab (prepared using a commercially available Fab preparation kit) and assessed in a Biacore study. An anti-p40 mAb was fixed to the Biacore sensor plate and loaded with recombinant human IL-23. This tethering of IL-23 by its p40 subunit allows the p19 subunit (to which both brazikumab and ID-L253T are specific) to interact with the anti-IL-23 ID-253T ICVD and brazikumab Fab fragment, which were subsequently flowed over the chip to detect binding. ID-L253T had an average K$_D$ of 32 pM, while the brazikumab Fab preparation had a much higher average K$_D$ of 1200 pM, demonstrating that a brazikumab Fab has a much lower binding affinity than ID-L253T. These data are summarised in the table below.

| Anti-IL-23 agent | K$_D$ (pM) |
| --- | --- |
| ID-L253T | 32 |
| Brazikumab Fab (comparative example) | 1200 |

Whilst not wishing to be bound by theory, based on the data provided above, the inventors expect that ID-L253T binds to the p19 subunit of IL-23.

Example 5.3: Protease Stability of ID-L253T Compared to 37D5

The stability of ID-L253T in mouse small intestinal material was tested and compared to that of comparative example 37D5. Anti-IL-23 activities of the "digested" ICVD samples were assayed using the IL-23-IL-23R neutralisation ELISA (Evaluation Method B) and the percentage of activity maintained from the "undigested" ICVD to the "digested" ICVD calculated. These data are summarised in the table below.

| | 2 hour digestion in mouse small intestinal material | 4 hour digestion in mouse small intestinal material |
| --- | --- | --- |
| ID-L253T | Not tested | 51% |
| 37D5 | 0% | Not tested |

It is clear from these data that no ELISA signal could be established in respect of 37D5 after 2 hours digestion in mouse small intestinal material, whereas after an incubation period twice as long, ID-L253T achieved 51% survival. ID-L253T is therefore markedly more stable in this digestive matrix than comparative example 37D5. Note that the data provided here on ID-L253T corresponds to the same assay as that detailed above in Example 4 and the data provided here on 37D5 was produced in a separate assay on a different occasion.

Example 6: ID-L253T Specificity for Human IL-23

Example 6.1: Cross-Reactivity with IL-23 from Toxicological Species

A cynomolgus monkey IL-23-IL-23R neutralisation ELISA was performed. To this end, Maxisorp 96-well plates were coated overnight with 50 µl/well 0.5 µg/ml cynomolgus monkey IL-23R-Fc then blocked with 4% milk, 1% BSA. ICVDs were serially diluted in 4% milk, 1% BSA and mixed 1:1 with 40 ng/ml recombinant cynomolgus monkey IL-23 (cIL-23), then incubated for 30 minutes to allow binding before adding to the cIL-23R-coated plates. Bound cIL-23 was detected with BAF219 anti-p40 pAb and then Extravidin-HRP, and the level of neutralisation by the ICVD of cIL-23 binding to cIL-23R was determined.

ID-L253T was active in the cynomolgus monkey IL-23-IL-23R neutralisation assay (data not shown) making the cynomolgus monkey a suitable toxicology species for any preclinical development studies.

Example 6.2: Specificity Against Non-Target Cytokines

ID-L253T was tested for selectivity against IL-23-related and non-related cytokines in either binding or inhibition ELISAs. IL-12 shares the p40 subunit with IL-23 and is therefore the most closely-related cytokine in humans. Human and rhesus monkey IL-12 alongside a further member of the IL-12 cytokine family, IL-27, were tested in this assay. Additional important, but non-related, inflammatory cytokines TNFα, IL-6 and IFNγ were also tested. ID-L253T showed no interaction with the cytokines tested. This indicates that binding of ID-L253T to off-target molecules would be very unlikely in humans and non-human primates.

Example 7: Further Protease Stability Investigations on ID-L253T—Resistance to Gastrointestinal Matrix Metalloproteinases and Mouse Gastrointestinal Transit

Example 7.1: Resistance to Gastrointestinal Matrix Metalloproteinases

Levels of activated matrix metalloproteinases (MMPs) are increased in the inflamed mucosa of patients with inflammatory bowel disease. These MMPs are able to digest native human IgG and therapeutic agents that contain a human IgG scaffold (Biancheri et al, 2015). In the case of the anti-TNFα therapy etanercept, this digestion causes a significant reduction in TNFα neutralising potency. To confirm that ID-L253T is resistant to MMPs, ID-L253T was incubated for approximately 20 hours in the presence of activated recombinant human MMP3 and MMP12. ID-L253T demonstrated full survival over the course of approximately 20 hours whereas etanercept was degraded by the same enzyme preparations.

ID-L253T is fully resistant to digestion by MMP3 and MMP12 over the course of approximately 20 hours at 37° C. This indicates that ID-L253T should retain high stability in the inflamed environment of the IBD gut, where levels of MMPs are elevated. This finding, along with the findings above in relation to general protease resistance, suggest that polypeptides of the invention have great potential as an oral therapy for IBD.

Example 7.2: Mouse Gastrointestinal Transit and Survival

Results of in vitro studies described above showed that ID-L253T was resistant to inactivation by proteases present in a supernatant extract prepared from mouse small intestinal contents. In the author's experience, mouse small intestinal supernatant is much more proteolytically active than small intestinal supernatants obtained from humans or pigs. A study was performed to investigate the stability of ID-L253T during passage through the gastrointestinal system of the mouse. ID-L253T was formulated with anti-TNF-alpha ICVD ID-38F (see WO2016156465, SEQ ID NO: 8 and Example 8 therein) in a milk and bicarbonate mixture. ID-38F has been previously established to be stable during mouse gastrointestinal transit and therefore acts as a positive control here. Following co-administration of the ICVDs to four mice by oral gavage, concentrations of the ICVDs in faecal pellets collected between 0 h-3 h and 3 h-6 h were measured.

ID-L253T was detected at both 0-3 h and 3-6 h after dosing at levels comparable to those of ID-38F in the same mice. The results showed that ID-L253T survives as well as, or better than ID-38F in mice, reaching highest recovery concentrations over 15 pM in supernatants from faecal pellets collected 3-6 h after dosing.

Example 8: Assessment of ID-L210T Neutralising Activity in Human IBD Tissue

The IL-23 neutralising activity of ID-L210T, a variant of ID-L253T lacking only the E1D, R19S and R92V mutations, was investigated in ex vivo cultures of inflamed colonic mucosal tissue using the assay system described by Vossenkamper et al (2014) and Crowe et al (2018).

Use of this model tested the inhibitory effects of ID-L210T on the raised levels of signalling phosphoproteins that exist in IBD disease tissue under pathophysiological conditions. The study was conducted using biopsy tissue samples from four patients with active UC. Following 24 h incubation with either ID-L210T (at 150 nM concentration) or an isotype control ICVD which does not bind to IL-23 (ID-2A, an irrelevant anti-*C. difficile* toxin ICVD, at 225 nM concentration), biopsy explants were analysed for levels of phosphoproteins using proteome profiler human phosphokinase array technology.

Figure 2:
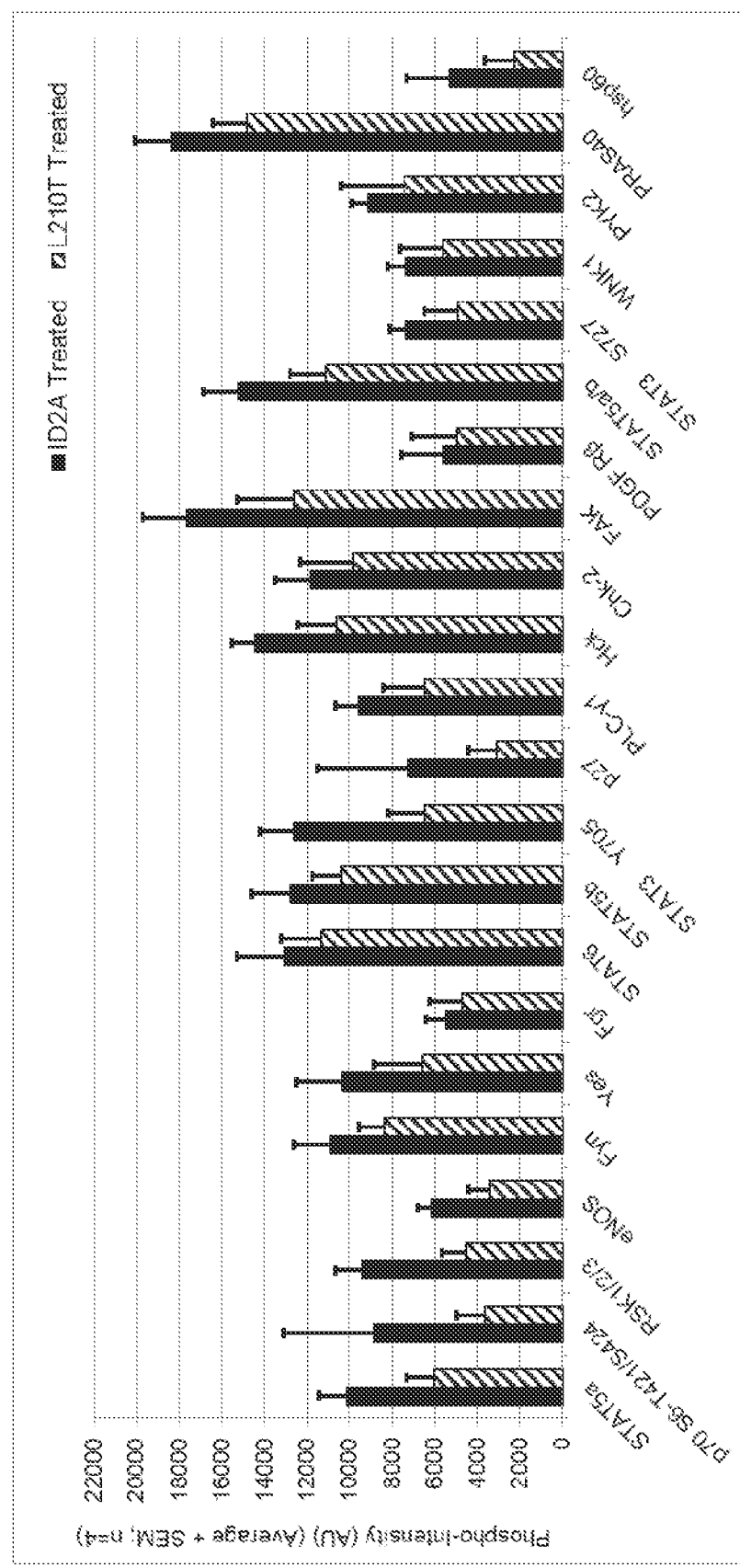

The average phospho-intensity values for all patients in respect of the various proteins tested are shown in FIGS. 1-2. The phosphorylation levels of most proteins on the array were decreased following treatment with ID-L210T.

The effect of treatment on the total protein phosphorylation signal ($\Sigma_{n=39}$ phosphoproteins) detected for each biopsy was also assessed. After treatment with ID-L210T the total phosphorylation levels measured in biopsies from all of the UC patients were inhibited by (20-52%; average 32% n=4).

ID-L253T differs from ID-L210T in only three amino acids, shows similar IL-23-IL-23R inhibition potencies, resistance to in vitro digestion and transit through the mouse. These findings in respect of ID-L210T are therefore expected to be substantially applicable to ID-L253T.

Example 9: Yeast Productivity in Fermentation Culture

An *S. cerevisiae* production strain expressing ID-L253T was inoculated into a 5-litre fermentation. Production levels were assessed by SDS-PAGE with Coomassie staining, and biological activity was assessed by IL-23-IL-23R neutralisation ELISA. The results showed a clean band in the end of fermentation (EoF) supernatant at the correct molecular weight, with very few contaminants. The yield of ID-L253T was measured as 0.188 g/L.

ID-L253T was also tested for production in *P. pastoris* using standard yeast fermentation technology. Production levels were assessed by SDS-PAGE with Coomassie staining, and the results showed a clean band in the EoF supernatant at the correct molecular weight. The yield of ID-L253T from this fermentation was measured as 1.3 g/L. Full neutralising activity was demonstrated by IL-23-IL-23R neutralisation ELISA.

Example 10: Production and Characterisation of Heterobihead Anti-IL-23/Anti-TNF-Alpha Construct FA1K Example 10.1: Production of FA1K A heterobihead construct comprising the anti-IL-23 ICVD ID-L253T and the anti-TNF-alpha ICVD ID-38F (WO2016156465, SEQ ID NO: 8 therein and SEQ ID NO: 67 in this disclosure) was produced (herein referred to as 'FA1K'). The ICVDs in this construct were separated by a flexible, non-immunogenic $(G_4S)_4$ linker with a central lysine residue (SEQ ID NO: 49) to create a trypsin-cleavable site (ID-38F-$(G_4S)_2$-K-$(G_4S)_2$-ID-L253T), of the type disclosed in WO2016156466. The polypeptide sequence of the ID-38F arm used in FA1K was identical to that of ID-38F used above (SEQ ID NO: 47) and the polypeptide sequence of the ID-L253T arm used in FA1K was identical to that used for ID-L253T above but for a D1E substitution (SEQ ID NO: 48).

FA1K was cloned on a SacI/HindIII fragment into vector pUR9013 to facilitate stable, multi-copy, integration into the chromosome of the S. cerevisiae vwkgal1⁻ expression strain. Using this integration and expression system, FA1K was under the control of a galactose-inducible promoter in S. cerevisiae and bihead secretion was achieved via a yeast mating factor alpha signal sequence. In addition, FA1K with the same signal sequence was cloned into the chromosome of P. pastoris under the control of the methanol-inducible pAOX1 promoter. Expression of FA1K from S. cerevisiae was assessed in 50 mL induction cultures.

The supernatant from these shake flasks was purified. This purified preparation of FA1K was subsequently used for the experiments described below, unless stated otherwise.

FA1K was also cloned into P. pastoris and demonstrated excellent expression at 50 mL scale.

Example 10.2: In Vitro Characterisation of FA1K

Incubation of FA1K with trypsin at 37° C. resulted in rapid separation of the ID-L253T and ID-38F monomer arms. FA1K is therefore well-formatted for quick release of both monomer arms on exposure to trypsin in the human small intestine.

Figure 3:
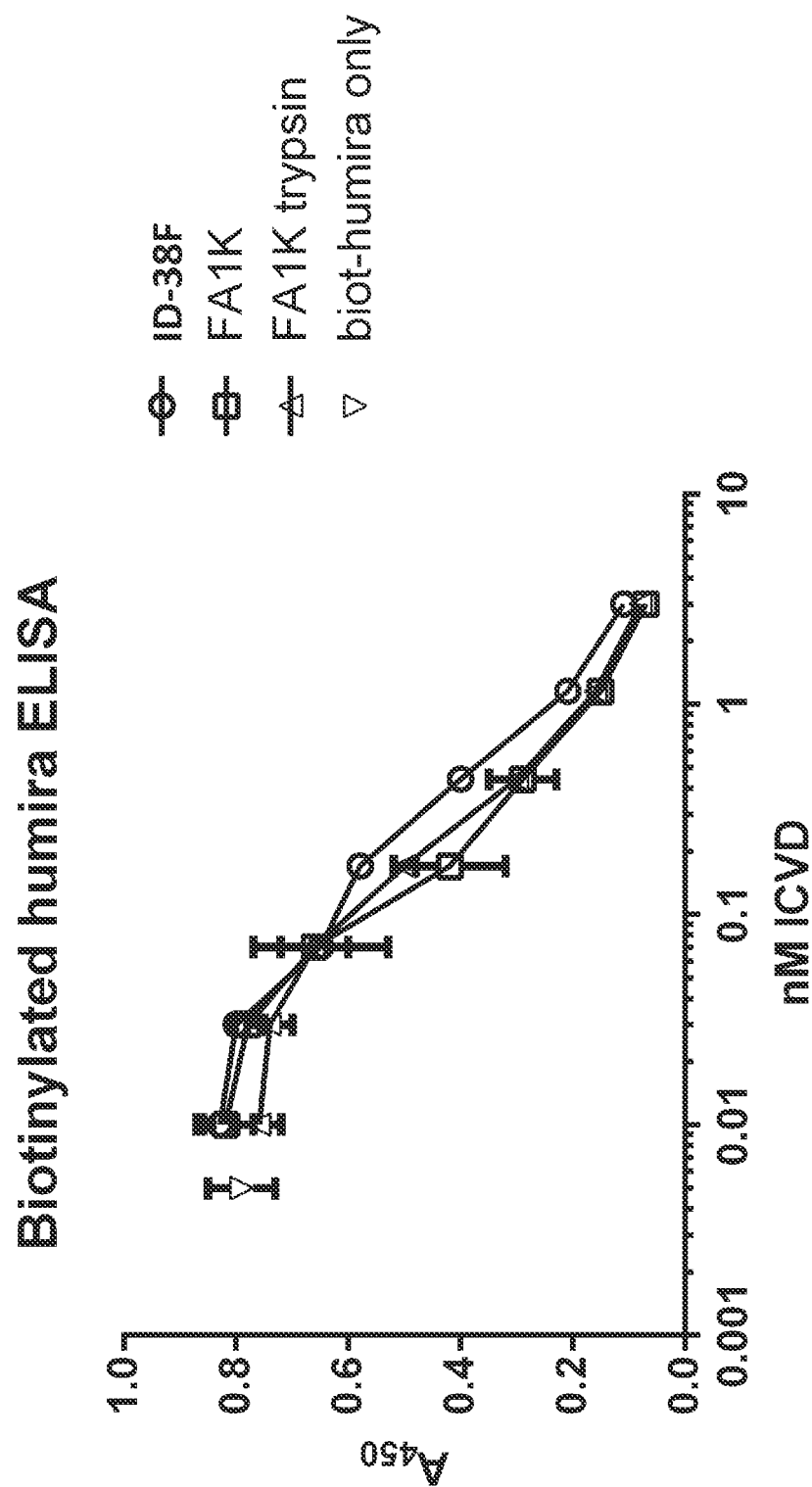
FIG. 3—Neutralising potency of FA1K (pre- and post-trypsin cleavage) against TNF-alpha FIG. 4—Neutralising potency of FA1K (pre- and post-trypsin cleavage) against IL-23

The neutralising potency of FA1K (pre- and post-trypsin cleavage) against TNF-alpha was investigated (see FIG. 3 wherein 'FA1K' refers to FA1K pre-trypsin treatment and 'FA1K trypsin' refers to FA1K post-trypsin treatment).

A biotinylated humira (adalimumab) competition ELISA was performed which measures competition for an epitope on TNF-alpha. When competition occurs, the epitope is occupied by an unlabelled polypeptide and less biotinylated humira binds to TNFα, resulting in a lowered assay signal. ELISA plates were coated with 100 ng/mL human TNFα in 250 µg/mL bovine serum albumin (BSA) in phosphate buffered saline (1×PBS) and blocked with 1% BSA in 1×PBS. 1% BSA plus 0.1 mM PMSF was used as the assay diluent for all experiments on polypeptides that had trypsin pre-treatment. Otherwise 1% BSA was used as an assay diluent. Biotinylated adalimumab (LGC) was mixed 1:1 with all standards and samples to give a final concentration of 2 nM biotinylated adalimumab before adding the mixtures to the plates. Bound biotinylated adalimumab was detected using ExtrAvidin-horseradish peroxidase (Sigma E2886) and visualized using TMB Microwell Substrate (KPL 50-76-00) before stopping with 0.5M $H_2SO_4$ and reading at 450 nm FA1K (pre- and post-trypsin treatment) was found to be substantially as potent as ID-38F in this competition ELISA.

Figure 4:
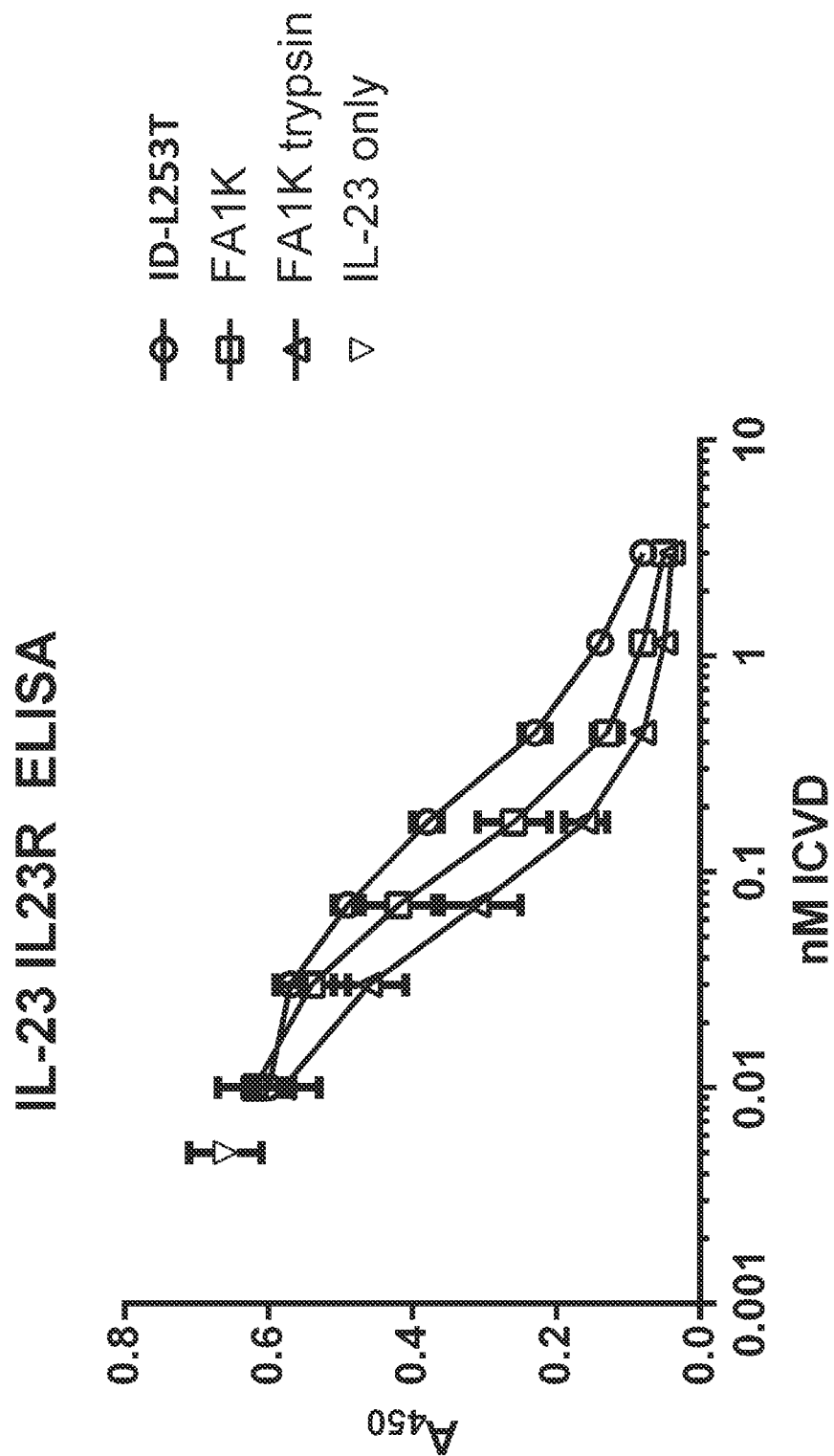

The neutralising potency of FA1K (pre- and post-trypsin cleavage) against IL-23 was investigated (see FIG. 4 wherein 'FA1K' refers to FA1K pre-trypsin treatment, 'FA1K trypsin' refers to FA1K post-trypsin treatment). FA1K (pre- and post-trypsin treatment) was at least as potent against IL-23 as ID-L253T.

The inclusion of ID-L253T in the C-terminal position of FA1K, such that the ID-L253T arm has an N-terminal extension compared to the free ID-L253T monomer may also appear to provide a benefit for IL-23 neutralisation.

FA1K produced and purified from expression in P. pastoris was also confirmed to be fully potent against both TNF-alpha and IL-23 by ELISA (data not shown).

Figure 5:
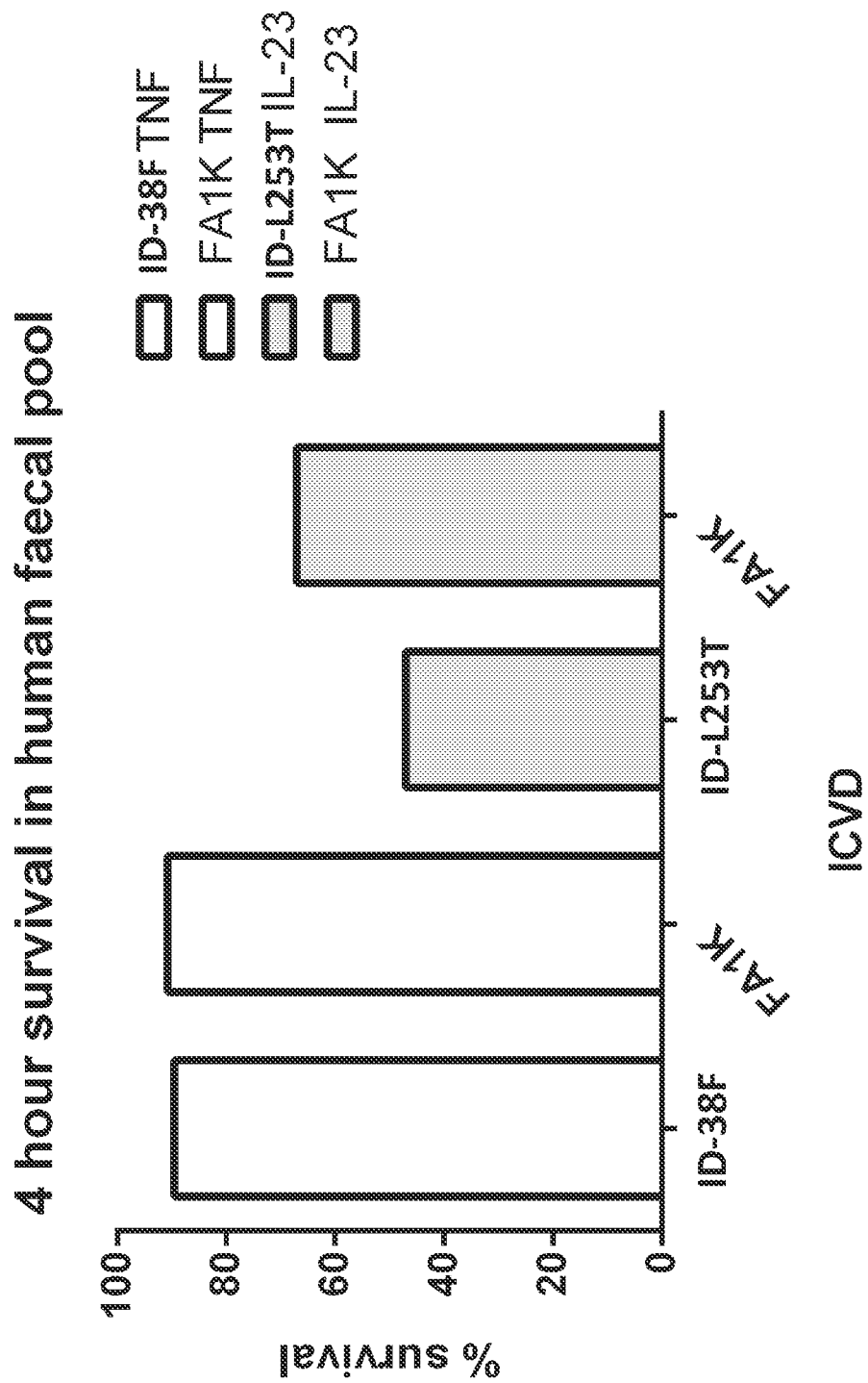
FIG. 5—Stability of FA1K parent monomers ID-38F and ID-L253T following incubation for 4 hours in human faecal supernatant FIG. 6—Average phospho-intensity values for ex vivo UC inflamed colonic mucosal tissue treated with ID-L210T and ID-38F FIG. 7—Average phospho-intensity values for ex vivo UC inflamed colonic mucosal tissue treated with ID-L210T and ID-38F (continued)

Both of the monomer arms of FA1K were shown to retain the favourable stability characteristics of parent monomers ID-38F and ID-L253T following incubation for 4 hours in human faecal supernatant (see FIG. 5, wherein from left to right the % survival of (a) ID-38F, (b) ID-38F in FA1K monomer arm form, (c) ID-L253T and (d) ID-L253T in FA1K monomer arm form is given.

Taken together, the findings above demonstrate that FA1K is a suitable format to deliver high concentrations of each of these monomers as a dual therapy. FA1K retains the favourable potency and protease stability characteristics of the parent monomers. Due to the labile linker format, FA1K exposure to trypsin results in rapid release of both monomer arms, enabling independent binding to their respective targets without interference from the other arm.

Example 11: Ex Vivo Characterisation of Combined Anti-IL-23 (ID-L210T) and Anti-TNF-Alpha (ID-38F) Administration to Human IBD Tissue It has been demonstrated above and in other publications that ICVDs with TNF-alpha neutralising activities (ID-38F) and IL-23 neutralising activities (ID-L210T) can suppress the phosphorylation of tyrosine kinase receptors and signalling proteins that are increased in inflamed intestinal tissue samples taken from patients with a diagnosis of IBD (see Example 8 above and WO2016156465, Example 9 therein).

A new study was conducted to investigate the effects of combining ID-38F with L210T on the levels of phosphoprotein biomarkers in ex vivo cultures of inflamed colonic mucosal tissue obtained from patients with UC. ID-L210T differs from ID-L253T in only three amino acids and shows similar IL-23-IL-23R inhibition potencies and resistance to in vitro digestion.

Effects of the individual ICVDs were compared with a mixture of the two ICVDs and with an isotype control ICVD (ID-2A, an irrelevant anti-C. difficile toxin ICVD) to assess what effects could be achieved by combining the different anti-cytokine mechanisms.

Figure 6:
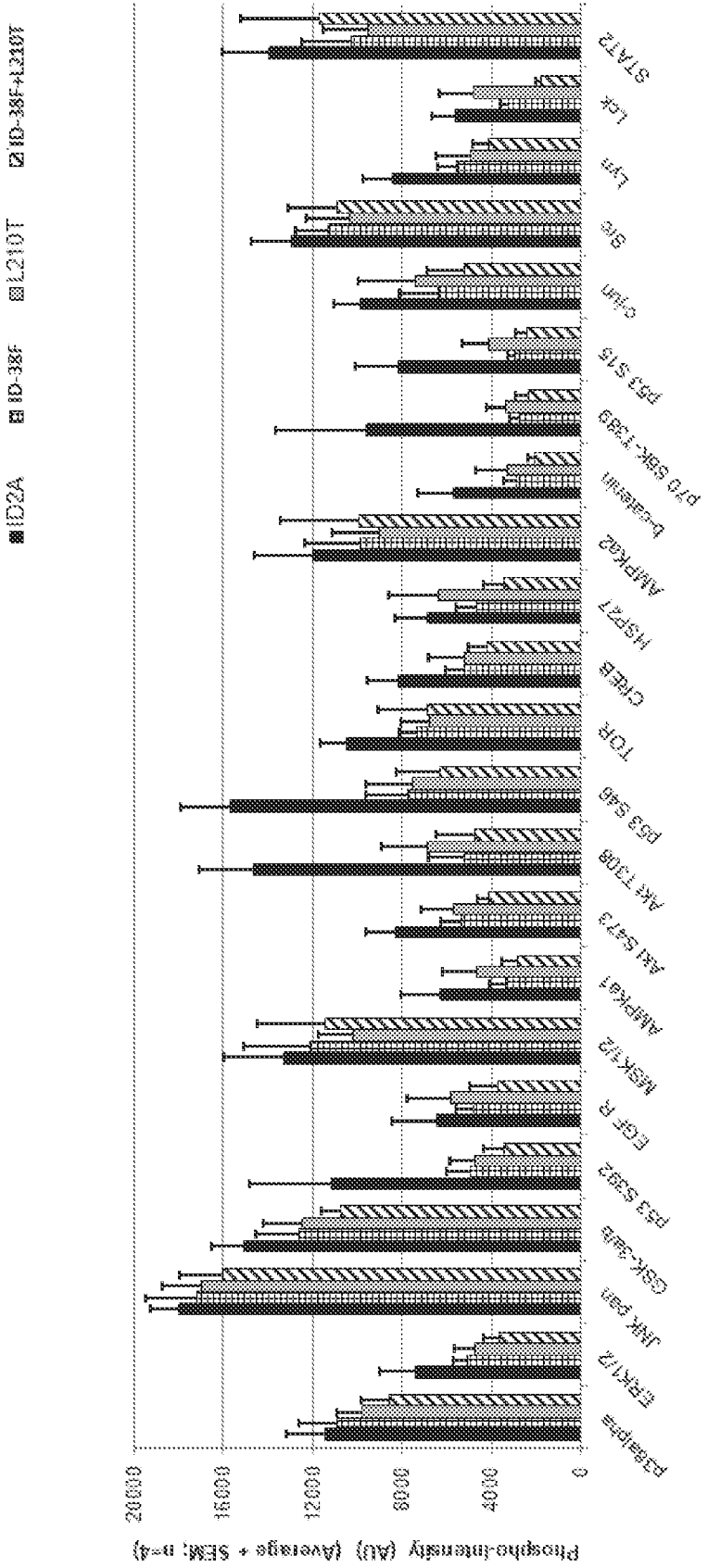
Figure 7:
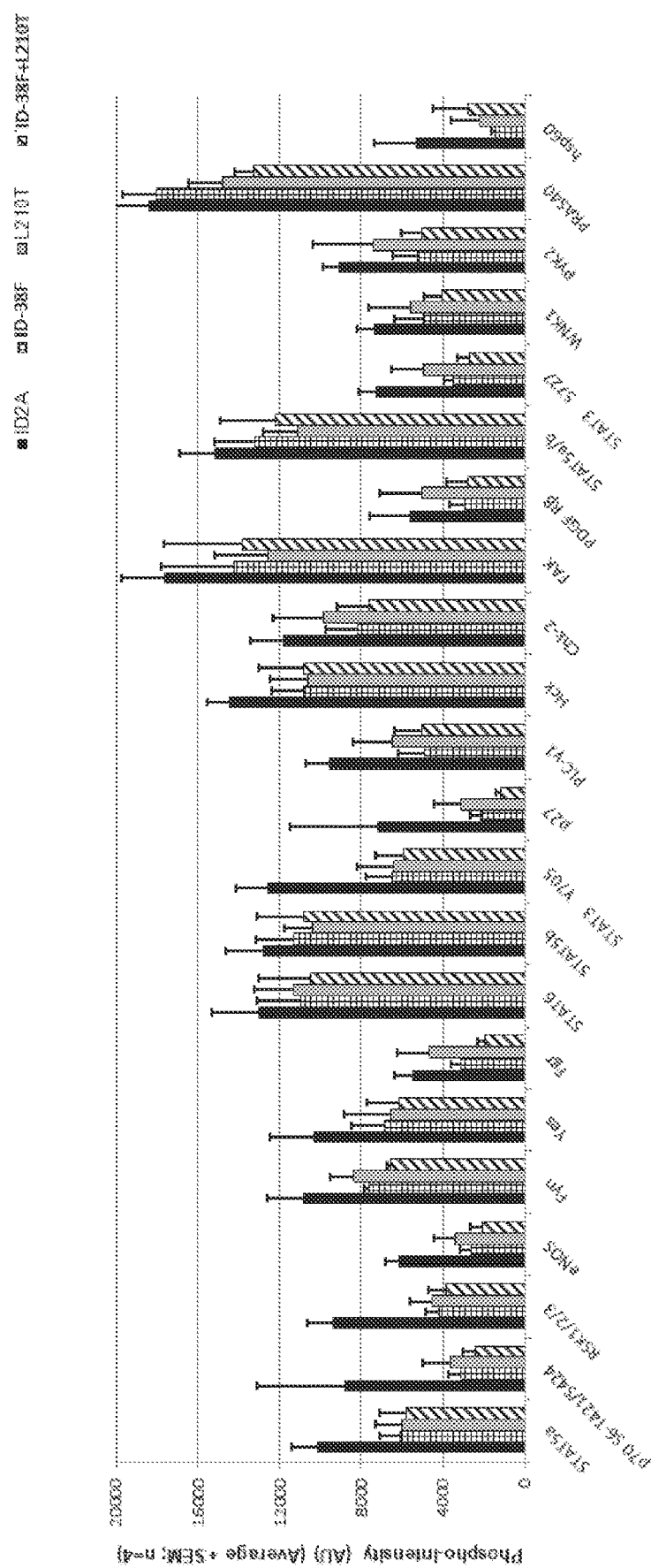

Biopsies from each of four UC patients were incubated for 24 hours with the different antibodies (control ID-2A, ID-38F, ID-L210T or ID-38F+ID-L210T) and following treatment the tissue lysates were analysed on phosphoprotein antibody arrays. Averaged signal intensity data per patient for the 45 phosphoproteins detected on the individual arrays (4 arrays per treatment) are presented in FIGS. 6-7 (wherein L210T refers to ID-L210T). The inhibitory effects of the different antibody treatments are demonstrated by a shift from predominantly high levels of phosphorylation for biopsies treated with the control ICVD ID2A, to relatively low phospho-intensity values for biopsies treated with the anti-TNF-alpha or anti-IL-23 ICVD or a combination of the two.

The data provided herein illustrates that a therapeutic approach that combines GI restricted antagonism of TNF-alpha and IL-23 may achieve a greater degree of efficacy, for a longer duration, in a higher proportion of patients with inflammatory bowel disease, than monotherapy against either target alone.

Miscellaneous

All references referred to in this application, including patent and patent applications, are incorporated herein by reference to the fullest extent possible.

Throughout the specification, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

REFERENCES

The references below are herein incorporated by reference in their entirety.
Arbabi-Ghahroudi et al *FEBS Lett* 1997 414:521-526
Biancheri et al 2015 *Gastroenterology* 149(6):1564-1574
Blattler et al *Biochemistry* 1985 24:1517-1524
Chomezynnski and Sacchi *Anal Biochem* 1987 162:156-159
Colombel et al *Gastroenterology* 2007132:52-65
Crowe et al 2018 *Sci. Rep.* 8:1-13
Croxford et al *Eur J Immunol.* 2012 42:2263-2273
Desmyter et al. *Front Immunol* 2017 8(884):1-10
Eken et al *Inflamm Bowel Dis.* 2014 20:587-595
Faisst et al *J Virol* 1995 69:4538-4543
Frenken et al *J Biotech* 2000 78:11-21
Furfaro et al *Expert Rev Clin Immunol.* 2017 13:1-11
Green and Sambrook *Molecular Cloning: A Laboratory Manual* 2012 4th Edition Cold Spring Harbour Laboratory Press
Griffiths et al *Antibodies* 2013 2:66-81
Grundstrom et al *Nucl. Acids Res* 1985 13:3305-3316
Hamers-Casterman et al *Nature* 1993 363(6428):446-448
Hanauer et al *Lancet* 2002 359:1541-1549
Hanauer et al *Gastroenterology* 2006 130:323-333
Harmsen et al *Gene* 1993 125:115-123
Harmsen et al *Appl Microbiol Biotechnol* 2007 77(1):13-22)
Hendrickson et al *Clin Microbiol Rev* 2002 15(1):79-94
Hoogenboom et al *Nucl Acid Res* 1991 19:4133-4137
Huse et al *Science* 1989 246 (4935):1275-1281
Kabat et al *Sequences of Proteins of Immunological Interest*, Fifth Edition U.S. Department of Health and Human Services, 1991 NIH Publication Number 91-3242
Knezevic et al 2012 *Journal of the American Chemical Society* 134(37):15225-15228
Köhler and Milstein *Nature* 1975 256:495-497
Ling et al *Anal Biochem* 1997 254(2):157-178
McCoy et al *Retrovirology* 2014 11:83
McGovern and Powrie *Gut* 2007 56:1333-1336
Merchlinsky et al *J. Virol.* 1983 47:227-232
Miethe et al *J Biotech* 2013 163(2):105-111
Muyldermans et al *Protein Eng* 1994 7(9):1129-1135
Muyldermans *Annu Rev Biochem* 2013 82:775-797
Nambiar et al *Science* 1984 223:1299-1301
Nelson et al *Molecular Pathology* 2000 53(3):111-117
Nguyen et al *Adv Immunol* 2001 79:261-296
Ortonne, Brit *J Dermatol* 1999 140(suppl 54):1-7
Padlan *Mol Immunol* 1994 31:169-217
Roux et al *Proc Natl Acad Sci USA* 1998 95:11804-11809
Sandborn et al *N Engl J Med.* 2007 357:228-238
Sakamar and Khorana *Nucl. Acids Res* 1988 14:6361-6372
Schreiber et al *N Engl J Med.* 2007 357:239-250
Skerra et al *Science* 1988 240(4855):1038-1041
Tanha et al *J Immunol Methods* 2002 263:97-109
Teng et al *Nat Med.* 2015 21:719-729
Thomassen et al *Enzyme and Micro Tech* 2002 30:273-278
Verma and Eckstein *Annu Rev Biochem* 1998 67:99-134
Vossenkamper et al 2014 *Gastroenterology* 147(1):172-183
Ward et al *Nature* 1989 341:544-546
Wells et al *Gene* 1985 34:315-323

The invention claimed is:

1. A polypeptide comprising a first immunoglobulin heavy chain variable domain that binds to IL-23 and a second immunoglobulin heavy chain variable domain that binds to TNF-alpha, wherein the first immunoglobulin heavy chain variable domain comprises:
   (a) a complementarity determining region 1 (CDR1) comprising the amino acid sequence as set forth in SEQ ID NO: 1, a complementarity determining region 2 (CDR2) comprising the amino acid sequence as set forth in SEQ ID NO: 2, and a complementarity determining region 3 (CDR3) comprising the amino acid sequence as set forth in SEQ ID NO: 3;
   (b) a CDR1 comprising the amino acid sequence as set forth in SEQ ID NO: 14, a CDR2 comprising the amino acid sequence as set forth in SEQ ID NO: 15, and a CDR3 comprising the amino acid sequence as set forth in SEQ ID NO: 16; or
   (c) a CDR1 comprising the amino acid sequence as set forth in SEQ ID NO: 22, a CDR2 comprising the amino acid sequence as set forth in SEQ ID NO: 23, and a CDR3 comprising the amino acid sequence as set forth in SEQ ID NO: 24;
wherein the first immunoglobulin heavy chain variable domain binds to IL-23 and the second immunoglobulin heavy chain variable domain binds to TNF-alpha.

2. The polypeptide of claim 1, wherein: the CDR1 of the first immunoglobulin chain variable domain comprises the amino acid sequence as set forth in SEQ ID NO: 1, the CDR2 of the first immunoglobulin chain variable domain comprises the amino acid sequence as set forth in SEQ ID NO: 2, and the CDR3 of the first immunoglobulin chain variable domain comprises the amino acid sequence as set forth in SEQ ID NO: 3.

3. The polypeptide of claim 1, wherein the first immunoglobulin chain variable domain comprises: the CDR1 of the first immunoglobulin chain variable domain comprises the amino acid sequence as set forth in SEQ ID NO: 14, the CDR2 of the first immunoglobulin chain variable domain comprises the amino acid sequence as set forth in SEQ ID NO: 15, and the CDR3 of the first immunoglobulin chain variable domain comprises the amino acid sequence as set forth in SEQ ID NO: 16.

4. The polypeptide of claim 1, wherein the first immunoglobulin heavy chain variable domain comprises: the CDR1 of the first immunoglobulin chain variable domain comprises the amino acid sequence as set forth in SEQ ID NO: 22, the CDR2 of the first immunoglobulin chain variable domain comprises the amino acid sequence as set forth in SEQ ID NO: 23, and the CDR3 of the first immunoglobulin chain variable domain comprises the amino acid sequence as set forth in SEQ ID NO: 24.

5. The polypeptide of claim 1, wherein the second immunoglobulin heavy chain variable domain comprises: a complementarity determining region 1 (CDR1) comprising the amino acid sequence of SEQ ID NO: 78, a complementarity determining region 2 (CDR2) comprising the amino acid sequence of SEQ ID NO: 79, and a complementarity determining region 3 (CDR3) comprising the amino acid sequence of SEQ ID NO: 80.

6. The polypeptide of claim 1, wherein the first immunoglobulin heavy chain variable domain comprises 80% or greater sequence identity to SEQ ID NO: 48.

7. The polypeptide of claim 1, wherein the second immunoglobulin heavy chain variable domain comprises 80% or greater sequence identity to SEQ ID NO: 67.

8. The polypeptide of claim 1, wherein the first immunoglobulin heavy chain variable domain and the second immunoglobulin heavy chain variable domain are each a VHH.

9. The polypeptide of claim 1, wherein the polypeptide comprises a protease-labile linker connecting the first immunoglobulin heavy chain variable domain and the second immunoglobulin heavy chain variable domain.

10. The polypeptide of claim 9, wherein the protease-labile linker comprises an amino acid sequence:

$[-(G_4S)_x-B-(G_4S)_y-]$, wherein x is 1 to 10;

y is 1 to 10; and

B is a Lysine (K) or an Arginine (R).

11. The polypeptide of claim 10, wherein the protease-labile linker comprises an amino acid sequence:

$[-(G_4S)_x-B-(G_4S)_y-]_z$, wherein x is 1 to 10;

y is 1 to 10;

z is 1 to 10; and

B is a Lysine (K) or an Arginine (R).

12. The polypeptide of claim 10, wherein the protease-labile linker comprises the amino acid sequence as set forth in SEQ ID NO: 49.

13. A method of treating an autoimmune and/or inflammatory disease comprising administering to an individual in need thereof the polypeptide of claim 1.

14. A polypeptide that binds to IL-23 comprising the amino acid sequence as set forth in SEQ ID NO: 46.

15. A method of treating an autoimmune and/or inflammatory disease in an individual in need thereof comprising administering to the individual the polypeptide of claim 14.

* * * * *